(12) United States Patent
Shimizu et al.

(10) Patent No.: US 8,137,963 B2
(45) Date of Patent: Mar. 20, 2012

(54) METHOD FOR HIGHLY AMPLIFYING TARGET GENE IN MAMMALIAN CELL AND VECTOR THEREFOR

(75) Inventors: Noriaki Shimizu, Higashi-Hiroshima (JP); Toshihiko Hashizume, Higashi-Hiroshima (JP); Masashi Shimizu, Tsuruga (JP)

(73) Assignee: Hiroshima University, Hiroshima (JP)

( * ) Notice: Subject to any disclaimer, the term of this patent is extended or adjusted under 35 U.S.C. 154(b) by 387 days.

(21) Appl. No.: 12/438,545

(22) PCT Filed: Aug. 20, 2007

(86) PCT No.: PCT/JP2007/066133
§ 371 (c)(1),
(2), (4) Date: Feb. 23, 2009

(87) PCT Pub. No.: WO2008/023671
PCT Pub. Date: Feb. 28, 2008

(65) Prior Publication Data
US 2010/0317060 A1     Dec. 16, 2010

(30) Foreign Application Priority Data
Aug. 24, 2006   (JP) ................................ 2006-228396

(51) Int. Cl.
*C12N 15/63* (2006.01)
*C12N 15/85* (2006.01)
*C12P 19/34* (2006.01)
(52) U.S. Cl. ..................... 435/320.1; 435/325; 435/91.2
(58) Field of Classification Search .................. None
See application file for complete search history.

(56) References Cited

U.S. PATENT DOCUMENTS

2011/0144128 A1* 6/2011 Flatt et al. .................... 514/256

FOREIGN PATENT DOCUMENTS

| JP | 2003-245083 A | 9/2003 | |
|---|---|---|---|
| JP | 2006-055175 A | 3/2006 | |
| WO | WO 03/016500 A2 * | 2/2003 | .................... 514/44 |

OTHER PUBLICATIONS

Aladjem, M. I. et al. (Aug. 14, 1998). "Genetic Dissection of a Mammalian Replicator in the Human β-Globin Locus," *Science* 281:1005-1009.
Dijkwel, P. A. et al. (Dec. 1988). "Matrix Attachment Regions are Positioned Near Replication Initiation Sites, Genes, and an Interamplicon Junction in the Amplified Dihydrofolate Reductase Domain of Chinese Hamster Ovary Cells," *Molecular and Cellular Biology* 8(12):5398-5409.

International Search Report mailed Oct. 30, 2007, for PCT Application No. PCT/JP2007/066133 filed Aug. 20, 2007, 2 pages.
Jenke, A. C. W. et al. (Aug. 3, 2004). "Nuclear Scaffold/Matrix Attached Region Modules Linked to a Transcription Unit are Sufficient for Replication and Maintenance of a Mammalian Episome," *Proceedings of the National Academy of Sciences of the United States of America* 101(31):11322-11327.
McWhinney, C. et al. (1990). "Autonomous Replication of a DNA Fragment Containing the Chromosomal Replication Origin of the Human c-myc Gene," *Nucleic Acids Research* 18(5):1233-1242.
Pommier, Y. et al. (Jan. 1990). "Identification Within the Simian Virus 40 Genome of a Chromosomal Loop Attachment Site that Contains Topoisomerase II Cleavage Sites," *The Journal of Virology* 64(1):419-423.
Schaarschmidt, D. et al. (2004). "An Episomal Mammalian Replicon: Sequence-Independent Binding of the Origin Recognition Complex," *The EMBO Journal* 23(1):191-201.
Shimizu, N. et al. (Jan. 1996). "Selective Capture of Acentric Fragments by Micronuclei Provides a Rapid Method for Purifying Extrachromosomally Amplified DNA," *Nature Genetics* 12:65-71.
Shimizu, N. et al. (Oct. 1, 2001). "Plasmids with a Mammalian Replication Origin and a Matrix Attachment Region Initiate the Event Similar to Gene Amplification," *Cancer Research* 61:6987-6990.
Tsutsui, K. et al. (Jun. 15, 1993). "Identification and Characterization of a Nuclear Scaffold Protein that Binds the Matrix Attachment Region DNA," *The Journal of Biological Chemistry* 268(17):12886-12894.
Aladjem, M.I. et al. (Jul. 1, 2004). "The relicon revisited: an old model learns new tricks in metazoan chromosomes," *EMBO Reports* 5(7):686-691.
Altman, A.L. et al. (Feb. 2001). "The Chinese Hamster Dihydrofolate Reductase Replication Origin Beta Is Active at Multiple Ectopic Chromosomal Locations and Requires Specific DNA Sequence Elements for Activity," *Molecular and Cell Biology* 21(4):1098-1110.
Berberich, S. et al. (1995). "In vitro replication of plasmids containing human c-myc DNA," *Journal of Molecular Biology* 245(2):92-109.
Supplementary European Search Report mailed Aug. 31, 2009, for EP Application No. 07792746.5 filed Mar. 5, 2009, 3 pages.

\* cited by examiner

*Primary Examiner* — Amy Bowman
(74) *Attorney, Agent, or Firm* — Morrison & Foerster LLP

(57) ABSTRACT

A vector of the present invention is a vector for amplifying a target gene in a mammalian cell, the vector including an amplification-activating fragment, which is a partial fragment of a mammalian replication initiation region and has a gene amplification activity site, and a mammalian nuclear matrix attachment region. In the case where the mammalian replication initiation region as described above derives from a c-myc locus, for example, the above-described partial fragment at least contains a duplex unwinding element and a topoisomerase II-binding domain. The vector as described above improves gene transfer efficiency and gene amplification efficiency compared with the existing high gene amplification systems. Thus, a method whereby a "high gene amplification system" developed by the inventors can amplify a target gene with better gene transfer efficiency and a vector to be used in this method are provided.

5 Claims, 9 Drawing Sheets

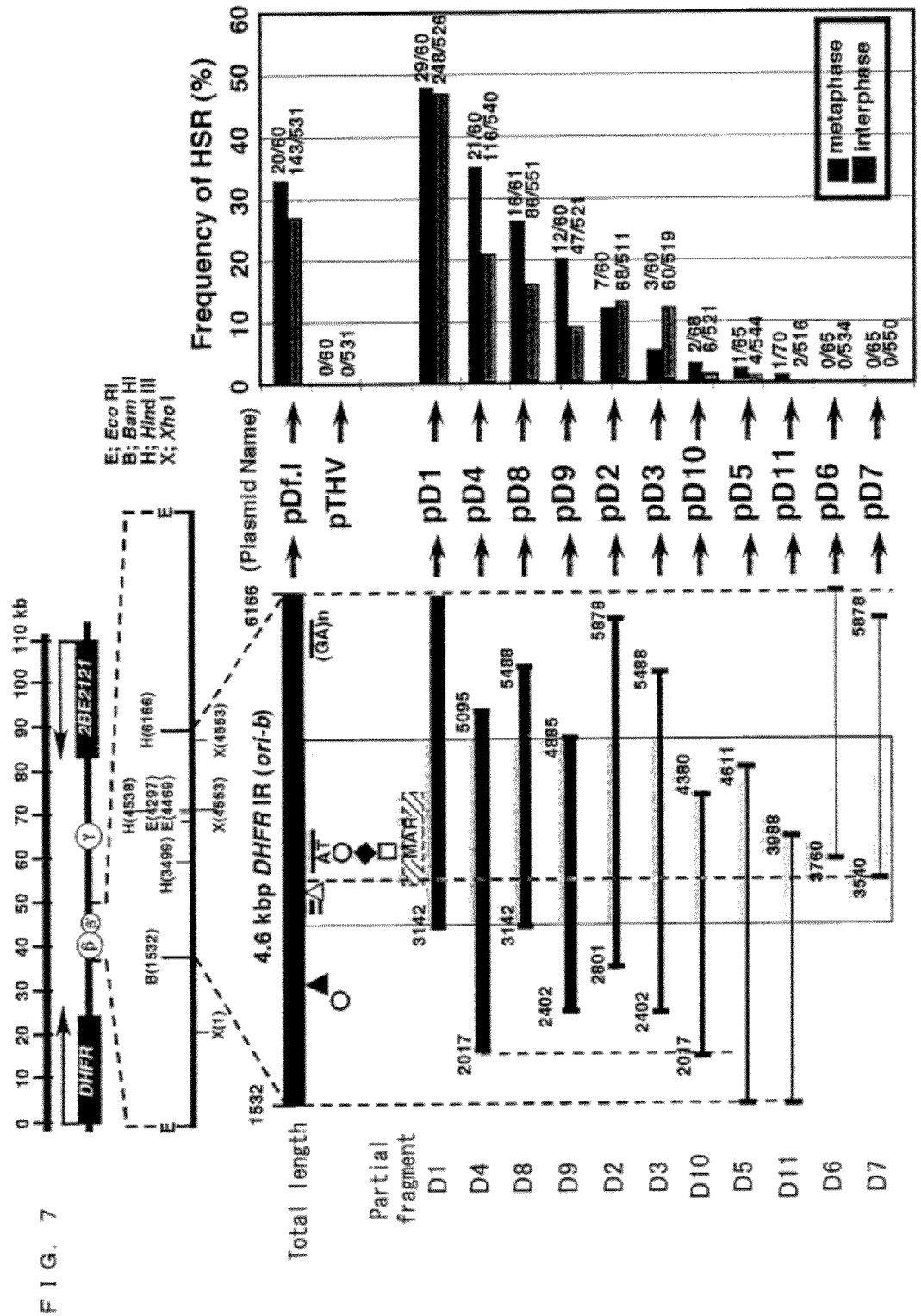
F I G. 7

METHOD FOR HIGHLY AMPLIFYING TARGET GENE IN MAMMALIAN CELL AND VECTOR THEREFOR

CROSS REFERENCE TO RELATED APPLICATIONS

This is a U.S. National Phase patent application of PCT/JP2007/066133, filed Aug. 20, 2007, which claims priority to Japanese patent application Serial No. 2006-228396, filed Aug. 24, 2006, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322008400SubSeqListing.txt, date recorded: Aug. 4, 2010, size: 125 KB).

TECHNICAL FIELD

The present invention relates to a method for highly amplifying a target gene in a mammalian cell and a vector for use in carrying out the same method. More specifically, the present invention relates to (i) a method whereby a "high gene amplification system" developed by the inventors can amplify a target gene with better gene transfer efficiency and (ii) a vector to be used in this method.

BACKGROUND ART

The inventors found that, simply by transferring a plasmid (hereinafter called "IR/MAR plasmid") including a mammalian replication initiation region (IR; Initiation Region) and a mammalian nuclear matrix attachment region (MAR; Matrix Attachment Region) to a human-derived cancer cell (COLO 320 colon cancer cell strain and HeLa cell strain) by a lipofection method and then selecting the cell by utilizing a drug resistance gene (Blasticidin or Neomycin) being present on the plasmid, it is possible to:
(1) increase a copy number of a gene inside the cell up to approximately 10,000 copies, the gene encoding a protein to be expressed (hereinafter, the gene is referred to as "target gene", as needed), and
(2) highly amplify the target gene in either cases where the target gene and the IR/MAR plasmid are transferred in the same gene construct (cis) or where the target gene and the IR/MAR plasmid are transferred respectively in different gene constructs (trans) (refer to Patent Literature 1 and Non Patent Literature 1). Based on the findings, the inventors realized a system (hereinafter called "high gene amplification system"), which makes it possible to amplify the target gene up to approximately 10,000 copies, simply by performing the steps of: transferring the IR/MAR plasmid and the target gene to the mammalian cell (e.g., human-derived cancer cell (COLO 320 colon cancer cell strain and HeLa cell strain) and CHO cell) by the lipofection method; and selecting the cell by utilizing the drug resistance gene (Blasticidin or Neomycin) being present on the plasmid.

FIG. 1 illustrates a mechanism on how a DM and HSR are generated by the IR/MAR plasmid (also called "IR/MAR vector"). The IR/MAR plasmids are bound as direct repeats within a host cell, so as to form a multimeric complex thereof (Step 1). The multimeric complex is stably present in the host cell and is replicated autonomously while the cell is growing. The multimeric complex is cytogenetically recognized as a DM when the multimeric complex grows to a large size, or when the multimeric complex is integrated into a preexisting DM within the host cell. Further, as illustrated in Step 2, a double strand of a circular DNA of the multimeric complex is broken (DSB; double strand breakage) within the host cell, thereby the circular DNA turns into a linear DNA. Then, the linear DNA is integrated into a chromosome. Then a BFB (Breakage-Fusion-Bridge) cycle as illustrated in Step 3 is initiated, thereby triggering HSR generation.

CITATION LIST

Patent Literature 1

Japanese Patent Application Publication, Tokukai, No. 2003-245083 (Publication Date: Sep. 2, 2003)

Non Patent Literature 1

Noriaki Shimizu, et al. (2001) Plasmids with a Mammalian Replication Origin and a Matrix Attachment Region Initiate the Event Similar to Gene Amplification. Cancer Research vol. 61, no. 19, p 6987-6990.

SUMMARY OF INVENTION

An MAR used in a high gene amplification system of Patent Literature 1 is a polynucleotide of several hundred bp, but an IR is as long as several kbp. For example, an IR derived from a c-myc locus is 2.4 kbp, whereas an IR derived from a dihydrofolate reductase (hereinafter referred to as "DHFR", as needed) is 4.6 kbp. Therefore, an IR/MAR plasmid is a relatively large gene construct.

In amplifying a target gene by using the high gene amplification system, the IR/MAR plasmid and the target gene are transferred to a mammalian cell. In this process, if the IR/MAR plasmid was smaller in size, the following advantages are expected:
(A) Gene transfer into the mammalian cell can be performed more efficiently;
(B) It becomes possible to deal with a target gene of a larger size by the high gene amplification system;
(C) A polynucleotide that encodes another element such as a tagged protein or signal peptide can be easily integrated into the IR/MAR plasmid, so that more complicated vector can be prepared.

Under this circumstance, an object of the present invention is to further improve the high gene amplification system. More specifically, an object of the present invention is to develop a vector that can achieve the above advantages (A) to (C), and to provide a method for amplifying the target gene by using the vector.

In order to attain the above objects, the inventors have diligently studied on the IR of the IR/MAR plasmid, and found a partial fragment of the IR, which partial fragment can highly amplify the target gene. Based on the finding, the inventors have accomplished the present invention.

It was a remarkable finding that, with the high gene amplification system with the partial fragment of the IR described above, the target gene can be amplified with a significantly higher frequency of HSR, compared to the high gene amplification system with a full-length IR. This effect was beyond the expectation of those skilled in the art. Further, the target gene amplification by the high gene amplification system with the partial fragment of the IR described above led to a high level of protein production although a level of gene amplification was about the same as in the case the high gene amplification system with the full-length IR was used. This effect was beyond the expectation of those skilled in the art.

The present invention includes the following inventions in order to attain the above objects.

A method according to the present invention is a method of amplifying a target gene, the method comprising:

transferring a vector and the target gene to a mammalian cell, the vector including:

an amplification-activating fragment being a partial fragment of a mammalian replication initiation region, and having a gene amplification activity site; and a mammalian nuclear matrix attachment region.

The method of the present invention may be a method wherein the mammalian replication initiation region derives from a replication initiation region of a locus selected from the group consisting of a c-myc locus, a dihydrofolate reductase locus, and a β-globin locus.

The method of the present invention may be a method wherein the amplification-activating fragment derives from a c-myc locus and contains at least a Duplex Unwinding Element and a topoisomerase II-binding domain.

The method of the present invention may be a method as set forth in claim 1, wherein the amplification-activating fragment derives from a c-myc locus, and contains:

(a) a polynucleotide having the base sequence shown in SEQ ID NO: 1, or a polynucleotide in which one or several bases are deleted, substituted, or added from/to the base sequence shown in SEQ ID NO: 1; and (b) a polynucleotide having the base sequence shown in SEQ ID NO: 2, or a polynucleotide in which one or several bases are deleted, substituted, or added from/to the base sequence shown in SEQ ID NO: 2.

The method according to the present invention may be a method wherein the amplification-activating fragment contains a polynucleotide having the base sequence shown in SEQ ID NO: 3, or a polynucleotide in which one or several bases are deleted, substituted, or added from/to the base sequence shown in SEQ ID NO: 3.

The method according to the present invention may be a method wherein the amplification-activating fragment contains a polynucleotide having the base sequence shown in SEQ ID NO: 4, or a polynucleotide in which one or several bases are deleted, substituted, or added from/to the base sequence shown in SEQ ID NO: 4.

The method according to the present invention may be a method wherein the amplification-activating fragment contains a polynucleotide having the base sequence shown in SEQ ID NO: 5, or a polynucleotide in which one or several bases are deleted, substituted, or added from/to the base sequence shown in SEQ ID NO: 5.

The method according to the present invention may be a method wherein the amplification-activating fragment derives from a dihydrofolate reductase locus and contains a polynucleotide having the base sequence shown in SEQ ID NO: 10, or a polynucleotide in which one or several bases are deleted, substituted, or added from/to the base sequence shown in SEQ ID NO: 10.

The method according to the present invention may be a method wherein the amplification-activating fragment derives from a dihydrofolate reductase locus, and contains a polynucleotide having the base sequence shown in SEQ ID NO: 11, or a polynucleotide in which one or several bases are deleted, substituted, or added from/to the base sequence shown in SEQ ID NO: 11.

The method according to the present invention may be a method wherein the mammalian nuclear matrix attachment region derives from a nuclear matrix attachment region of a region selected from the group consisting of an Igκ locus, an SV40 early region, and a dihydrofolate reductase locus.

The method of the present invention may be a method wherein the target gene and the vector are transferred to the mammalian cell in such a manner that the target gene and the vector are arranged in trans.

On the other hand, a vector according to the present invention is a vector for amplifying a target gene in a mammalian cell, the vector comprising a vector including:

an amplification-activating fragment being a partial fragment of a mammalian replication initiation region, and having a gene amplification activity site;

a mammalian nuclear matrix attachment region; and a gene for selecting a transformed cell.

The vector according to the present invention may be a vector wherein the mammalian replication initiation region derives from a replication initiation region of a locus selected from the group consisting of a c-myc locus, a dihydrofolate reductase locus, and a β-globin locus.

The vector according to the present invention may be a vector wherein the amplification-activating fragment derives from a c-myc locus, and contains at least a Duplex Unwinding Element and a topoisomerase II-binding domain.

The vector according to the present invention may be a vector wherein the amplification-activating fragment derives from a c-myc locus, and contains:

(a) a polynucleotide having the base sequence shown in SEQ ID NO: 1, or a polynucleotide in which one or several bases are deleted, substituted, or added from/to the base sequence shown in SEQ ID NO: 1; and (b) a polynucleotide having the base sequence shown in SEQ ID NO: 2, or a polynucleotide in which one or several bases are deleted, substituted, or added from/to the base sequence shown in SEQ ID NO: 2.

The vector according to the present invention may be a vector wherein the amplification-activating fragment contains a polynucleotide having the base sequence shown in SEQ ID NO: 3, or a polynucleotide in which one or several bases are deleted, substituted, or added from/to the base sequence shown in SEQ ID NO: 3.

The vector according to the present invention may be a vector wherein the amplification-activating fragment contains a polynucleotide having the base sequence shown in SEQ ID NO: 4, or a polynucleotide in which one or several bases are deleted, substituted, or added from/to the base sequence shown in SEQ ID NO: 4.

The vector according to the present invention may be a vector wherein the amplification-activating fragment contains a polynucleotide having the base sequence shown in SEQ ID NO: 5, or a polynucleotide in which one or several bases are deleted, substituted, or added from/to the base sequence shown in SEQ ID NO: 5.

The vector according to the present invention may be a vector wherein the amplification-activating fragment derives from a dihydrofolate reductase locus, and contains a polynucleotide having the base sequence shown in SEQ ID NO: 10, or a polynucleotide in which one or several bases are deleted, substituted, or added from/to the base sequence shown in SEQ ID NO: 10.

The vector according to the present invention may be a vector wherein the amplification-activating fragment derives from a dihydrofolate reductase locus, and contains a polynucleotide having the base sequence shown in SEQ ID NO:

11, or a polynucleotide in which one or several bases are deleted, substituted, or added from/to the base sequence shown in SEQ ID NO: 11.

The vector according to the present invention may be a vector wherein the mammalian nuclear matrix attachment region derives from a nuclear matrix attachment region of a region selected from the group consisting of an Igκ locus, an SV40 early region, and a dihydrofolate reductase locus.

The amplification-activating fragment is not limited to the polynucleotides specified by the base sequences shown in SEQ ID NOs: 1, 2, 3, 4, 5, 10, and 11, and may be a polynucleotide having the base sequence complementary to the base sequence shown in SEQ ID NO: 1, 2, 3, 4, 5, 10, or 11. The amplification-activating fragment may further be a polynucleotide that is to be hybridized, under a stringent condition, with the polynucleotide specified by the base sequence shown in SEQ ID NO: 1, 2, 3, 4, 5, 10, or 11, or with the polynucleotide having the base sequence complementary to the base sequence shown in SEQ ID NO: 1, 2, 3, 4, 5, 10, or 11. In this Description, the term "stringent condition" means that the hybridization only occurs in the case where the sequences exhibit an identity of at least 90% or higher, preferably at least 95% or higher, most preferably 97%.

On the other hand, a transformant according to the present invention is a transformant wherein a vector according to the present invention and a target gene are transferred to a mammalian cell.

For a fuller understanding of the nature and advantages of the invention, reference should be made to the ensuing detailed description taken in conjunction with the accompanying drawings.

BRIEF DESCRIPTION OF DRAWINGS

FIGS. 2A and 2B show results on transformed cells to which pSFVdhfr was transferred, FIG. 2C shows a result on transformed cells to which pΔHpAx2.dhfr was transferred, FIG. 2D shows a result on transformed cells to which pTH2.dhfr was transferred, and FIG. 2E shows a result on transformed cells to which pEPI-I was transferred.

FIG. 6A is a schematic view of a c-myc locus (GenBank HSMYCC; accession number X00364), and FIGS. 6B and 6C are views showing a positional relation between a full-length c-myc IR and a partial fragment thereof (C0 to C16), and frequency of HSR in transformed cells to which a plasmid (pC0 to pC16) including the partial fragment was transferred.

FIG. 7 is a view showing a result of Example 2. FIG. 7A is a schematic view of a DHFR locus Ori-β region (Genbank CFORIDHFR; accession number X94372), and FIG. 7B is a view showing a positional relation between a full-length IR of the DHFR locus Ori-β region and a partial fragment thereof (C0 to C11), and frequency of HSR in transformed cells to which a plasmid including the partial fragment was transferred.

In FIG. 9, "with no IR/MAR" indicates a result in the case where no IR/MAR plasmid was transfected, "pΔBN.AR1" indicates a result in the case where pΔBN.AR1 was co-transfected, and "pC12.Psv40" indicates a result in the case where pC12.Psv40 was co-transfected.

DESCRIPTION OF EMBODIMENTS

Figure 1:
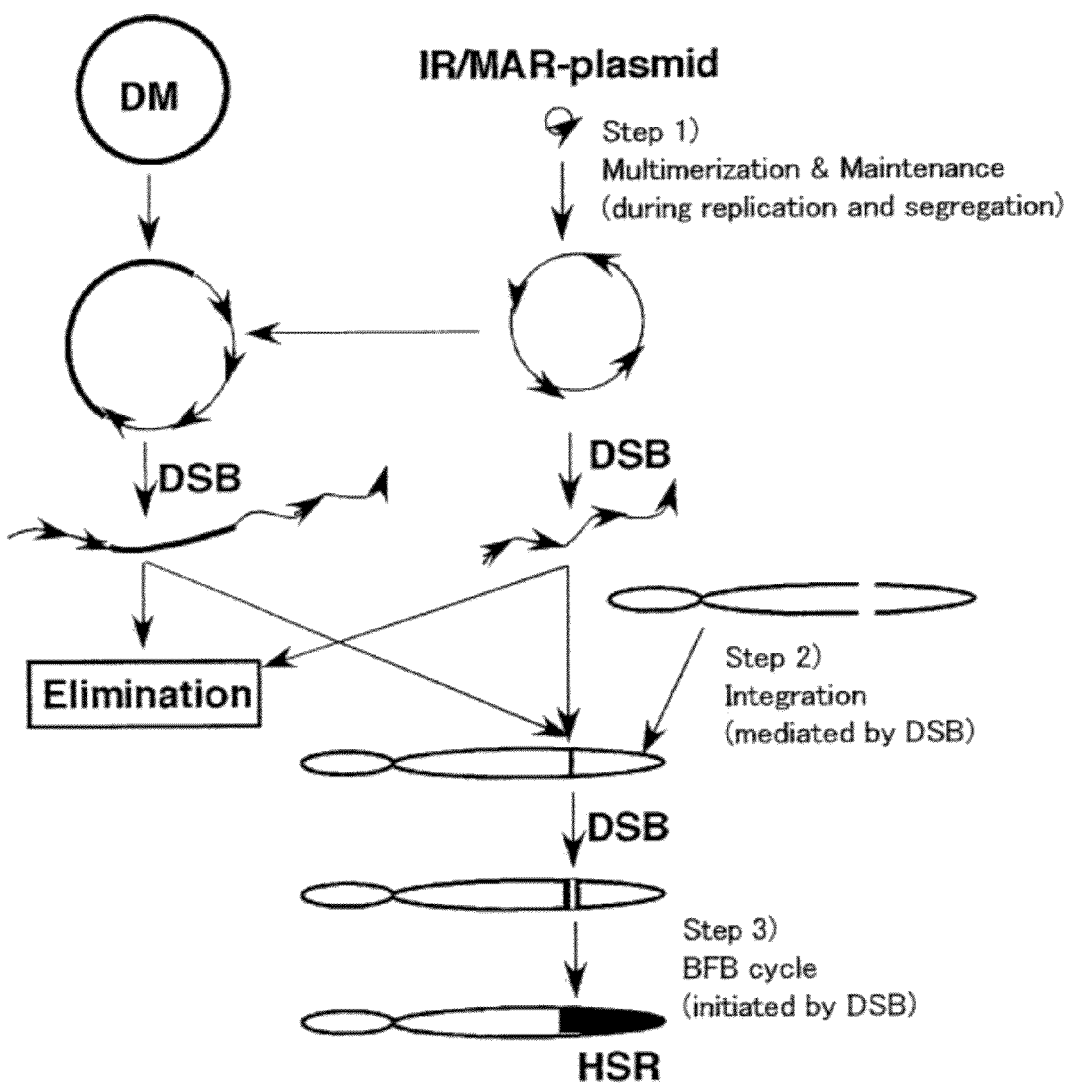
FIG. 1 is a schematic view showing a mechanism on how a DM and HSR are generated by an IR/MAR plasmid.

Details of the present invention are described as follows. However, the present invention is not limited to the description as set forth below and may be altered within the scope of the gist of the present invention. In addition, all the citations stated in the description are incorporated herein by reference.

[1. Gene Amplification Method of the Present Invention]

An embodiment of the present invention relates to a method for amplifying a target gene. The method is called "gene amplification method of the present invention".

Here, the gene amplification method of the present invention comprises the step of:

transferring a vector and the target gene to a mammalian cell, the vector including:
    an amplification-activating fragment being a partial fragment of a mammalian replication initiation region, and having a gene amplification activity site; and
    a mammalian nuclear matrix attachment region
(Hereinafter, the step is referred to as "transferring step").

In this Description, the term "target gene" means a gene that encodes a protein to be expressed. The target gene is not particularly limited, and may be selected as needed from any polynucleotide that encodes a desired protein. The target gene may be a polynucleotide, obtained by using a publicly known technique such as PCR, based on information of a base sequence of the target gene.

The gene amplification method of the present invention amplifies the target gene on a double minute chromosome (hereinafter referred to as "DM", as needed) outside a chromosome, and/or on a homogeneously staining region (hereinafter referred to as "HSR", as needed) of the chromosome. That is, if the target gene was detected on the DM and/or HSR of a clone of a transformed cell, i.e., if an amplification structure was formed, it can be judged that the target gene is amplified successfully. A method for detecting whether the amplification structure is formed on the clone of the transformed cell is not particularly limited. For example, a gene transferred to the mammalian cell can be detected, by performing publicly known FISH (fluorescence in situ hybridization) on the chromosome in a mitotic phase, in order to detect whether the amplification structure is formed or not. This can be easily performed by those skilled in the art. The FISH can be performed in any way and may be carried out in a publicly known manner.

Further, with the gene amplification method of the present invention, amplification efficiency of the target gene can also be significantly improved compared to existing high gene amplification systems (see Examples). This effect is beyond the expectation of those skilled in the art. Whether the amplification efficiency of the target gene is increased or not can be judged by comparing the existing high gene amplification system with the gene amplification method of the present invention in terms of frequency of the gene amplification structure (e.g., frequency of HSR and frequency of DM). If the latter attains a higher frequency than the former, it will be confirmed that the latter method, i.e., the gene amplification method of the present invention, is improved in the amplification efficiency of the target gene, compared to the existing high gene amplification system.

In addition to the transferring step described above, the method according to the present invention may comprise the steps of:

isolating the mammalian cell, to which the target gene and the vector were transferred (hereinafter called "selecting step"); or culturing the mammalian cell (i.e., transformed cell) selected in the selecting step (hereinafter called "culturing step"). The method according to the present invention may further comprise the step of purifying a target protein produced in the culturing step (hereinafter called "purifying step"). Each step of the method according to the present invention is described below.

[1-1. Transferring Step]

A transferring step of the method according to the present invention is:

(i) a step of transferring a vector and a target gene to a mammalian cell, the vector including:

an amplification-activating fragment being a partial fragment of a mammalian replication initiation region, and having a gene amplification activation site;

a mammalian nuclear matrix attachment region; and a gene for selecting a transformed cell.

The mammalian replication initiation region and mammalian nuclear matrix attachment region, which are included in the vector (hereinafter called "IR/MAR plasmid"), are not particularly limited, provided that they are a replication initiation region and a nuclear matrix attachment region that function within a eukaryote cell (e.g., mammalian cell). Examples of the mammalian replication initiation region are mammalian replication initiation regions derived from a c-myc locus, a dihydrofolate reductase (DHFR) locus, and a β-globin locus. For details of the replication initiation region derived from the c-myc locus (hereinafter referred to as "replication initiation region derived from the c-myc locus", as needed), see "McWhinney, C. et al., Nucleic Acids Res. vol. 18, p 1233-1242 (1990)". For details of the replication initiation region of the dihydrofolate reductase locus, see "Dijkwel, P. A. et al., Mol. Cell. Biol. vol. 8, p 5398-5409 (1988)". For details of the replication initiation region of the β-globin locus, see "Aladjem, M. et al., Science vol. 281, p 1005-1009 (1998)".

Moreover, examples of the mammalian nuclear matrix attachment region are polynucleotides derived from nuclear matrix attachment regions of an Igκ locus, an SV40 early region, and a dihydrofolate reductase locus. For details of the nuclear matrix attachment region of the Igκ locus, see "Tsutsui, K. et al., J. Biol. Chem. vol. 268, p 12886-12894 (1993)". For details of the nuclear matrix attachment region of the SV40 early region, see "Pommier, Y. et al., J. Virol., vol 64, p 419-423 (1990)". For details of the nuclear matrix attachment region of the dihydrofolate reductase locus, see "Shimizu N. et al., Cancer Res. vol. 61, p 698'7-6990".

In this Description, unless otherwise stated, the mammalian replication initiation region and the mammalian nuclear matrix attachment region are referred to as "IR" and "MAR", respectively. In addition, not only a vector being formed from a full-length IR and full-length MAR, but also a vector being formed from partial fragments thereof is referred to as "IR/MAR plasmid".

For decreasing the IR/MAR plasmid in size, the gene amplification method of the present invention employs an amplification-activating fragment being a partial fragment of the mammalian replication initiation region (IR) and having a gene amplification activity site. In this Description, the "partial fragment of the mammalian replication initiation region (IR)" is a part of the IR, not the full-length IR. The length of the partial fragment of the IR is not particularly limited. With regard to an IR derived from the c-myc locus of approximately 2.4 kbp, the length is preferably not shorter than 0.5 kbp but not longer than 2.0 kbp, more preferably not shorter than 0.5 kbp but not longer than 1.5 kbp, and most preferably not shorter than 0.5 kbp but not longer than 1.3 kbp. Similarly, with regard to an IR derived from the DHFR locus of approximately 4.6 kbp, the length of the fragment is preferably not shorter than 1.7 kbp but not longer than 3.5 kbp, and more preferably not shorter than 1.7 kbp but not longer than 3.1 kbp. If the preferred ranges are satisfied, the aforementioned effects (A) to (D) are easy to achieve.

In this Description, the "gene amplification activity site" is an essential element for triggering a gene amplification in the high gene amplification system. For example, whether a partial fragment of an IR includes the gene amplification activity site or not can be judged, for example, by analyzing frequency of a gene amplification structure (HSR, DM) in the mammalian cell, to which the target gene and the IR/MAR plasmid produced with use of the partial fragment and an MAR were transferred. That is, in this analysis, if the frequency of the gene amplification structure (HSR, DM) significantly decreased compared to the case of the full-length IR, or if the gene amplification structure (HSR, DM) was not generated anymore, it can be judged that thus analyzed partial fragment of the IR does not include the gene amplification activity site.

Further, it is possible to identify the gene amplification activity site by producing a dilation mutant of the IR and then conducting the above analysis with use of the dilation mutant. The dilation mutant can be obtained from sequence information of the IR, by performing PCR or restriction enzyme digestion.

The studies conducted by the inventors of the present invention demonstrated that, with regard to the IR derived from the c-myc locus, polynucleotides comprising base sequences of SEQ ID NOs: 4, 5, 6, 7, 8 and 9 include the gene amplification activity site.

Based on the result, the inventors conducted further studies and found that, particularly, a Duplex Unwinding Element (hereinafter referred to as "DUE") and topoisomerase II-binding domain correspond to the gene amplification activity site. Thus, the target gene can be highly amplified by using the partial fragment of the IR including at least the DUE and topoisomerase II-binding domain instead of the full-length IR in the IR/MAR plasmid. The partial fragment of the IR may be: a partial fragment consisting only of the DUE and topoisomerase II-binding domain which are derived from the c-myc locus; a partial fragment in which a plurality of the DUEs and topoisomerase II-binding domains are bound together; or a partial fragment including the DUE of the IR derived from the c-myc locus and topoisomerase II-binding domain of the IR derived from the c-myc locus.

An example of a base sequence of the IR derived from the c-myc locus is a base sequence corresponds to bases 1 to 2349 of Genbank HSMYCC (accession number X00364). In this sequence, a preferable example of the partial fragment of the IR including the DUE is a polynucleotide corresponds to bases 189 to 473 of Genbank HSMYCC (accession number X00364). The base sequence of the polynucleotide is shown in SEQ ID NO: 1. However, it is easily understood by those skilled in the art that not only the base sequence of SEQ ID NO: 1, but also a mutant polynucleotide of the sequence of SEQ ID NO: 1, that is, a polynucleotide in which one or several bases are deleted, substituted, or added from/to the base sequence of SEQ ID NO: 1, is one of the preferable examples of the partial fragment of the IR including the DUE. Needless to say that the IR/MAR plasmid assembled with use of the mutant polynucleotide has an activity of amplifying the target gene.

Further, the partial fragment of the IR including the DUE can be a polynucleotide comprising a base sequence being obtained in such a manner that the base sequence of ID NO: 1 is searched on a database such as GenBank, EMBL, DDBJ, or the like via a homology search program such as BLAST N 2.2.1. Both the mutant polynucleotide and the polynucleotide obtained through the homology search are homologous with the polynucleotide of SEQ ID NO: 1 preferably by 80% or higher, more preferably approximately 90% or higher, and most preferably approximately 95% or higher.

Furthermore, of the IR derived from the c-myc locus as set forth in bases 1 to 2349 of Genbank HSMYCC (accession number X00364), a preferable example of the partial fragment of the IR including the topoisomerase II-binding domain is a polynucleotide that corresponds to bases 745 to 987 of Genbank HSMYCC (accession number X00364). The base sequence of the polynucleotide is shown in SEQ ID NO: 2. However, it is easily understood by those skilled in the art that not only the base sequence shown in SEQ ID NO: 2, but also a mutant polynucleotide of SEQ ID NO: 2, i.e., a polynucleotide in which one or several bases are deleted, substituted, or added from/to the base sequence of SEQ ID NO: 2, is one of the preferable examples of the partial fragment of the IR including the topoisomerase II-binding domain. For details of the mutant polynucleotide, refer to the foregoing description.

Moreover, a preferable example of the partial fragment of the IR including at least the DUE and topoisomerase II-binding domain is a polynucleotide corresponds to bases 189 to 987 of Genbank HSMYCC (accession number X00364). The base sequence of the polynucleotide is shown in SEQ ID NO: 3. However, it is easily understood by those skilled in the art that not only the base sequence shown in SEQ ID NO: 3, but also a mutant polynucleotide of SEQ ID NO: 3, i.e., a polynucleotide in which one or several bases are deleted, substituted, or added from/to the base sequence of SEQ ID NO: 3, is one of the preferable examples of the partial fragment. For details of the mutant polynucleotide, refer to the foregoing description.

Moreover, the inventors confirmed that, with regard to the IR derived from the DHFR, polynucleotides of base sequences shown in SEQ ID NOs: 11, 12, 13, 14, 15 and 16 correspond to the amplification-activating fragment. Based on the result, the inventors found that the target gene can be amplified when the polynucleotide including at least a polynucleotide of the base sequence of SEQ ID NO: 10 is used instead of the full-length IR of the IR/MAR plasmid. However, it is easily understood by those skilled in the art that not only the polynucleotide of SEQ ID NO: 10, but also a mutant polynucleotide of SEQ ID NO: 10, i.e., polynucleotide in which one or several bases are deleted, substituted, or added from/to the base sequence of SEQ ID NO: 10, can be used in the gene amplification method according to the present invention. For details of the mutant polynucleotide, refer to the foregoing description.

Examples of the amplification-activating fragment derived from the DHFR, the amplification-activating fragment including the polynucleotide of the base sequence of SEQ ID NO: 10 or the polynucleotide in which one or several bases are deleted, substituted, or added from/to the base sequence shown in SEQ ID NO: 10, are polynucleotides comprising base sequences of SEQ ID NOs: 11, 12, 13, 14, 15, and 16, and the mutant polynucleotides thereof. The amplification-activating fragment includes, like those derived from the c-myc locus, the DUE and topoisomerase II-binding domain. The amplification-activating fragment of the IR derived from DHFR further includes a bent DNA, a RIP60 binding domain, and an AT-rich element.

It was a remarkable finding that especially when the polynucleotide of the base sequence shown in SEQ ID NO: 11 was used, the amplification efficiency of the target gene was higher compared to the case where the full-length IR was used.

An example of the base sequence of the IR derived from DHFR is a base sequence as set forth in bases 1532 to 6166 of Genbank CFORIDHFR (accession number X94372).

The IR/MAR plasmid to be used in the transferring step of the gene amplification method according to the present invention may be selected from those including the above-mentioned amplification-activating fragment and MAR. However, the IR/MAR may also include: a sequence required for cloning within *Escherichia coli*; a drug resistance gene (blasticidin resistant gene, neomycin resistant gene, hygromycin resistant gene, and the like), a green fluorescence protein, or the like, as a selective marker (marker protein). The selective marker functions as an indicator so as to sort out a mammalian cell, to which the IR/MAR plasmid was transferred.

The target gene to be transferred in the transferring step of the gene amplification method according to the present invention is preferably connected controllably to a promoter. The promoter is not particularly limited and may be selected from those that function in the mammalian cell, to which the promoter is to be transferred. The promoter may be a promoter in which a transcription activity thereof can be activated or inactivated with a prescribed operation by a transcription factor etc. (In this Description, the promoter is referred to as "transcription activity-adjusting promoter"), and may be a homeostatic promoter in which the transcription activity is homeostatically activated. The "transcription activity-adjusting promoter" is not particularly limited and may be selected from those having the above characteristics. For example, commercially available products such as TRE promoter (Clontech Laboratories Inc.) and T-REX promoter (Invitrogen Corporation) are applicable in the method according to the present invention. Examples of the homeostatic promoter are a CMV promoter, a promoter derived from an SV40 early region (SV40 promoter), an SRalpha promoter (SRα promoter), an LTR promoter, an MMTV promoter, and the like.

In the transferring step of the gene amplification method according to the present invention, the IR/MAR plasmid and the target gene are concurrently transferred to the mammalian cell. By doing so, the target gene is highly amplified in the mammalian cell.

The mammalian cell is not particularly limited, and may be a CHO-K1 cell (Available from ATCC CCL-61, RIKEN RCB0285, RIKEN RCB0403 etc.), a tumor cell of every kind, or the like. However, especially preferable as the mammalian cell is a tumor cell having an infinite proliferation ability. Examples of the tumor cell are a HeLa cell (Available from ATCC CCL-2, ATCC CCL-2.2, RIKEN RCB0007, RIKEN RCB0191 etc.), human COLO 320DM tumor cell (Available from ATCC CCL-220 etc.), human COLO 320HSR tumor cell (Available from ATCC CCL-220.1), and NS0 cell (Available from RIKEN RCB0213). For details of the human COLO 320DM tumor cell, refer to "Shimizu, N., Kanda, T., and Wahl, G. M. Selective capture of acentricfragments by micronuclei provides a rapid method for purifying extrachromosomally amplified DNA. Nat. Genet., 12: 65-71, 1996.".

In transferring the IR/MAR plasmid and the target gene to the mammalian cell, the IR/MAR plasmid and the target gene may either be connected with each other so as to be transferred in the same gene construct, or be transferred respectively in different gene constructs, provided that both of them are concurrently transferred to the mammalian cell. Here, the former is referred to as arranging the IR/MAR plasmid and the target gene in cis, whereas the latter is referred to as arranging the IR/MAR plasmid and the target gene in trans. The former has such an advantage that operation is easy because what is to be done is just transferring a single gene construct to the mammalian cell. On the other hand, the latter makes it possible to decrease each gene construct in size, so that it becomes easier to achieve the above advantages (A) to (D).

Structure of the gene construct may either be a plasmid or a cosmid. Further, a method for transferring the IR/MAR plasmid and the target gene to the mammalian cell is not particularly limited, and may be selected from publicly known methods such as a lipofection, electroporation method, and particle gun method, as needed.

In the case where the IR/MAR plasmid and the target gene are transferred respectively in different gene constructs, each of them preferably includes a gene that encodes a selective marker. This is for selecting the mammalian cell to which the polynucleotide was transferred. Needless to say, it is preferable that the selective marker included in the IR/MAR plasmid be different from that included in the gene construct including the target gene.

[1-2. Selecting Step]

A "Selecting step" in the gene amplification method of the present invention is a step of isolating the mammalian cell, to which the target gene and the vector are transferred. More specifically, this step is a step of selecting, from a polyclonal cellular population including the mammalian cells to which neither target gene nor the vector is transferred and the mammalian cells to which the target gene and the vector are transferred, the mammalian cells to which the target gene and the vector are transferred. The selecting step may include a step of culturing the mammalian cells in a culture medium if the selecting step is carried out with use of a drug resistance as a marker. However, this step of culturing the mammalian cells in the selecting step is clearly different from a culturing step set forth below. This step of culturing in the selecting step is for culturing a cell mixture of the mammalian cells to which neither target gene nor the vector is transferred and the mammalian cells to which the target gene and the vector are transferred, whereas the hereinafter described step is for culturing the already-selected mammalian cells to which the target gene and the vector are transferred. The selecting step makes it possible to select the mammalian cells, in which the transferred target gene is highly amplified.

The selecting step is not particularly limited in more specific details, but for example, if the gene construct used in transferring the target gene and the vector into the mammalian cell includes a drug resistance gene, the drug resistance may be used for selecting the mammalian cells, to which the target gene and the vector are transferred.

Further, the selecting step in the method of the present invention for transferring a gene can be carried out also by detecting, through PCR or Southern blotting, the target gene or the vector, or a nucleotide fragment thereof, contained in the mammalian cell. The drug resistance, PCR, and Southern blotting are not particularly limited in more specific details, and may be adopted in a publicly known manner as needed.

[1-3. Culturing Step]

The "Culturing step" in the gene amplification method of the present invention is a step of culturing the mammalian cells, which have already been selected in the selecting step. The culturing step makes it possible to multiply the mammalian cells, in which the transferred gene is highly amplified, and to produce a target protein by a prescribed operation (e.g., transcription-inducing operation).

The culturing step is not particularly limited in more specific details, and may be carried out in any way in consideration of an optimum condition for the mammalian cells to be cultured.

[1-4. Purifying Step]

The "Purifying step" in the gene amplification method of the present invention is a step of purifying the target protein, which is produced in the culturing step.

More specifically, the protein purification in the purifying step comprises, for example, suspending the mammalian cells in a buffer solution such as a PBS (Phosphate Buffered Saline); breaking the cells with use of a homogenizer, ultrasonic wave, or the like; centrifugalizing the solution; and collecting a supernatant liquid. To the buffer solution, the followings may also be added as needed: a surfactant for promoting solubilization of the protein; a reducing agent for stabilizing a conformation of the protein; and a protease inhibitor for inhibiting degradation of the protein. Examples of the surfactant are a CHAPS (3-[(3-cholamidopropyl)-dimethylammonio-1-propanesulfonate]), Triton X-100, Nikkol, and n-octyl glucoside. Examples of the reducing agent are DTT (dithiothreitol) and DET (dithioerythritol). Examples of the protease inhibitor are aprotinin and leupeptine.

A protein (target protein), which the target gene encodes, can be purified from the supernatant liquid, with use of a column chromatography such as an affinity chromatography, ion exchanging chromatography, and filtration chromatography. It is also possible to remove unwanted salt by dialyzing the purified protein solution against an adequate buffer solution. The step for purifying the protein is carried out preferably at a low temperature in order to inhibit degradation of the protein. More preferably, the step is carried out preferably at a temperature of 4° C.

Note that the specific method of the purifying step is not subject to this limitation, and publicly known methods can be used as needed.

<2. Vector of the Present Invention>

The present invention further encompasses a vector for performing the above-mentioned gene amplification method of the present invention (hereinafter called "vector of the present invention"), or a gene amplification kit including the vector (hereinafter called "kit of the present invention").

For a description of the vector of the present invention, the description of the IR/MAR plasmid used in the gene amplification method of the present invention can be invoked.

Further, the kit of the present invention comprises the vector of the present invention. The kit according to the present invention is not particularly limited to the above configuration as long as the kit can perform the method according to the present invention, and may include other configurations. For the description of materials etc. that constitute the kit according to the present invention, the description of the method according to the present invention can be invoked as needed.

EXAMPLES

The present invention is more specifically described below based on examples, but is not limited to the examples. All the PCRs in the examples and reference examples were carried out with use of KOD polymerase (TOYOBO CO., LTD.). The PCRs were carried out under standard conditions described in an instruction provided with the KOD polymerase. A sequence of a primer is described later.

[Plasmids]

An IR gene in a DHFR locus Ori-β region and an IR gene in a c-myc (the IR genes have Asc I sites at 5' end and 3' end thereof) were produced in the following manner. An IR in the DHFR locus Ori-β region (4.6 kbp) was cleaved out from pSFVdhfr (described in "N. Shimizu, et al. (2001) Cancer Research, vol. 61, p 698'7-6990"), by restriction enzyme digestion using Not I. Further, an IR in the c-myc (2.4 kbp) was cleaved out from pNeo.Myc-2.4 (described in "McWhinney, C. et al., Nucleic Acids Res. Vol. 18, p 1233-1242 (1990)"), by restriction enzyme digestion using Not I and Hind III. Then, the two IR fragments had their 5' end and 3' end blunted, so that the blunt ends were ligated with adapter oligonucleotides having a restriction enzyme site of Asc I.

Further, plasmids described in "N. Shimizu, et al. (2001) Cancer Research, vol. 61, p 698'7-6990" were used and referred to as pΔBN.AR1, pΔBN.polyA, and pSFV-V.

Furthermore, pΔH was produced in such a manner that a hygromycin-resistant gene cassette of full length contained in pSFV-V was removed with use of restriction enzymes Not I and Nru I, and instead, a synthetic oligonucleotide containing a multi cloning site was inserted to the site where the gene cassette used to be located. The restriction enzyme sites of the multi cloning site are located downstream of a blasticidin resistant gene (hereinafter called "BSR"), wherein they are arranged in order of Kpn I-Not I-Asc I-Nru I, in a direction from 5' end toward 3' end.

Moreover, pΔHpA illustrated in FIG. 3D was produced in such a manner that a gene containing an HSV poly A sequence (1357 bp) was amplified through PCR with use of a primer set of HSVpAKpnIR and HSVpAKpnIL, which have been designed so that the restriction enzyme site of Kpn I is to be added to 5' end and 3' end thereof, and then thus amplified gene was inserted to the Kpn I site of the pΔH with use of the restriction enzyme site of Kpn I. Base sequences of the primers HSVpAKpnIR and HSVpAKpnIL are shown in SEQ ID NOs: 17 and 18, respectively. Also, the base sequence of the HSV poly A sequence is shown in SEQ ID NO: 19.

pΔHpAdhfr illustrated in FIG. 3E was produced in such a manner that the IR of the DHFR locus Ori-β region produced above was inserted to Asc I site of pΔHpA, in a way that a MAR sequence being present inside the IR fragment is located farther away than a transcription initiation point of the BSR.

Figure 3:
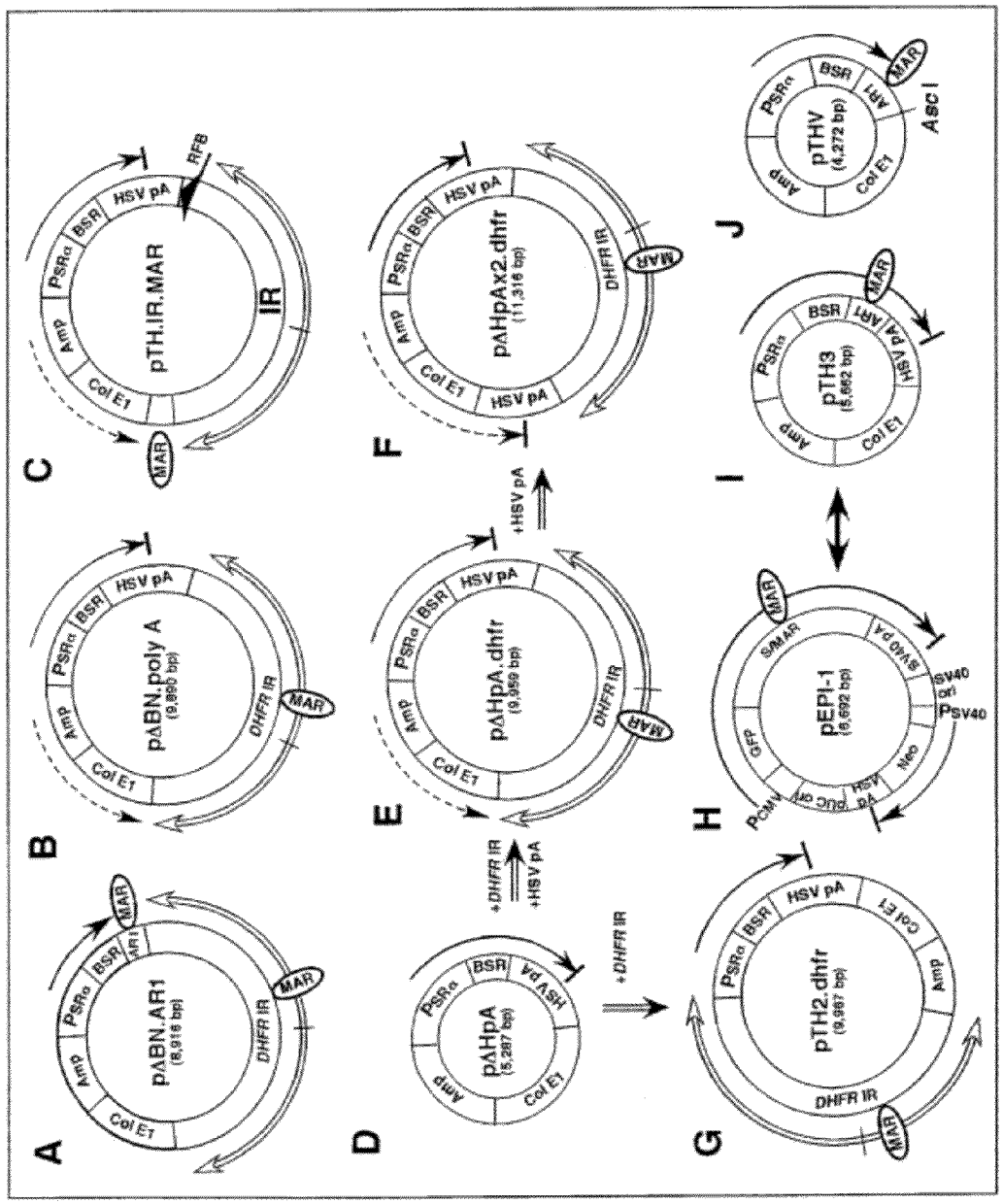
FIG. 3 is a schematic view of plasmids used in Examples and Reference Examples.

Further, pΔHpA×2.dhfr illustrated in FIG. 3F was produced in such a manner that a gene fragment containing the HSV poly A sequence (indicated with "HSV pA" in FIG. 3) having both ends blunted was inserted to Nru I site of the pΔHpA.dhfr.

Furthermore, pTH.IR.MAR in FIG. 3C was produced through the following steps:

(i) An MAR (375 bp) fragment of AR1 was cleaved out from pAR1 by restriction enzyme digestion using Hind III and BamH I, and then both ends of the fragment were blunted. Details of the pAR1 are described in "N. Shimizu, et al. (2001) Cancer Research, vol. 61, p 6987-6990".

(ii) With use of pNeo.Myc-2.4 as a template, a primer set of SV40L and SV40R was used to perform PCR, through which an MAR gene of an early region of SV40 was obtained. Base sequences of the SV40L and SV40R are shown in SEQ ID NOs: 20 and 21, respectively. Further, a base sequence of the MAR gene of the early region of SV40 is shown in SEQ ID NO: 22.

(iii) With use of pSV2.5B2 as a template, a primer set of RFB Not IL and RFB Not IR, which have been designed so that the restriction enzyme Not I is added to 5' end and 3' end, was used to perform the PCR, through which a gene (118 bp) containing a RFB (replication fork barrier) sequence was obtained. Since the RFB sequence blocks formation of a replication fork, the RFB sequence can inhibit replication of a plasmid to which the RFB sequence was transferred. Base sequences of RFB Not IL and RFB Not IR are shown in SEQ ID NOs: 23 and 24, respectively. Further, a base sequence of RFB sequence is shown in SEQ ID NO: 25.

(vi) The gene containing the RFB sequence was inserted to Not I site of pΔHpA in a way that the replication fork arriving from the IR is blocked. Next, MAR genes of the AR1 and SV40, both of which have their ends blunted, were inserted to Nru I site of the plasmid.

(v) Finally, the IR gene of the c-myc or the IR gene of the DHFR locus Ori-β region, which has been produced above, and the gene made in such a manner that a fragment (4361 bp) produced through restriction enzyme digestion with Hind III of λ-phage, and ligated with Asc I site at both ends, were inserted to Asc I site of the plasmid produced in the step (vi).

Furthermore, pTH2.dhfr illustrated in FIG. 3G and pTH2.dhfr.inv were produced in such a manner that the above-produced IR gene (4.6 kbp) of the DHFR locus Ori-β region, the IR gene having both ends blunted, was inserted to pΔHpA (which has been digested with Eco R I and had both ends blunted) in a direction of BSR transcription and in a direction against the BSR transcription, respectively.

Note that, pEPI-I ("Schaarschmidt, D., Baltin, J., Stehle, I. M., Lipps, H. J., and Knippers, R. (2004) EMBO J. 23(1), 191-201.", and "Jenke, A. C., Stehle, I. M., Herrmann, F., Eisenberger, T., Baiker, A., Bode, J., Fackelmayer, F. O., and Lipps, H. J. (2004) Proc. Natl. Acad. Sci. USA 101, 11322-11327.") illustrated in FIG. 3H was provided by Mr. Daniel Schaarchmidt (Department of Biology, Universitat of Konstanz).

Moreover, pTHV illustrated in FIG. 3J was produced in such a manner that the MAR of AR1 was inserted to Kpn I site of pΔH through a blunt-end ligation.

Moreover, pTH3 illustrated in FIG. 3I was produced in such a manner that the HSV poly A sequence was inserted to Not I site of the pTHV through a blunt-end ligation.

Furthermore, the vector containing a partial fragment (C0 to C16) of the c-myc IR (2.4 kbp) or a partial fragment (D1 to D11) of the IR of the DHFR locus Ori-β region (4.6 kbp) was produced in such a manner that the gene, which was amplified through the PCR with use of pNeo.Myc-2.4 and pSFVdhfr as templates, was inserted to Asc I site of the pTHV.

Base sequences of 5' primer (C0-5') and 3' primer (C0-3'), for amplifying C0, which were used in the PCR, are shown in SEQ. ID. NOs: 26 and 27, respectively. Base sequences of 5' primer (C1-5') and 3' primer (C1-3'), for amplifying C1, are shown in SEQ ID NOs: 28 and 29, respectively. Base sequences of 5' primer (C2-5') and 3' primer (C2-3'), for amplifying C2, are shown in SEQ ID NOs: 30 and 31, respectively. Base sequences of 5' primer (C3-5') and 3' primer (C3-3'), for amplifying C3, are shown in SEQ ID NOs: 32 and 33, respectively. Base sequences of 5' primer (C4-5') and 3' primer (C4-3'), for amplifying C4, are shown in SEQ ID NOs: 34 and 35, respectively. Base sequences of 5' primer (C5-5') and 3' primer (C5-3'), for amplifying C5, are shown in SEQ ID NOs: 36 and 37, respectively. Base sequences of 5' primer (C6-5') and 3' primer (C6-3'), for amplifying C6, are shown in SEQ ID NOs: 38 and 39, respectively. Base sequences of 5' primer (C7-5') and 3' primer (C7-3'), for amplifying C7, are shown in SEQ ID NOs: 40 and 41, respectively. Base sequences of 5' primer (C8-5') and 3' primer (C8-3'), for amplifying C8, are shown in SEQ ID NOs: 42 and 43, respectively. Base sequences of 5' primer (C9-5') and 3' primer (C9-3'), for amplifying C9, are shown in SEQ ID NOs: 44 and 45, respectively. Base sequences of 5' primer (C10-5') and 3' primer C10-3'), for amplifying C10, are shown in SEQ ID NOs: 46 and 47, respectively. Base sequences of 5' primer (C11-5') and 3' primer C11-3'), for amplifying C11, are shown in SEQ ID NOs: 48 and 49, respectively. Base sequences of 5' primer (C 12-5') and 3' primer C12-3'), for amplifying C12, are shown in SEQ ID NOs: 50 and 51, respectively. Base sequences of 5' primer (C 13-5') and 3' primer C13-3'), for amplifying C13, are shown in SEQ ID NOs: 52 and 53, respectively. Base sequences of 5' primer (C 14-5') and 3' primer C14-3'), for amplifying C14, are shown in SEQ ID NOs: 54 and 55, respectively. Base sequences of 5' primer (C15-5') and 3' primer C15-3'), for amplifying C15, are shown in SEQ ID NOs: 56 and 57, respectively. Base sequences of 5' primer (C16-5') and 3' primer (C16-3'), for amplifying C16, are shown in SEQ ID NOs: 58 and 59, respectively. Base sequences of 5' primer (D1-5') and 3' primer (D1-3'), for amplifying D1, are shown in SEQ ID NOs: 60 and 61, respectively. Base sequences of 5' primer (D2-5') and 3' primer (D2-3'), for amplifying D2, are shown in SEQ ID NOs: 62 and 63, respectively. Base sequences of 5' primer (D3-5') and 3' primer (D3-3'), for amplifying D3, are shown in SEQ ID NOs: 64 and 65, respectively. Base sequences of 5' primer (D4-5') and 3' primer (D4-3'), for amplifying D4, are shown in SEQ ID NOs: 66 and 67, respectively. Base sequences of 5' primer (D5-5') and 3' primer (D5-3'), for amplifying D5, are shown in SEQ ID NOs: 68 and 69, respectively. Base sequences of 5' primer (D6-5') and 3' primer (D6-3'), for amplifying D6, are shown in SEQ ID NOs: 70 and 71, respectively. Base sequences of 5' primer (D7-5') and 3' primer (D7-3'), for amplifying D7, are shown in SEQ ID NOs: 72 and 73, respectively. Base sequences of 5' primer (D8-5') and 3' primer (D8-3'), for amplifying D8, are shown in SEQ ID NOs: 74 and 75, respectively. Base sequences of 5' primer (D9-5') and 3' primer (D9-3'), for amplifying D9, are shown in SEQ ID NOs: 76 and 77, respectively. Base sequences of 5' primer (D10-5') and 3' primer (D10-3'), for amplifying D10, are shown in SEQ ID NOs: 78 and 79, respectively. Base sequences of 5' primer (D11-5') and 3' primer (D11-3'), for amplifying D11, are shown in SEQ ID NOs: 80 and 81, respectively. Further, a base sequence of C0 having been amplified through the PCR is shown in SEQ ID NO: 82. A base sequence of C1 having been amplified through the PCR is shown in SEQ ID NO: 83. A base sequence of C2 having been amplified through the PCR is shown in SEQ ID NO: 84. A base sequence of C3 having been amplified through the PCR is shown in SEQ ID NO: 85. A base sequence of C4 having been amplified through the PCR is shown in SEQ ID NO: 86. A base sequence of C5 having been amplified through the PCR is shown in SEQ ID NO: 87. A base sequence of C6 having been amplified through the PCR is shown in SEQ ID NO: 88. A base sequence of C7 having been amplified through the PCR is shown in SEQ ID NO: 89. A base sequence of C8 having been amplified through the PCR is shown in SEQ ID NO: 90. A base sequence of C9 having been amplified through the PCR is shown in SEQ ID NO: 91. A base sequence of C10 having been amplified through the PCR is shown in SEQ ID NO: 92. A base sequence of C11 having been amplified through the PCR is shown in SEQ ID NO: 93. A base sequence of C12 having been amplified through the PCR is shown in SEQ ID NO: 94. A base sequence of C13 having been amplified through the PCR is shown in SEQ ID NO: 95. A base sequence of C14 having been amplified through the PCR is shown in SEQ ID NO: 96. A base sequence of C15 having been amplified through the PCR is shown in SEQ ID NO: 97. A base sequence of C16 having been amplified through the PCR is shown in SEQ ID NO: 98. A base sequence of D1 having been amplified through the PCR is shown in SEQ ID NO: 99. A base sequence of D2 having been amplified through the PCR is shown in SEQ ID NO: 100. A base sequence of D3 having been amplified through the PCR is shown in SEQ ID NO: 101. A base sequence of D4 having been amplified through the PCR is shown in SEQ ID NO: 102. A base sequence of D5 having been amplified through the PCR is shown in SEQ ID NO: 103. A base sequence of D6 having been through the PCR is shown in SEQ ID NO: 104. A base sequence of D7 having been amplified through the PCR is shown in SEQ ID NO: 105. A base sequence of D8 having been amplified through the PCR is shown in SEQ ID NO: 106. A base sequence of D9 having been amplified through the PCR is shown in SEQ ID NO: 107. A base sequence of D10 having been amplified through the PCR is shown in SEQ ID NO: 108. A base sequence of D 11 having been amplified through the PCR is shown in SEQ ID NO: 109.

Method of Experiment

The following experiments were carried out by using the plasmids produced as above.

In the present example and reference example (collectively called "examples"), gene transfer was carried out by transferring the plasmid to a cell; the cell being transformed by the plasmid was selected; and frequency of HSR formation inside the transformed cell was analyzed by FISH.

A gene transfer method used in the present example is described below. First, the plasmid to be used for the gene transfer was purified from *Escherichia coli*, by using Qiagen plasmid purifying kit (Qiagen Inc., Valencia, Calif.). Because the DNA purification could not separate an *Escherichia coli*-derived endotoxin from the plasmid, the *Escherichia coli*-derived endotoxin was removed from the plasmid, by using MiraCLEAN (registered trademark) endotoxin removal kit (Mirus., Madison, Wis.). Then, in accordance with a method recommended by a maker, the plasmid was transferred to a cell by using GenePorter (registered trademark) 2 lipofection kit (Gene Therapy Systems, San Diego, Calif.), thereby a gene was transferred.

The above cell, to which the gene was to be transferred, was a COLO 320DM or COLO 320HSR, which is a human colon cancer cell strain, or a Hela, which is a human cervix cancer cell strain. The cell strain was obtained from a site described in "N. Shimizu, et al. (2001) Cancer Research, vol. 61, p 6987-6990", and then cultured under the same condition as set forth in the "N. Shimizu, et al. (2001) Cancer Research, vol. 61, p 6987-6990". A large amount of endogenous DMs have been generated in the COLO 320DM due to amplification of the c-myc gene, whereas more HSRs have been generated than DMs in the COLO 320HSR, which is an isogenic line of the COLO 320DM.

Transformed cells were selected by culturing the transformed cells in a selection medium, to which blasticidin was added so that blasticidin reached its final concentration of 5 μg/ml in two days after the gene transfer. A half of the selection medium in culture was replaced with a newly-prepared selection medium every 3 to 5 days.

The above-mentioned FISH; preparation of a probe for detecting the transferred genes to be used in FISH; and a metaphase spreading, were carried out as described in "N. Shimizu, et al. (2001) Cancer Research, vol. 61, p 6987-6990", by collecting some of the cells in culture after 4, 6, and 8 weeks of incubation, respectively. Since the probe has been biotinylated, the probe can be detected by streptavidin, to which FITC (fluorescein isothiocyanate) that emits green fluorescence is bound. Further, a DNA was counterstained with PI (propidium iodide) that emits red fluorescence. The cells fluorescently-labeled by FISH were placed on a glass slide and observed through an inverted fluorescence microscope (ECLIPSE TE2000-U, Nikon) including a suitable filter set for detecting fluorescence dye and a 100× objective lens (Nikon Plan Fluor, NA1.30 oil), and then aspects of the transferred genes and the DNAs inside the cells were photographed as digital images, by using Fuji FinePix S1Pro digital camera (Fuji Film Co. Tokyo) being connected to the above microscope. Thus obtained images were combined by using an image analysis software Adobe (registered trademark) Photoshop (registered trademark) version 4.0J (Adobe Systems Inc).

Reference Example 1

A plasmid pSFVdhfr, pΔHpA×2.dhfr, pTH2.dhfr, or pEPI-I was transferred to a COLO 320DM, thereby a gene was transferred. Transformed cells were collected after 6 weeks of incubation, except for the case where the pSFVdhfr was transferred. In the case where the pSFVdhfr was transferred, the transformed cells were collected after 8 weeks of incubation. On each of the collected cells, DMs and HSRs were detected by FISH.

Figure 2:
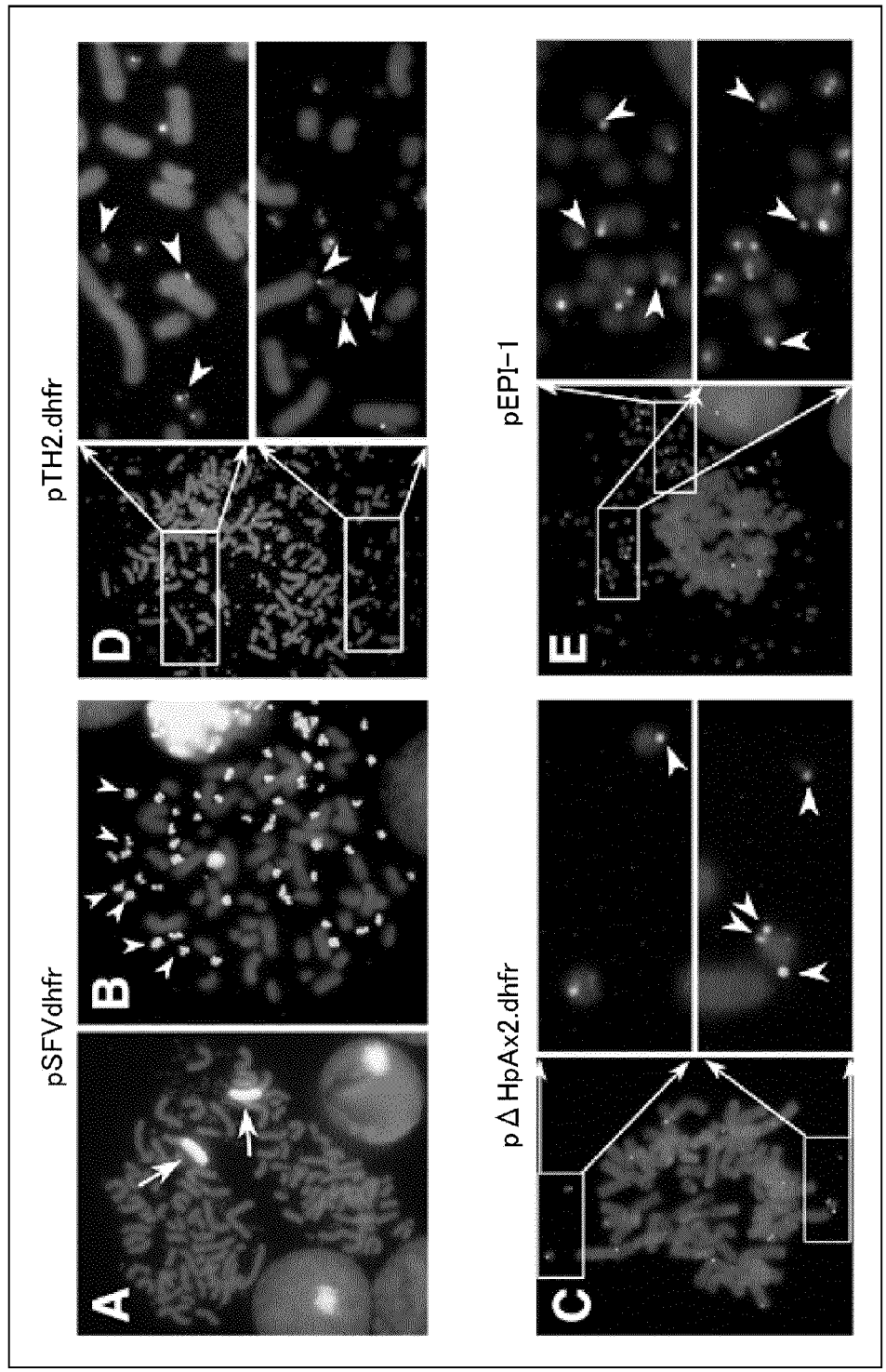
FIG. 2 shows fluorescent microscopy images of the DM and HSR generated in a COLO 320DM having been transformed by a vector, the DM and HSR being detected by FISH.
Figure 4:
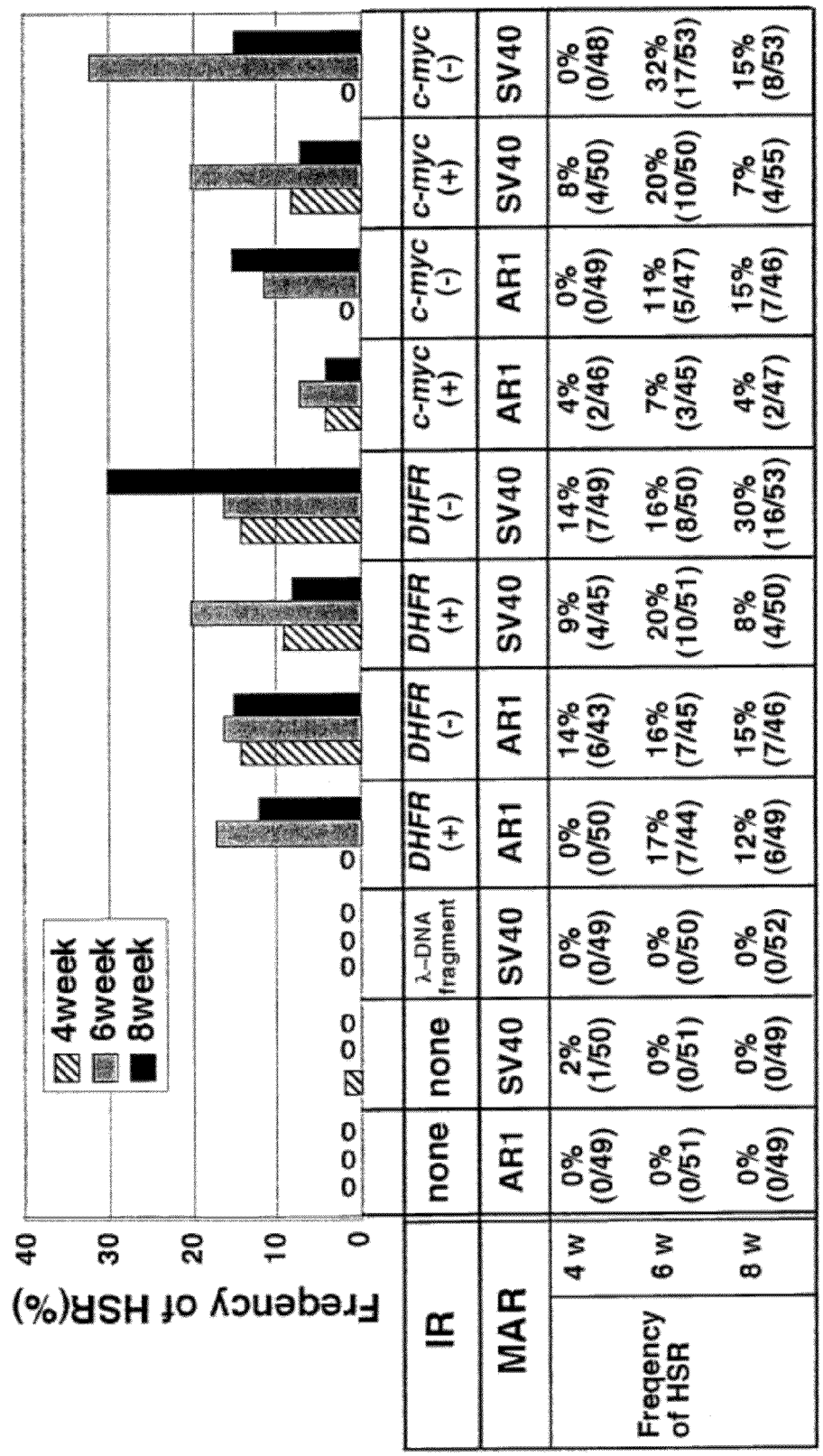
FIG. 4 is a bar chart showing frequencies of HSR generated in the COLO 320DM, to which pTH.IR.MAR plasmids were respectively transferred, in Reference Example 1.

FIG. 2 shows results of detecting the DMs and HSRs by FISH. FIGS. 2A and 2B show the result on the transformed cells to which the pSFVdhfr was transferred, FIG. 2C shows the result on the transformed cells to which the pΔHpA×2.dhfr was transferred, FIG. 2D shows the result on the transformed cells to which the pTH2.dhfr was transferred, and FIG. 2E shows the result on the transformed cells to which the pEPI-I was transferred. In FIG. 2, arrowheads and arrows indicate the DMs and HSRs, respectively.

pTH.IR.MAR containing a variety of combinations of an IR and MAR was produced and transferred to the COLO 320DM, thereby a gene was transferred, and then transformed cells were collected after 4, 6, or 8 weeks of incubation. The HSRs having been generated in the transformed cells were analyzed by FISH, so as to calculate frequency of HSR. A result thereof is shown in FIG. 4. The frequency of HSR was calculated by using a formula "(the number of transformed cells in which the HSR has been generated÷the number of transformed cells)×100". In FIG. 4, "(+)" and "(−)" in "IR" line indicate the cases where the IR was in the same direction as BSR transcription and where the IR was in the direction against the BSR transcription, respectively. Further, "λ-DNA fragment" indicates that a gene fragment of λ phage (4361 bp) was integrated instead of IR, whereas "none" indicates that no IR was contained.

FIG. 4 shows that HSR was generated only in the transformed cell, to which the plasmid including the IR and MAR was transferred, thereby a gene was transferred. FIG. 4 further suggested that the IR has a base sequence having an activity of generating HSR, since only a few HSRs were generated in the cases where the gene fragment of λ phage (4361 bp) was used instead of IR and where no IR was used.

A plasmid (pΔBN.AR1, pΔHpA, pΔHpA.dhfr, pΔHpA×2.dhfr, pTH2.dhfr, pTH2.dhfr.inv, pEPI-1, or pTH3) was transferred to a HeLa, COLO 320HSR, or COLO 320DM, thereby a gene was transferred. After the gene transfer, transformed cells were selected by culturing for 4 or 8 weeks in a selection medium. Then, frequency of HSR on the transformed cells selected was analyzed. A result thereof is shown in FIG. 5.

Figure 5:
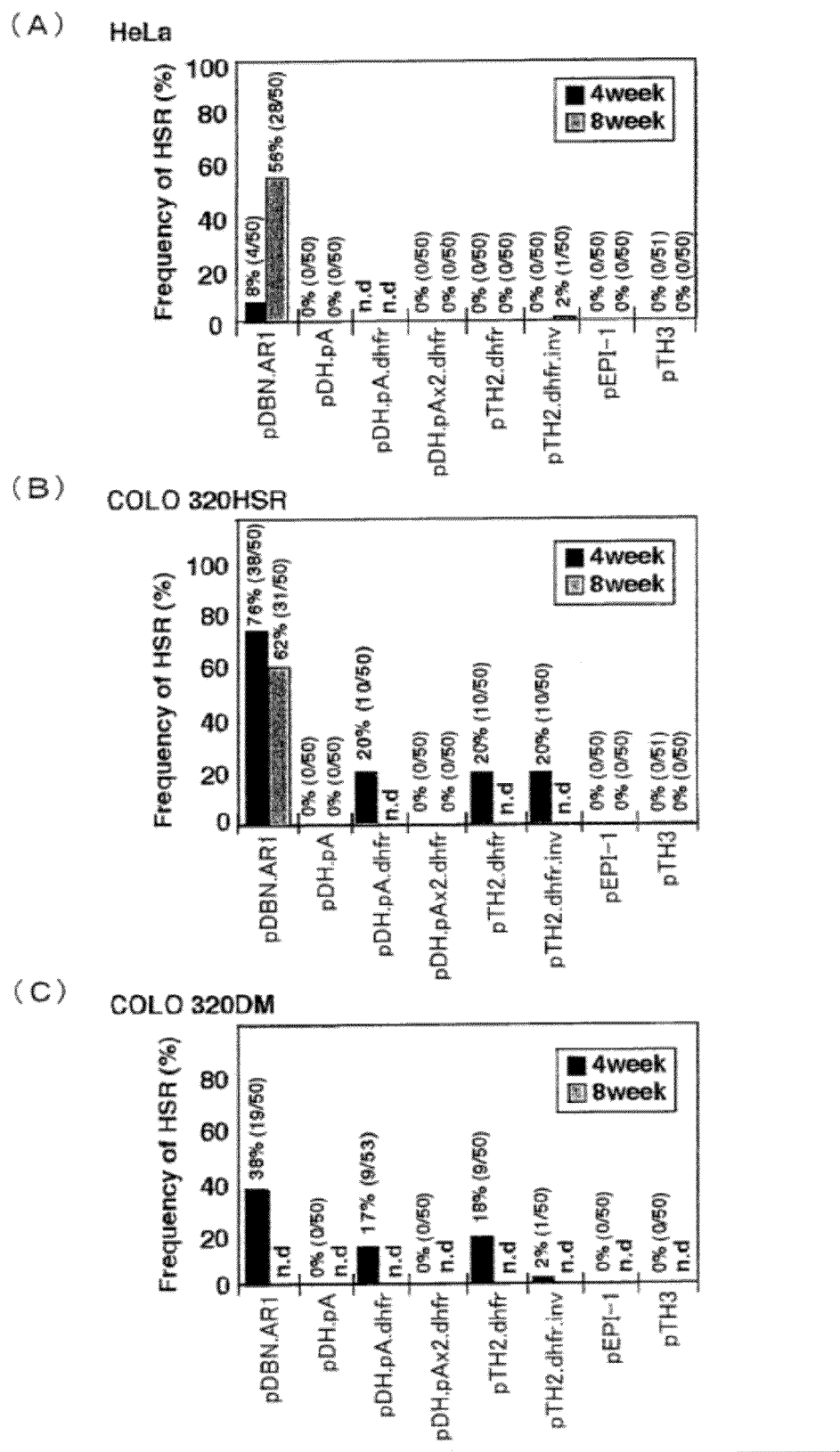
FIG. 5 are bar charts showing frequencies of HSR on a Hela (FIG. 5A), COLO 320HSR (FIG. 5B), and COLO 320DM (FIG. 5C), to which plasmids (pΔBN.AR1, pΔHpA, pΔHpA.dhfr, pΔHpAx2.dhfr, pTH2.dhfr, pTH2.dhfr.inv, pEPI-1, and pTH3) were transferred respectively.

FIG. 5 shows that HSR was generated in the case where gene transfer was carried out with pΔHpA.dhfr produced so that collision occurred between a gene replication and noncoding transcription. On the other hand, no HSR was generated in the case where the gene transfer was carried out with pΔHpA×2.dhfr produced by adding a poly A sequence so that the collision between the noncoding transcription and the gene replication would not occur. This suggests that the collision between the gene replication and the noncoding transcription affects stability of the plasmid, thereby causing a multimerization of the plasmid, and this triggers HSR generation. Further, HSR was generated, though the frequency was low, in the case where the gene transfer was carried out with pTH2.dhfr produced so that the collision between the noncoding transcription and the gene replication would not occur. This suggests that the collision between the gene replication and noncoding transcription occurred. These results revealed that the collision between the gene replication and the noncoding transcription can be inhibited by adding the poly A sequence to both ends of IR.

In addition, according to a literature "Jenke, A. C., Stehle, I. M., Herrmann, F., Eisenberger, T., Baiker, A., Bode, J., Fackelmayer, F. O., and Lipps, H. J. (2004) Proc. Natl. Acad. Sci. USA 101, 11322-11327.", the MAR being inserted between transcriptional regions is essential for maintaining the gene replication and a mammalian episome, and IR is not necessary. In view of this, a plasmid (pEPI-1) used in this literature and a plasmid (pTH3) of a same structure as the pEPI-1 were produced. The pTH3 is a plasmid in which an MAR derived from AR1 is present inside a BSR transcriptional region. Gene transfer was carried out by transferring the plasmid to a HeLa, COLO 320HSR, or COLO 320DM, and then the frequency of HSR therein was analyzed. It was found that neither HSR nor DM was generated in the transformed cell. On the other hand, submicroscopic episomes were observed. This suggests that IR is essential for generation of the HSR. In addition, since IR relates to the gene replication and HSR relates to the gene amplification, it is considered that the gene replication of the IR and the gene amplification are related with each other.

Example 1

Identification of a partial fragment of a c-myc locus IR, the partial fragment having a gene amplification activity, was carried out. That is, the partial fragment (C0 to C16) of the c-myc locus IR produced through PCR was inserted to Asc I site of pTHV (FIG. 3J) so as to produce a plasmid (pC0 to pC16) including the partial fragment (C0 to C16) (see Plasmids section).

Then, each plasmid is transferred to a cell. If the integrated partial fragment has the gene amplification activity, a collision will then occur between a replication and transcription in MAR area, thereby an HSR is generated in a transformed cell that has been transformed by the plasmid. On the other hand, if the integrated partial fragment has no gene amplification activity, no HSR will be then generated in the transformed cell. By utilizing this phenomenon, identification of the partial fragment of the c-myc locus IR, the partial fragment having the gene amplification activity, was carried out. For convenience of the description hereinafter, the above identification method is referred to as "plasmid stabilization analysis method".

The pC0 to pC16 were transferred to a COLO 320DM. In addition, a plasmid (pCf.1) containing a full-length c-myc IR was transferred to the COLO 320DM, as a positive control, whereas a plasmid (pTHV) containing no c-myc IR was transferred to the COLO 320DM, as a negative control. The COLO 320DMs were cultured for 6 weeks in a selection medium, so as to obtain transformed cells. On the transformed cells thus obtained, frequency of HSR was analyzed by the method as described above.

Figure 6:
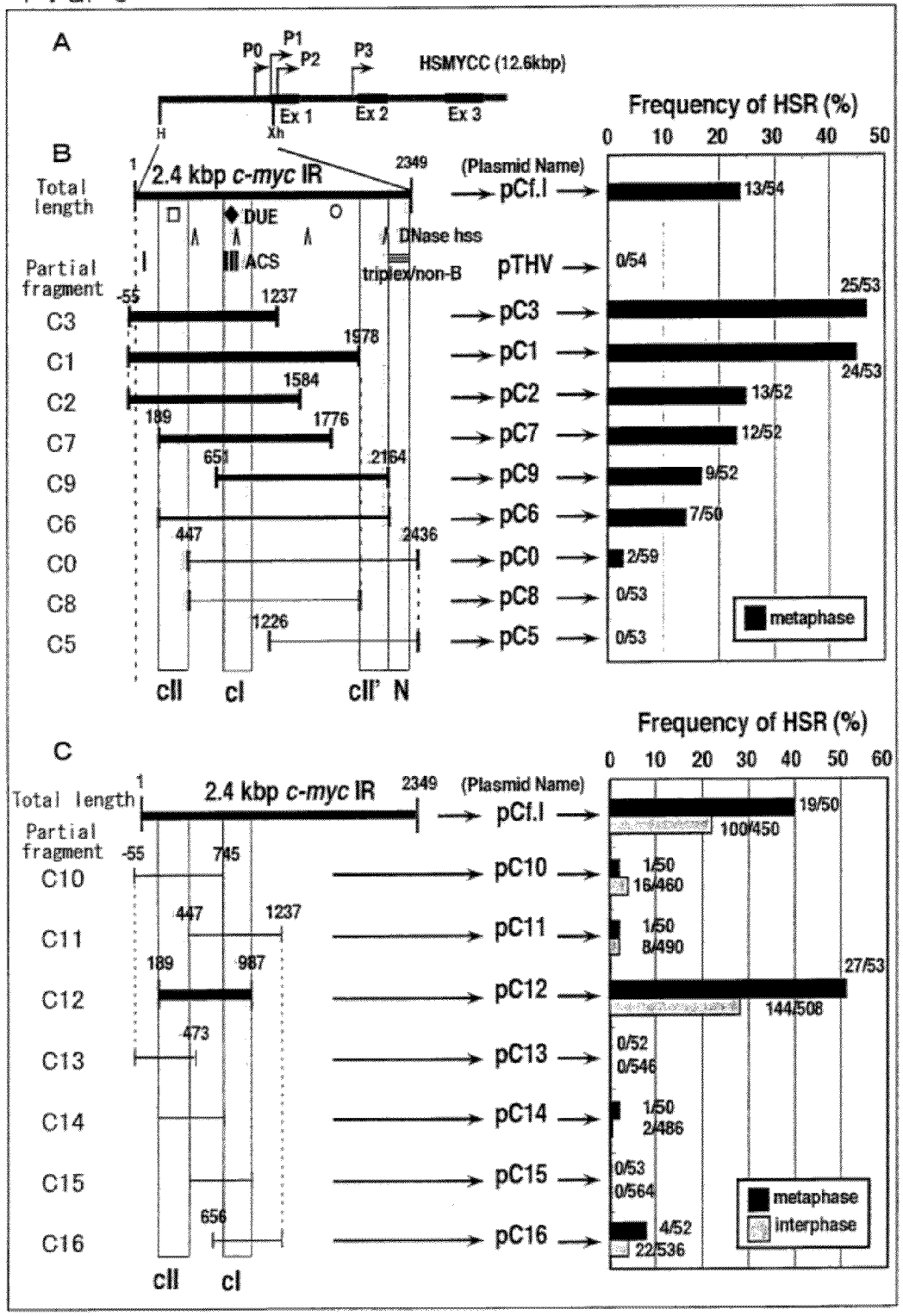
FIG. 6 is a view showing a result of Example 1.

A result is shown in FIG. 6. FIG. 6A is a schematic view of the c-myc locus (Genbank HSMYCC; accession number X00364). The c-myc locus IR corresponds to a Hind III-Xho I fragment (2349 bp) of the c-myc locus. FIGS. 6B and 6C show a positional relation between the c-myc IR of full-length and a partial fragment thereof (C0 to C16), and frequency of HSR in the transformed cell to which each partial fragment was transferred. Further, in FIG. 6, "□ (unfilled square)" indicates a position of a topoisomerase II-binding domain on the c-myc locus, "♦ (filled lozenge)" indicates a position of a Duplex Unwinding Element (DUE), and "○ (unfilled circle)" indicates a position of a sequence, which corresponds to a core 20 bp within a human consensus sequence of 36 bp. It has been reported that the core 20 bp within a human consensus sequence of 36 bp supports a self-replication of a plasmid. Furthermore, "cI" indicates a position of a base sequence having the gene amplification activity, the base sequence including a Duplex Unwinding Element (DUE); "cII" indicates a position of a base sequence having the gene amplification activity, the base sequence including a topoisomerase II-binding domain; "cII'" indicates a position of a sequence similar to the CII; and "N" indicates a position of a negative domain (a domain for inhibiting HSR formation).

FIG. 6B demonstrates that a highest frequency of HSR was observed in the transformed cell to which the pC3 was transferred, and the frequency was higher than in the positive control. Further, a highest frequency of HSR was observed in the transformed cell to which the pC1 was transferred, the frequency was higher than that of the positive control. Furthermore, the frequency of HSR in the transformed cell to which the pC2 or pC7 was transferred, was equivalent to that of the positive control. Moreover, the HSR generation was observed in the transformed cell to which the pC9 or pC6 was transferred.

Further, another partial fragment was produced from the partial fragment of the c-myc IR being inserted in the pC3, so as to analyze the frequency of HSR. FIG. 6C shows a result thereof showing that the highest frequency of HSR observed in the transformed cell, to which the plasmid (pC12) including the partial fragment that contains the topoisomerase II-binding domain and Duplex Unwinding Element (DUE) was transferred. The frequency of HSR was higher than that of the positive control. On the other hand, it was found that no HSR was formed or the frequency of HSR was extremely low on the transformed cell, to which the partial fragment that lacks one of the topoisomerase II-binding domain and Duplex Unwinding Element (DUE) was transferred. This explained that both the topoisomerase II-binding domain and Duplex Unwinding Element (DUE) are essential elements for the gene amplification. In addition, it was newly found that the use of the partial fragment including both the topoisomerase II-binding domain and the Duplex Unwinding Element (DUE) makes the frequency of HSR higher, even higher than the case where the full-length IR is used.

Example 2

Identification of a partial fragment of a DHFR locus Ori-β region IR, the partial fragment having a gene amplification activity, was carried out in the same way as Example 1, except that the DHFR locus Ori-β region IR was used instead. That is, a partial fragment (D1 to D11) of the DHFR locus Ori-β region IR produced through PCR was inserted to Asc I site of pTHV (FIG. 3J) so as to produce a plasmid (pD1 to pD11) including the partial fragment (D1 to D11) (see Plasmids section). A plasmid ("pDf.l") containing a full-length DHFR locus Ori-β region IR was employed as a positive control, whereas a plasmid ("pTHV") containing no DHFR locus Ori-β region IR was employed as a negative control.

A result of the example is shown in FIG. 7. FIG. 7 shows a schematic view of the DHFR locus Ori-β region (Genbank CFORIDHFR; accession number X94372), wherein a BamHI-Hind III fragment (4.6 kbp) of the DHFR locus Ori-β region corresponds to the DHFR locus Ori-β region IR. FIG. 7 further shows a positional relation between the DHFR locus Ori-β region IR of full length and a partial fragment thereof (D0 to D11), and frequency of HSR in a transformed cell to which each partial fragment was transferred.

FIG. 7 shows that no HSR was generated in the transformed cell, to which the plasmid (pD6 and pD7) including a partial fragment that lacks 3142nd region of the DHFR locus Ori-β region (Genbank CFORIDHFR; accession number X94372) was transferred. Further, frequency of HSR significantly decreased in the transformed cell, to which the plasmid (pD5 and pD10) including a partial fragment that lacks 4885th region of the DHFR locus Ori-β region (Genbank CFORIDHFR; accession number X94372) was transferred. This explained that the 3142nd to 4885th regions in the DHFR locus Ori-β region (Genbank CFORIDHFR; accession number X94372) are essential for generation of the HSR. These regions include a topoisomerase II-binding domain (□ (unfilled square) in FIG. 7) and Duplex Unwinding Element (DUE, ♦ (filled lozenge) in FIG. 7). Therefore, the result of Example 2 suggests that, together with the result of Example 1, the partial fragment of the IR, the partial fragment including the topoisomerase II-binding domain and Duplex Unwinding Element (DUE), has the gene amplification activity. The base sequences of regions further include a bent DNA (=(double line) in FIG. 7), RIP60 binding domain (Δ (unfilled triangle) in FIG. 7), and AT-rich element ("AT" in FIG. 7). By comparing the frequency of HSR in the transformed cell to which the pD6 or pD7 was transferred, to that of the transformed cell to which the pD1 was transferred, it was found that the three elements (bent DNA, RIP60 binding domain, and AT-rich element) are also essential for the generation of HSR, with regard to the DHFR locus Ori-β region.

Example 3

Figure 8:
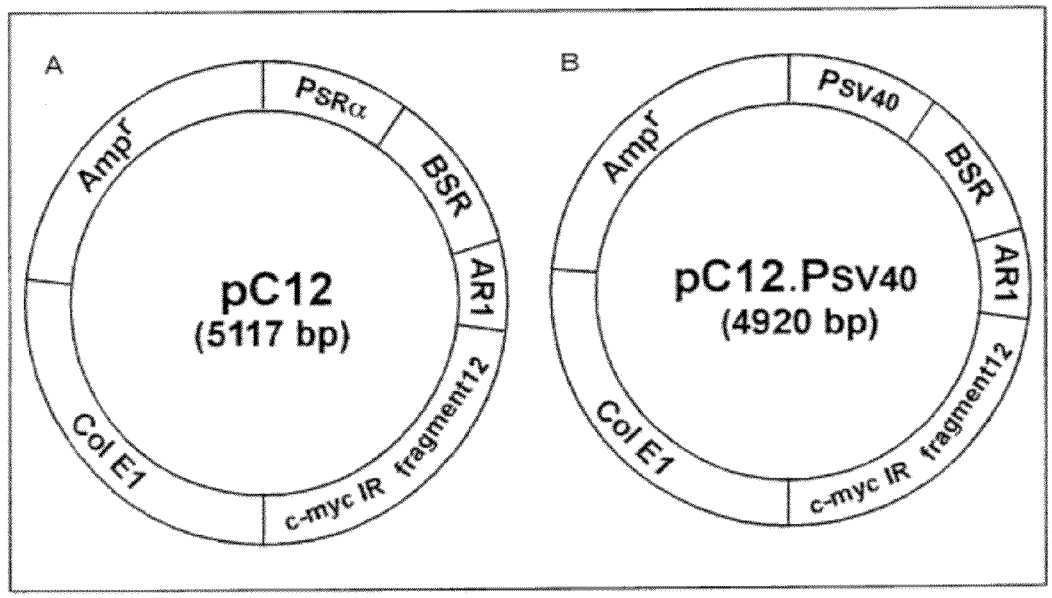
FIG. 8A is a schematic view showing a pC12 vector that was used in Examples.
FIG. 8B is a schematic view showing a pC12.Psv40 vector that was used in Examples.

A plasmid used in this example was pC12.Psv40 (FIG. 8B), in which an SRα promoter ("PSRα" in FIG. 8A) in pC12 (FIG. 8A) used in Example 1 was substituted with a promoter region derived from an SV40 early region (hereinafter merely called "SV40 promoter"). In FIG. 8B, the SV40 promoter is indicated as "Psv40". The pC12.Psv40 was prepared as follows.

First, an SRα promoter region was cleaved out by performing a restriction enzyme digestion on the pC12 with Eco RI and Xho I. A synthetic oligonucleotide (ESMX linker) containing a multi-cloning site was inserted into the cleaved-out region. Restriction enzyme sites of the multi-cloning site are located downstream of an ampicillin-resistant gene (Amp$^R$) (i.e., an area where the SRα promoter used to be located), wherein the restriction enzyme sites are arranged in order of Eco RI-Sal I-Mlu I-Xho I, in a direction from 5' end toward 3' end. A base sequence of an ESMX linker is shown in Table 1, and SEQ ID NO: 110 and SEQ ID NO: 111. Thus produced plasmid was subjected to a restriction enzyme digestion with Sal I and Mlu I. Thereafter, the SV40 promoter having been subjected to the restriction enzyme digestion with Sal I and Mlu I was inserted into the above described plasmid, so as to assemble the pC12.Psv40. The SV40 promoter was inserted in a direction of BSR transcription.

The SV40 promoter was produced in a way described below. To perform PCR, through which the SV40 promoter was amplified, pMACS4.1 (Mitenyi Biotech) was used as a template and primers for amplifying the SV40 promoter (MACS4.1 4288L and MACS4.1 1454R) were used. The amplified SV40 promoter was used after being subjected to the restriction enzyme digestion with Sal I and Mlu I. Base sequences of the MACS4.1 4288L (SEQ ID NO: 112) and MACS 4.1 1454R (SEQ ID NO: 113), which are the primers for amplifying the SV40, are shown in Table 1. Base sequences of the SV40 promoter and the SRα are shown in SEQ ID NO: 114 and SEQ ID NO: 115, respectively.

TABLE 1

| Linker/Primer | Base sequence | Position on template |
|---|---|---|
| ESMX Linker | GAATTC GTCGAC GGGG ACGCGT CTAGAG<br>CTTAAG CAGCTG CCCC TGCGCA GAGCTC<br>Eco RI  Sal I       Mlu I  Xho I | — |
| MACS4.1 4288L | ggCCgTCgACTCgACCAATTCTCATgTTTgA | 4288 bp of pMACS 4.1 |
| MACS4.1 1454R | ggCCACgCgTAgggCTCTgggCTTgAAT | 462 bp of pMACS 4.1 |

A total RNA was extracted from a mouse hybridoma cell (Available from: National Institute of Bioscience and Human-Technology, Depository No.: FERM BP-6057), which produces an antibody against a DNA polymerase derived from an anti-pyrococcus kodakaraensis KOD1 strain. With use of the total RNA, a single strand cDNA was synthesized by using ReverTraAce-α-(TOYOBO, FSK-101). Then, in order to assemble pCMV-H and pCMV-L, the following steps were performed: the single strand cDNA was amplified by PCR with use of a primer that specifically amplifies a heavy chain and light chain except for a signal sequence of an anti-KOD polymerase; a signal sequence derived from an immune globulin kappa chain was added to each amplified product; and each amplified product was ligated to a Xba I-Not I site of the plasmid including a CMV promoter.

The pCMV-H and pCMV-L were, together with the pC12.Psv40, co-transfected to a Chinese hamster ovary cell. Two days later, blasticidin (InvivoGen, ant-b1-1) was added at a rate of 5 μg/ml, and thereafter the cells were cultured for 2 weeks so as to obtain stable transformants. During the culture period, a culture medium was replaced every 3 to 4 days. In addition, experiments in which pΔBN.AR1 that includes a DHFR locus Ori-β region IR of full length was used instead of the pC12.Psv40 and in which no IR/MAR was transfected were carried out, as comparative experiments.

Next, the cells were cultured up to a size of a cell culture petri dish 60 mm (SUMILON, MS-11600). Thereafter, a concentration of blasticidin was gradually increased during the culture period, until the cells are able to stably grow at a final concentration of 320 μg/ml. Genome DNAs were obtained from the 1×10$^6$ cells grown as described above, and increases in copy numbers of the heavy chain and light chain antibody genes therein were confirmed by using real time quantitative PCR (ABI, 7900HT). A measuring reagent used in this experiment was SYBR Green Realtime PCR Master Mix (TOYOBO, QPK-201).

After confirming a level of gene amplification, blasticidin was added at a rate of 320 μg/ml. Then, the product was cultured for 4 days. A supernatant of the product was collected, and a level of antibody in the supernatant was measured by EIA. There were carried out as follows in details: a culture supernatant having been 5 times diluted with 10 mM PBS (−) was added to an ELISA plate (SUMILON, MS-8896F), on which an anti-goat mouse antibody was present in a solid phase; the plate was incubated for 2 hours at 35° C.; the plate was rinsed 3 times with PBS-T; a peroxidase-labeled anti-goat mouse antibody having been 4000 times diluted with PBS+1% BSA+10% goat serum was added at a rate of 50 μl/well; the plate was incubated for 2 hours at 35° C.; the ELISA plate was rinsed 4 times with the PBS-T; moisture thereon was completely removed; a coloring reagent of 50 μl was added to each well; the plate was incubated for 15 minutes at room temperature; reaction on the plate was fixed by adding a 1N sulfuric acid solution of 50 μl to each well; and an optical density was measured with use of a plate reader (dominant wavelength: 450 nm, subdominant wavelength: 620 nm). The level of antibody was calculated referring to an analytical curve obtained from a standard preparation.

Figure 9:
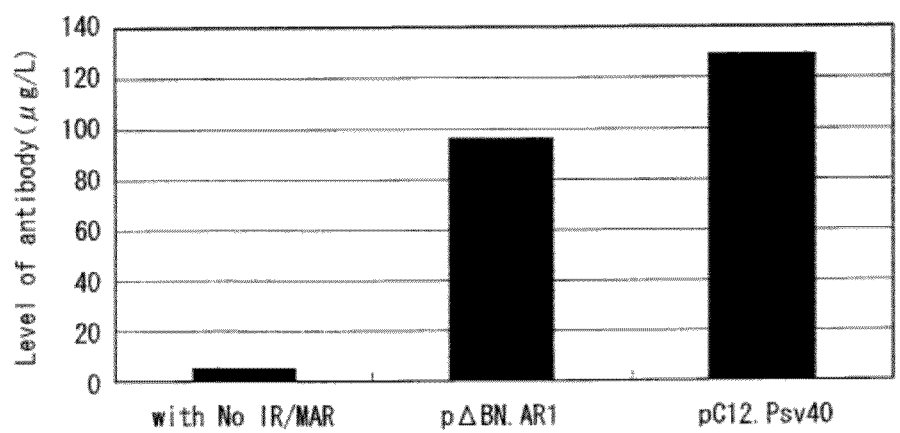
FIG. 9 is a bar chart showing a level of antibody in each experiment group.

Results are shown in FIG. 9 and Table 2. FIG. 9 is a bar chart showing the level of antibody in each experiment group. In FIG. 9, "with No IR/MAR" indicates a result in the case where no IR/MAR plasmid was transfected, "pΔBN.AR1" indicates a result in the case where pΔBN.AR1 was co-transfected, and "pC12.Psv40" indicates a result in the case where pC12.Psv40 was co-transfected. Further, Table 2 is a table showing the level of antibody and copy number of the heavy chain and light chain antibody gene on each experiment group. In table 2, "with No IR/MAR" indicates results in the case where no IR/MAR plasmid was transfected, "pΔB-N.AR1" indicates results in the case where pΔBN.AR1 was co-transfected, and "pC12.Psv40" indicates results in the case where pC12.Psv40 was co-transfected.

TABLE 2

| Vector | Level of antibody (μg/L) | Copy number | |
|---|---|---|---|
| | | H chain | L chain |
| With no IR/MAR | 5 | 2 | 2 |
| pΔBN.AR1 | 96 | 25 | 40 |
| pC12.Psv40 | 129 | 25 | 37 |

FIG. 9 and Table 2 show that high level of gene amplification was observed in the cases where pΔBN.AR1 was co-transfected and where pC12.Psv40 was co-transfected: the level of the gene amplification observed was 12 times that of the case where no IR/MAR plasmid was used. It was of interest that although the level of gene amplification was almost the same between the cases where the pΔBN.AR1 was used and where the pC12.Psv40 was used, a higher level of antibody was observed in the case where the pC12.Psv40 was used. The inventors infer that this is due to high efficiency of gene transfer, which resulted because the pC12.Psv40 (4920 bp) was smaller in vector size than the pΔBN.AR1 (8916 bp).

Figure 10:
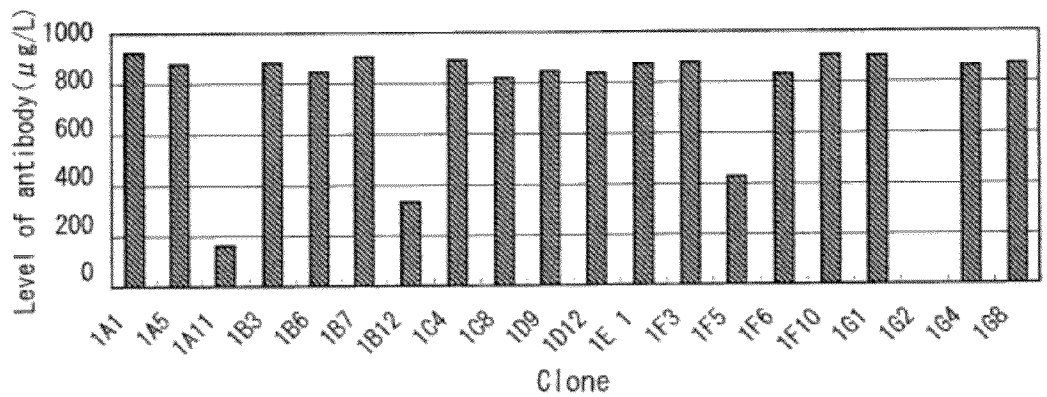
FIG. 10 is a bar chart showing a level of antibody in each clone in case pC12.Psv40 was co-transfected, in Example 3.
Figure 11:
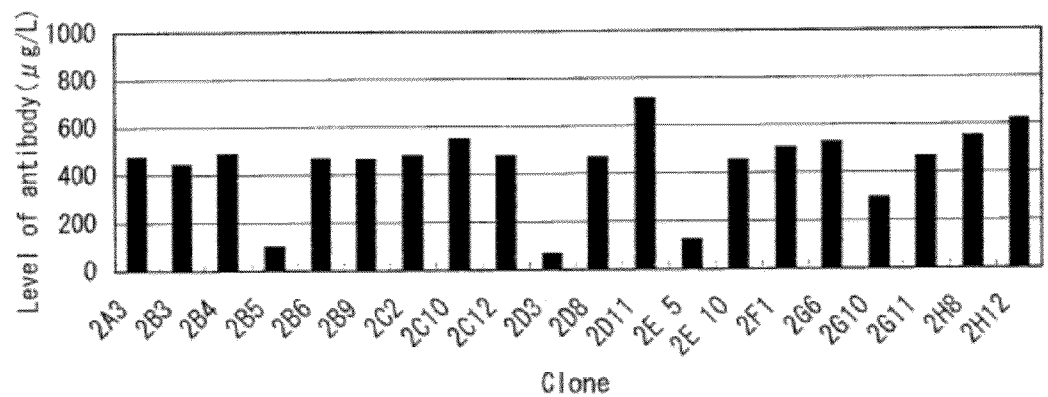
FIG. 11 is a bar chart showing a level of antibody in each clone in case pΔBN.AR1 was co-transfected, in Example 3.

Results of cloning through a limiting dilution are shown in FIGS. 10 and 11, and Tables 3 and 4. FIG. 10 and Table 3 are respectively a bar chart and a table, each of which shows levels of antibody proteins in clones, in which pC12.Psv40 was co-transfected. FIG. 11 and Table 4 are respectively a bar chart and a table, each of which shows levels of antibody proteins in clones, in which pΔBN.AR1 was co-transfected.

TABLE 3

| No. | Clone | Level of antibody (µg/L) |
|---|---|---|
| 1 | 1A1 | 924 |
| 2 | 1A5 | 880 |
| 3 | 1A11 | 162 |
| 4 | 1B3 | 885 |
| 5 | 1B6 | 846 |
| 6 | 1B7 | 904 |
| 7 | 1B12 | 332 |
| 8 | 1C4 | 890 |
| 9 | 1C8 | 822 |
| 10 | 1D9 | 846 |
| 11 | 1D12 | 839 |
| 12 | 1E 1 | 874 |
| 13 | 1F3 | 880 |
| 14 | 1F5 | 429 |
| 15 | 1F6 | 832 |
| 16 | 1F10 | 906 |
| 17 | 1G1 | 902 |
| 18 | 1G2 | 0 |
| 19 | 1G4 | 864 |
| 20 | 1G8 | 869 |
| 21 | polyclone | 132 |

TABLE 4

| No. | Clone | Level of antibody (µg/L) |
|---|---|---|
| 1 | 2A3 | 475 |
| 2 | 2B3 | 443 |
| 3 | 2B4 | 487 |
| 4 | 2B5 | 100 |
| 5 | 2B6 | 467 |
| 6 | 2B9 | 461 |
| 7 | 2C2 | 477 |
| 8 | 2C10 | 549 |
| 9 | 2C12 | 475 |
| 10 | 2D3 | 68 |
| 11 | 2D8 | 465 |
| 12 | 2D11 | 713 |
| 13 | 2E 5 | 123 |
| 14 | 2E 10 | 451 |
| 15 | 2F1 | 503 |
| 16 | 2G6 | 526 |
| 17 | 2G10 | 294 |
| 18 | 2G11 | 463 |
| 19 | 2H8 | 551 |
| 20 | 2H12 | 620 |
| 21 | polyclone | 96 |

The result revealed that it is more likely to obtain a clone having a high production ability of antibody protein when the pC12.Psv40 was co-transfected, compared to the case where the pΔBN.AR1 was co-transfected.

A vector according to the present invention (IR/MAR plasmid) is a vector containing a partial fragment of an IR that has a gene amplification activity, instead of containing a full-length IR. *Thus, the vector is smaller in size than the IR/MAR plasmid, which has been used in conventional high gene amplification systems.*

Therefore, with the vector according to the present invention and the method according to the present invention of using the vector, the following advantages can be enjoyed:

(A) Gene transfer into the mammalian cell can be performed more efficiently.

(B) It is possible to deal with a target gene of a larger size with the high gene amplification system.

(C) A polynucleotide that encodes another element such as a tagged protein or signal peptide can be easily integrated into the IR/MAR plasmid, so that more complicated vector can be prepared.

Further, with the present invention, (D) frequency of HSR is significantly increased compared to an existing method of using a full-length IR, i.e., a gene amplification efficiency is improved. This effect is beyond the expectation of those skilled in the art.

Also, with the present invention, (E) even if a level of gene amplification is the same between the cases where the present invention is carried out and where the full-length IR is used, a higher level of protein production is observed when the present invention is carried out. This effect is beyond the expectation of those skilled in the art.

Accordingly, the present invention makes it possible to amplify a wide range of target genes more efficiently than conventional high gene amplification systems, thereby a large amount of target proteins, which the target genes encode, can be produced.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, the present invention makes it possible to induce amplification of a target gene by using a high gene amplification system containing a partial fragment of an IR. Therefore, the present invention provides such an advantage that a large amount of desired proteins (e.g., useful protein) can be produced.

Accordingly, the present invention is applicable in a wide range of industries, which involve protein production, such as pharmaceutical, chemical, food, cosmetic, and textile industries.

The invention claimed is:

1. A vector for amplifying a target gene in a mammalian cell, the vector including:
   an amplification-activating fragment not being a full-length mammalian replication initiation region but being a partial fragment of the mammalian replication initiation region, and having a gene amplification activity site; and
   a mammalian nuclear matrix attachment region,
   the amplification-activating fragment being a polynucleotide selected from the group consisting of:
   (a) a polynucleotide not being a full length replication initiation region of a c-myc locus but being a partial fragment of the replication initiation region of the c-myc locus, containing at least a polynucleotide having the base sequence shown in SEQ ID NO: 83, and being not shorter than 0.5 kbp but not longer than 2.0 kbp;
   (b) a polynucleotide not being a full-length replication initiation region of a c-myc locus but being a partial fragment of the replication initiation region of the c-myc locus, containing at least a polynucleotide having the base sequence shown in SEQ ID NO: 85, and being not shorter than 0.5 kbp but not longer than 2.0 kbp;
   (c) a polynucleotide not being a full-length replication initiation region of a c-myc locus but being a partial fragment of the replication initiation region of the c-myc locus, containing at least a polynucleotide having the base sequence shown in SEQ ID NO: 94, and being not shorter than 0.5 kbp but not longer than 2.0 kbp;
   (d) a polynucleotide not being a full-length replication initiation region of a dihydrofolate reductase locus but being a partial fragment of the replication initiation region of the dihydrofolate reductase locus, containing at least a polynucleotide having the base sequence shown in SEQ ID NO: 99, and being not shorter than 1.7 kbp but not longer than 3.5 kbp; and
   (e) a polynucleotide not being a full-length replication initiation region of a dihydrofolate reductase locus but being a partial fragment of the replication initiation region of the dihydrofolate reductase locus, containing at least a polynucleotide having the base sequence shown in SEQ ID NO: 102, and being not shorter than 1.7 kbp but not longer than 3.5 kbp.

2. The vector according to claim 1, wherein the amplification-activating fragment derives from a c-myc locus, and contains at least a Duplex Unwinding Element and a topoisomerase II-binding domain.

3. The vector according to claim 1, wherein the mammalian nuclear matrix attachment region derives from a nuclear matrix attachment region of a region selected from the group consisting of an Igκ locus, an SV40 early region, and a dihydrofolate reductase locus.

4. A transformed cell wherein a vector as set forth in claim 1 and a target gene are transferred to a mammalian cell.

5. The vector according to claim 1, wherein:
   the amplification-activating fragment is the polynucleotide having the base sequence shown in SEQ ID NO: 83, SEQ ID NO: 85, SEQ ID NO: 94, SEQ ID NO: 99 or SEQ ID NO: 102.

* * * * *

SEQUENCE LISTING

<160> NUMBER OF SEQ ID NOS: 115

<210> SEQ ID NO 1
<211> LENGTH: 259
<212> TYPE: DNA
<213> ORGANISM: Homo sapiens
<220> FEATURE:
<308> DATABASE ACCESSION NUMBER: Genbank X00364
<309> DATABASE ENTRY DATE: 2002-06-03

<313> RELEVANT RESIDUES IN SEQ ID NO: 189 to 447

<400> SEQUENCE: 1

```
tctttcttcg gaccttctgc agccaacctg aaagaataac aaggaggtgg ctggaaactt    60
gttttaagga accgcctgtc cttccccgc tggaaacctt gcacctcgga cgctcctgct    120
cctgccccca cctgaccccc gccctcgttg acatccaggc gcgatgatct ctgctgccag    180
tagagggcac acttacttta ctttcgcaaa cctgaacgcg ggtgctgccc agagagggg    240
cggagggaaa gacgctttg                                                 259
```

<210> SEQ ID NO 2
<211> LENGTH: 243
<212> TYPE: DNA
<213> ORGANISM: Homo sapiens
<220> FEATURE:
<308> DATABASE ACCESSION NUMBER: Genbank X00364
<309> DATABASE ENTRY DATE: 2002-06-03
<313> RELEVANT RESIDUES IN SEQ ID NO: 745 to 987

<400> SEQUENCE: 2

```
tgttttttgt ttttcatgcc gtggaataac acaaaataaa aaatcccgag ggaatataca    60
ttatatatta aatatagatc atttcaggga gcaaacaaat catgtgtggg gctgggcaac    120
tagctgagtc gaagcgtaaa taaaatgtga atacacgttt gcgggttaca tacagtgcac    180
tttcactagt attcagaaaa aattgtgagt cagtgaacta ggaaattaat gcctggaagg    240
cag                                                                  243
```

<210> SEQ ID NO 3
<211> LENGTH: 799
<212> TYPE: DNA
<213> ORGANISM: Homo sapiens
<220> FEATURE:
<308> DATABASE ACCESSION NUMBER: Genbank X00364
<309> DATABASE ENTRY DATE: 2002-06-03
<313> RELEVANT RESIDUES IN SEQ ID NO: 189 to 987

<400> SEQUENCE: 3

```
tctttcttcg gaccttctgc agccaacctg aaagaataac aaggaggtgg ctggaaactt    60
gttttaagga accgcctgtc cttccccgc tggaaacctt gcacctcgga cgctcctgct    120
cctgccccca cctgaccccc gccctcgttg acatccaggc gcgatgatct ctgctgccag    180
tagagggcac acttacttta ctttcgcaaa cctgaacgcg ggtgctgccc agagagggg    240
cggagggaaa gacgctttgc agcaaaatcc agcatagcga ttggttgctc cccgcgtttg    300
cggcaaaggc ctgaggcag gagtaatttg caatccttaa agctgaattg tgcagtgcat    360
cggatttgga agctactata ttcacttaac acttgaacgc tgagctgcaa actcaacggg    420
taataaccca tcttgaacag cgtacatgct atacacacac ccctttcccc cgaattgttt    480
tctcttttgg aggtggtgga gggagagaaa agtttactta aaatgccttt gggtgaggga    540
ccaaggatga gaagaatgtt ttttgttttt catgccgtgg aataacacaa aataaaaaat    600
cccgagggaa tatacattat atattaaata tagatcattt cagggagcaa acaaatcatg    660
tgtgggctg gcaactagc tgagtcgaag cgtaaataaa atgtgaatac acgtttgcgg    720
gttacataca gtgcactttc actagtattc agaaaaaatt gtgagtcagt gaactaggaa    780
attaatgcct ggaaggcag                                                 799
```

<210> SEQ ID NO 4
<211> LENGTH: 1292
<212> TYPE: DNA

<213> ORGANISM: Homo sapiens

<400> SEQUENCE: 4

```
gctttcaaat tttgtggtta aaaagatga tgagtttcta agacgtgggg gctaaagctt      60
gtttggccgt tttagggttt gttggaattt tttttcgtc tatgtacttg tgaattattt     120
cacgtttgcc attaccggtt ctccataggg tgatgttcat tagcagtggt gataggttaa    180
ttttcaccat ctcttatgcg gttgaatagt cacctctgaa ccactttttc ctccagtaac    240
tcctctttct tcggaccttc tgcagccaac ctgaaagaat aacaaggagg tggctggaaa    300
cttgttttaa ggaaccgcct gtccttcccc cgctggaaac cttgcacctc ggacgctcct    360
gctcctgccc ccacctgacc cccgccctcg ttgacatcca ggcgcgatga tctctgctgc    420
cagtagaggg cacacttact ttactttcgc aaacctgaac gcgggtgctg cccagagagg    480
gggcggaggg aaagacgctt tgcagcaaaa tccagcatag cgattggttg ctccccgcgt    540
ttgcggcaaa ggcctggagg caggagtaat ttgcaatcct taaagctgaa ttgtgcagtg    600
catcggattt ggaagctact atattcactt aacacttgaa cgctgagctg caaactcaac    660
gggtaataac ccatcttgaa cagcgtacat gctatacaca cccccttc ccccgaattg      720
ttttctcttt tggaggtggt ggagggagag aaaagtttac ttaaaatgcc tttgggtgag    780
ggaccaagga tgagaagaat gttttttgtt tttcatgccg tggaataaca caaaataaaa    840
aatcccgagg gaatatacat tatatattaa atatagatca tttcagggag caaacaaatc    900
atgtgtgggg ctgggcaact agctgagtcg aagcgtaaat aaaatgtgaa tacacgtttg    960
cgggttacat acagtgcact ttcactagta ttcagaaaaa attgtgagtc agtgaactag   1020
gaaattaatg cctggaaggc agccaaattt taattagctc aagactcccc ccccccccca   1080
aaaaaggca cggaagtaat actcctctcc tcttctttga tcagaatcga tgcatttttt   1140
gtgcatgacc gcatttccaa taataaaagg ggaaagagga cctggaaagg aattaaacgt   1200
ccggtttgtc cggggaggaa agagttaacg gttttttttca caagggtctc tgctgactcc   1260
cccggctcgg tccacaagct ctccacttgc cc                                 1292
```

<210> SEQ ID NO 5
<211> LENGTH: 2033
<212> TYPE: DNA
<213> ORGANISM: Homo sapiens

<400> SEQUENCE: 5

```
gctttcaaat tttgtggtta aaaagatga tgagtttcta agacgtgggg gctaaagctt      60
gtttggccgt tttagggttt gttggaattt tttttcgtc tatgtacttg tgaattattt     120
cacgtttgcc attaccggtt ctccataggg tgatgttcat tagcagtggt gataggttaa    180
ttttcaccat ctcttatgcg gttgaatagt cacctctgaa ccactttttc ctccagtaac    240
tcctctttct tcggaccttc tgcagccaac ctgaaagaat aacaaggagg tggctggaaa    300
cttgttttaa ggaaccgcct gtccttcccc cgctggaaac cttgcacctc ggacgctcct    360
gctcctgccc ccacctgacc cccgccctcg ttgacatcca ggcgcgatga tctctgctgc    420
cagtagaggg cacacttact ttactttcgc aaacctgaac gcgggtgctg cccagagagg    480
gggcggaggg aaagacgctt tgcagcaaaa tccagcatag cgattggttg ctccccgcgt    540
ttgcggcaaa ggcctggagg caggagtaat ttgcaatcct taaagctgaa ttgtgcagtg    600
catcggattt ggaagctact atattcactt aacacttgaa cgctgagctg caaactcaac    660
gggtaataac ccatcttgaa cagcgtacat gctatacaca cccccttc ccccgaattg      720
```

```
ttttctcttt tggaggtggt ggagggagag aaaagtttac ttaaaatgcc tttgggtgag      780
ggaccaagga tgagaagaat gttttttgtt tttcatgccg tggaataaca caaaataaaa      840
aatcccgagg gaatatacat tatatattaa atatagatca tttcagggag caaacaaatc      900
atgtgtgggg ctgggcaact agctgagtcg aagcgtaaat aaaatgtgaa tacacgtttg      960
cgggttacat acagtgcact ttcactagta ttcagaaaaa attgtgagtc agtgaactag     1020
gaaattaatg cctggaaggc agccaaattt taattagctc aagactcccc ccccccccca     1080 aaaaaggca cggaagtaat actcctctcc tcttctttga tcagaatcga tgcattttt       1140 gtgcatgacc gcatttccaa taataaaagg ggaaagagga cctggaaagg aattaaacgt     1200
ccggtttgtc cggggaggaa agagttaacg gttttttca aagggtctc tgctgactcc      1260 cccggctcgg tccacaagct ctccacttgc cccttttagg aagtccggtc ccgcggttcg     1320 ggtacccct gcccctccca tattctcccg tctagcacct ttgatttctc ccaaacccgg     1380
cagcccgaga ctgttgcaaa ccggcgccac agggcgcaaa ggggatttgt ctcttctgaa     1440
acctggctga gaaattggga actccgtgtg ggaggcgtgg gggtgggacg gtggggtaca     1500
gactggcaga gagcaggcaa cctccctctc gccctagccc agctctggaa caggcagaca     1560
catctcaggg ctaaacagac gcctcccgca cggggcccca cggaagcctg agcaggcggg     1620
gcaggagggg cggtatctgc tgcttttggca gcaaattggg ggactcagtc tgggtggaag     1680
gtatccaatc cagatagctg tgcatacata atgcataata catgactccc cccaacaaat     1740
gcaatgggag tttattcata acgcgctctc caagtatacg tggcaatgcg ttgctgggtt     1800 atttttaatca ttctaggcat cgttttcctc cttatgcctc tatcattcct ccctatctac     1860
actaacatcc cacgctctga acgcgcgccc attaatacc ttctttcctc cactctccct     1920
gggactcttg atcaaagcgc ggccctttcc ccagccttag cgaggcgccc tgcagcctgg     1980
tacgcgcgtg gcgtggcggt gggcgcgcag tgcgttctct gtgtggaggg cag           2033

<210> SEQ ID NO 6
<211> LENGTH: 1639
<212> TYPE: DNA
<213> ORGANISM: Homo sapiens

<400> SEQUENCE: 6
gctttcaaat tttgtggtta aaaaagatga tgagtttcta agacgtgggg gctaaagctt       60
gtttggccgt tttagggttt gttggaattt ttttttcgtc tatgtacttg tgaattattt      120
cacgtttgcc attaccggtt ctccataggg tgatgttcat tagcagtggt gataggttaa      180
ttttcaccat ctcttatgcg gttgaatagt cacctctgaa ccactttttc ctccagtaac      240 tcctcttttct tcggaccttc tgcagccaac ctgaaagaat aacaaggagg tggctggaaa      300 cttgtttttaa ggaaccgcct gtccttcccc cgctggaaac cttgcacctc ggacgctcct      360
gctcctgccc ccacctgacc cccgccctcg ttgacatcca ggcgcgatga tctctgctgc      420
cagtagaggg cacacttact ttactttcgc aaacctgaac gcgggtgctg cccagagagg      480
gggcggaggg aaagacgctt tgcagcaaaa tccagcatag cgattggttg ctcccgcgt      540 tgcggcaaa ggcctggagg caggagtaat ttgcaatcct taaagctgaa ttgtgcagtg      600
catcggattt ggaagctact atattcactt aacacttgaa cgctgagctg caaactcaac      660
gggtaataac ccatcttgaa cagcgtacat gctatacaca cacccctttc ccccgaattg      720
ttttctcttt tggaggtggt ggagggagag aaaagtttac ttaaaatgcc tttgggtgag      780
ggaccaagga tgagaagaat gttttttgtt tttcatgccg tggaataaca caaaataaaa      840
```

-continued

| | |
|---|---|
| aatcccgagg gaatatacat tatatattaa atatagatca tttcagggag caaacaaatc | 900 |
| atgtgtgggg ctgggcaact agctgagtcg aagcgtaaat aaaatgtgaa tacacgtttg | 960 |
| cgggttacat acagtgcact ttcactagta ttcagaaaaa attgtgagtc agtgaactag | 1020 |
| gaaattaatg cctggaaggc agccaaattt taattagctc aagactcccc ccccccccca | 1080 |
| aaaaaggca cggaagtaat actcctctcc tcttctttga tcagaatcga tgcattttt | 1140 |
| gtgcatgacc gcatttccaa taataaaagg ggaaagagga cctggaaagg aattaaacgt | 1200 |
| ccggtttgtc cggggaggaa agagttaacg gttttttca aagggtctc tgctgactcc | 1260 |
| cccggctcgg tccacaagct ctccacttgc cccttttagg aagtccggtc cgcggttcg | 1320 |
| ggtacccct gcccctccca tattctcccg tctagcacct ttgatttctc ccaaacccgg | 1380 |
| cagcccgaga ctgttgcaaa ccggcgccac agggcgcaaa ggggatttgt ctcttctgaa | 1440 |
| acctggctga gaaattggga actccgtgtg ggaggcgtgg gggtgggacg gtggggtaca | 1500 |
| gactggcaga gagcaggcaa cctccctctc gccctagccc agctctggaa caggcagaca | 1560 |
| catctcaggg ctaaacagac gcctcccgca cggggcccca cggaagcctg agcaggcggg | 1620 |
| gcaggagggg cggtatctg | 1639 |

<210> SEQ ID NO 7
<211> LENGTH: 1588
<212> TYPE: DNA
<213> ORGANISM: Homo sapiens

<400> SEQUENCE: 7

| | |
|---|---|
| tctttcttcg gaccttctgc agccaacctg aaagaataac aaggaggtgg ctggaaactt | 60 |
| gttttaagga accgcctgtc cttccccgc tggaaacctt gcactcgga cgctcctgct | 120 |
| cctgccccca cctgaccccc gccctcgttg acatccaggc gcgatgatct ctgctgccag | 180 |
| tagagggcac acttacttta ctttcgcaaa cctgaacgcg ggtgctgccc agagaggggg | 240 |
| cggagggaaa gacgctttgc agcaaaatcc agcatagcga ttggttgctc cccgcgtttg | 300 |
| cggcaaaggc ctggaggcag gagtaatttg caatccttaa agctgaattg tgcagtgcat | 360 |
| cggatttgga agctactata ttcacttaac acttgaacgc tgagctgcaa actcaacggg | 420 |
| taataaccca tcttgaacag cgtacatgct atacacacac ccctttcccc cgaattgttt | 480 |
| tctcttttgg aggtggtgga gggagagaaa agtttactta aaatgccttt gggtgaggga | 540 |
| ccaaggatga gaagaatgtt ttttgttttt catgccgtgg aataacacaa aataaaaaat | 600 |
| cccgagggaa tatacattat atattaaata tagatcattt cagggagcaa acaaatcatg | 660 |
| tgtgggctg ggcaactagc tgagtcgaag cgtaaataaa atgtgaatac acgtttgcgg | 720 |
| gttacataca gtgcactttc actagtattc agaaaaatt gtgagtcagt gaactaggaa | 780 |
| attaatgcct ggaaggcagc caaattttaa ttagctcaag actcccccc cccccaaaa | 840 |
| aaaggcacgg aagtaatact cctctcctct tctttgatca gaatcgatgc atttttgtg | 900 |
| catgaccgca tttccaataa taaagggga agaggacct ggaaaggaat taaacgtccg | 960 |
| gtttgtccgg ggaggaaaga gttaacggtt ttttcacaa gggtctctgc tgactccccc | 1020 |
| ggctcggtcc acaagctctc cacttgcccc ttttaggaag tccggtcccg cggttcgggt | 1080 |
| accccctgcc cctcccatat tctcccgtct agcacctttg atttctccca aacccggcag | 1140 |
| cccgagactg ttgcaaaccg gcgccacagg gcgcaaaggg gatttgtctc ttctgaaacc | 1200 |
| tggctgagaa attgggaact ccgtgtggga ggcgtggggg tggacggtg ggtacagac | 1260 |
| tggcagagag caggcaacct ccctctcgcc ctagcccagc tctggaacag gcagacacat | 1320 |

```
ctcagggcta aacagacgcc tcccgcacgg ggccccacgg aagcctgagc aggcggggca    1380
ggaggggcgg tatctgctgc tttggcagca aattggggga ctcagtctgg gtggaaggta    1440
tccaatccag atagctgtgc atacataatg cataatacat gactccccc  aacaaatgca    1500 atgggagttt attcataacg cgctctccaa gtatacgtgg caatgcgttg ctgggttatt    1560
ttaatcattc taggcatcgt tttcctcc                                       1588

<210> SEQ ID NO 8
<211> LENGTH: 1514
<212> TYPE: DNA
<213> ORGANISM: Homo sapiens

<400> SEQUENCE: 8 ctttccccg  aattgttttc tcttttggag gtggtggagg gagagaaaag tttacttaaa      60
atgcctttgg gtgagggacc aaggatgaga agaatgtttt ttgttttttca tgccgtggaa    120 taacacaaaa taaaaaatcc cgagggaata tacattatat attaaatata gatcatttca    180
gggagcaaac aaatcatgtg tggggctggg caactagctg agtcgaagcg taaataaaat    240
gtgaatacac gtttgcgggt tacatacagt gcactttcac tagtattcag aaaaaattgt    300
gagtcagtga actaggaaat taatgcctgg aaggcagcca aattttaatt agctcaagac    360
tccccccccc ccccaaaaaa aggcacgaaa gtaaactcc  tctcctcttc tttgatcaga    420
atcgatgcat tttttgtgca tgaccgcatt tccaataata aaaggggaaa gaggacctgg    480
aaaggaatta aacgtccggt ttgtccgggg aggaaagagt taacggtttt tttcacaagg    540
gtctctgctg actccccgg  ctcggtccac aagctctcca cttgccctt  ttaggaagtc    600 cggtcccgcg gttcgggtac cccctgcccc tcccatattc tcccgtctag cacctttgat    660
ttctcccaaa cccggcagcc cgagactgtt gcaaaccggc gccacagggc gcaaagggga    720
tttgtctctt ctgaaacctg gctgagaaat tgggaactcc gtgtgggagg cgtgggggtg    780
ggacggtggg gtacagactg gcagagagca ggcaacctcc ctctcgcct  agcccagctc    840 tggaacaggc agacacatct cagggctaaa cagacgcctc ccgcacgggg ccccacggaa    900
gcctgagcag gcggggcagg aggggcggta tctgctgctt tggcagcaaa ttggggact    960 cagtctgggt ggaaggtatc caatccagat agctgtgcat acataatgca taatacatga   1020 ctcccccaa  caaatgcaat gggagtttat tcataacgcg ctctccaagt atacgtggca   1080
atgcgttgct gggttatttt aatcattcta ggcatcgttt tcctccttat gcctctatca   1140
ttcctcccta tctacactaa catcccacgc tctgaacgcg cgccattaa  tacccttctt   1200 tcctccactc tccctgggac tcttgatcaa agcgcggccc ttttcccagc cttagcgagg   1260
cgccctgcag cctggtacgc gcgtggcgtg cggtgggcg  cgcagtgcgt tctctgtgtg   1320
gagggcagct gttccgcctg cgatgattta tactcacagg acaaggatgc ggtttgtcaa   1380
acagtactgc tacggaggag cagcagagaa agggagaggg tttgagaggg agcaaaagaa   1440
aatggtaggc gcgcgtagtt aattcatgcg gctctcttac tctgtttaca tcctagagct   1500
agagtgctcg gctg                                                     1514

<210> SEQ ID NO 9
<211> LENGTH: 1976
<212> TYPE: DNA
<213> ORGANISM: Homo sapiens

<400> SEQUENCE: 9
tctttcttcg gaccttctgc agccaacctg aaagaataac aaggaggtgg ctggaaactt     60
```

```
gttttaagga accgcctgtc cttccccgc tggaaacctt gcacctcgga cgctcctgct      120
cctgccccca cctgaccccc gccctcgttg acatccaggc gcgatgatct ctgctgccag      180
tagagggcac acttacttta ctttcgcaaa cctgaacgcg ggtgctgccc agagaggggg      240
cggagggaaa gacgctttgc agcaaaatcc agcatagcga ttggttgctc cccgcgtttg      300
cggcaaaggc ctggaggcag gagtaatttg caatccttaa agctgaattg tgcagtgcat      360
cggatttgga agctactata ttcacttaac acttgaacgc tgagctgcaa actcaacggg      420
taataaccca tcttgaacag cgtacatgct atacacacac ccctttcccc cgaattgttt      480
tctcttttgg aggtggtgga gggagagaaa agtttactta aaatgccttt gggtgaggga      540
ccaaggatga aagaatgtt ttttgttttt catgccgtgg aataacacaa aataaaaaat       600
cccgagggaa tatacattat atattaaata tagatcattt cagggagcaa acaaatcatg      660
tgtggggctg gcaactagc tgagtcgaag cgtaaataaa atgtgaatac acgtttgcgg       720
gttacataca gtgcactttc actagtattc agaaaaaatt gtgagtcagt gaactaggaa      780
attaatgcct ggaaggcagc caaatttaa ttagctcaag actccccccc cccccaaaa       840
aaaggcacgg aagtaatact cctctcctct tctttgatca gaatcgatgc attttttgtg      900
catgaccgca tttccaataa taaaagggga aagaggacct ggaaaggaat taaacgtccg      960
gtttgtccgg ggaggaaaga gttaacggtt ttttcacaa gggtctctgc tgactccccc     1020
ggctcggtcc acaagctctc cacttgcccc ttttaggaag tccggtcccg cggttcgggt     1080
accccctgcc cctcccatat tctcccgtct agcacctttg atttctccca aaccccggcag    1140
cccgagactg ttgcaaaccg gcgccacagg gcgcaaaggg gatttgtctc ttctgaaacc     1200
tggctgagaa attgggaact ccgtgtggga ggcgtggggg tgggacggtg gggtacagac     1260
tggcagagag caggcaacct ccctctcgcc ctagcccagc tctggaacag gcagacacat     1320
ctcagggcta aacagacgcc tcccgcacgg ggccccacgg aagcctgagc aggcggggca     1380
ggagggggcgg tatctgctgc tttggcagca aattggggga ctcagtctgg gtggaaggta    1440
tccaatccag atagctgtgc atacataatg cataatacat gactccccccc aacaaatgca    1500
atgggagttt attcataacg cgctctccaa gtatacgtgg caatgcgttg ctgggttatt     1560
ttaatcattc taggcatcgt tttcctcctt atgcctctat cattcctccc tatctacact     1620
aacatcccac gctctgaacg cgcgcccatt aatacccttc tttcctccac tctccctggg    1680
actcttgatc aaagcgcggc ccttcccca gccttagcga ggcgccctgc agcctggtac     1740
gcgcgtggcg tggcggtggg cgcgcagtgc gttctctgtg tggagggcag ctgttccgcc    1800
tgcgatgatt tatactcaca ggacaaggat gcggtttgtc aaacagtact gctacggagg    1860
agcagcagag aaagggagag ggtttgagag ggagcaaaag aaaatggtag gcgcgcgtag    1920
ttaattcatg cggctctctt actctgttta catcctagag ctagagtgct cggctg        1976

<210> SEQ ID NO 10
<211> LENGTH: 1744
<212> TYPE: DNA
<213> ORGANISM: Cricetulus griseus
<220> FEATURE:
<308> DATABASE ACCESSION NUMBER: Genbank X94372
<309> DATABASE ENTRY DATE: 1996-12-12
<313> RELEVANT RESIDUES IN SEQ ID NO: 3142 to 4885

<400> SEQUENCE: 10
tgaagagaca ccatgaccac agaaactctt ataaaggaaa gcaattattg ggtccagctt        60
acagttcaga ggtttaatcc attgtcatga ttgcaggaag tatggtggcc cacaggcaga      120
```

```
catggtgctg gagaagtaga tgagagttct atatcagatt gacacacttc ttccaacaag    180
gccacacctc cactcactct gagcctatgg ggccattttc attcaaacca ccaaagctac    240
aaggtagctt ataccccagc ttgctatttc tgatgagact tagtaaatag tcttaaaagc    300
ccataaaatg actcaaaact agttttttta ttattattat tagttcaaat taggaagaag    360
cttgctttac atgtcaatcc cttctccctc tccctcatca aaactagttt tttgtttttt    420 aggtttttt  tcaagacagg gtttctctgt gtagctttgg agcctatcct ggcactcgct    480
ctggagacca ggctggcctc gaactcacag agatctgcct gcctttgcct cccgagtcct    540
gggattaaag gcatgcacca ccaacacctg gccaaaatta gttttaagtc cagttctagg    600
agctccaatg ccctcttttg gcttccatgg gaaccaggaa cactatatat atatatatat    660 atatatat   atatatatat atatatatat tcaggcaaat atttatgcat ataaaaataa    720
aataaatctt ttttccttttt tttttaaag aagtgacatt gtcttggaat ttttgtggct    780
gctctgccct tatgtgtaac tggacactac cagcatctaa acactggcct gaaaccagcc    840
aaagaaaacc tttgtgccag gtcctgtgtc aaagtattat gttcctttta ggatatccta    900
tatcctaaag gatttatttt actgatagca tcttaacttc ctttgaaagg ttggtcttct    960
caagcagtcc tcgtggagct ggctcctcag ctaatgccag gggacaataa tgatcccctc   1020
ccaaaaccaa acagaaaacc atggcaactc tggtttcctt gggcagcacc tgctttaaga   1080
atgagcaaat gaccaatcag ctcatgaaac taaatactct attattacta aaatattttt   1140
ttgagacagg gcatggaatt catcacatag ttcaggttgg ccttgaactc agagagactc   1200
acttaccttt gcctcccacg tgctggaatt aaaggcatga accaccacac caaacataac   1260
acttgaattt tggaagagtc cttcttccaa tagatttgag gttttgaaaa tgtggcacag   1320
aaaatatgaa ttcaaatata atgaaaacaa gagataactt tcaactaagt ttctataggt   1380
tcttgctagg aatcctaagc ttgtctgaaa ctctagagct tctgtttcta gtcttctgag   1440
tgttagtatt gtaggtatgt gccctgcctc agtgtgatgt ttttgataat cttaaagaaa   1500
tcaaagaaat tttataaaag actagactgt gctacacaaa aagaatattc agatgccaag   1560
aaagagttct tagaaattaa gaaatatgct actagtataa atcctttata aagtggaatg   1620
acaaatctga tgaaatctta ctaaaagtag aaaaacataa acatcaaaga catgaataat   1680
aagaaaatca tattgtgcat atcattaacc taaaacatta acttgcaaaa atagaatagt   1740
ccaa                                                                 1744
```

<210> SEQ ID NO 11
<211> LENGTH: 3025
<212> TYPE: DNA
<213> ORGANISM: Cricetulus griseus

<400> SEQUENCE: 11

```
tgaagagaca ccatgaccac agaaactctt ataaaggaaa gcaattattg ggtccagctt     60
acagttcaga ggtttaatcc attgtcatga ttgcaggaag tatggtggcc cacaggcaga    120
catggtgctg gagaagtaga tgagagttct atatcagatt gacacacttc ttccaacaag    180
gccacacctc cactcactct gagcctatgg ggccattttc attcaaacca ccaaagctac    240
aaggtagctt ataccccagc ttgctatttc tgatgagact tagtaaatag tcttaaaagc    300
ccataaaatg actcaaaact agttttttta ttattattat tagttcaaat taggaagaag    360
cttgctttac atgtcaatcc cttctccctc tccctcatca aaactagttt tttgtttttt    420 aggtttttt  tcaagacagg gtttctctgt gtagctttgg agcctatcct ggcactcgct    480
```

```
ctggagacca ggctggcctc gaactcacag agatctgcct gcctttgcct cccgagtcct    540
gggattaaag gcatgcacca ccaacacctg gccaaaatta gttttaagtc cagttctagg    600
agctccaatg ccctcttttg cttccatgg gaaccaggaa cactatatat atatatatat    660
atatatatat atatatatat atatatatat tcaggcaaat atttatgcat ataaaaataa    720
aataaatctt ttttccttttt tttttttaaag aagtgacatt gtcttggaat ttttgtggct    780
gctctgccct tatgtgtaac tggacactac cagcatctaa acactggcct gaaaccagcc    840
aaagaaaacc tttgtgccag gtcctgtgtc aaagtattat gttccttta ggatatccta    900 tatcctaaag gatttatttt actgatagca tcttaacttc ctttgaaagg ttggtcttct    960
caagcagtcc tcgtggagct ggctcctcag ctaatgccag gggacaataa tgatcccctc   1020
ccaaaaccaa acagaaaacc atggcaactc tggtttcctt gggcagcacc tgctttaaga   1080
atgagcaaat gaccaatcag ctcatgaaac taaatactct attattacta aaatattttt   1140
ttgagacagg gcatggaatt catcacatag ttcaggttgg ccttgaactc agagagactc   1200
acttaccttt gcctcccacg tgctggaatt aaaggcatga accaccacac caaacataac   1260
acttgaattt tggaagagtc cttcttccaa tagatttgag gttttgaaaa tgtggcacag   1320
aaaatatgaa ttcaaatata atgaaaacaa gagataactt tcaactaagt ttctataggt   1380
tcttgctagg aatcctaagc ttgtctgaaa ctctagagct tctgtttcta gtcttctgag   1440
tgttagtatt gtaggtatgt gccctgcctc agtgtgatgt ttttgataat cttaaagaaa   1500
tcaaagaaat tttataaaag actagactgt gctacacaaa aagaatattc agatgccaag   1560
aaagagttct tagaaattaa gaaatatgct actagtataa atcctttata aagtggaatg   1620
acaaatctga tgaaatctta ctaaaagtag aaaaacataa acatcaaaga catgaataat   1680
aagaaaatca tattgtgcat atcattaacc taaaacatta acttgcaaaa atagaatagt   1740
ccaaaaagta aacaaaataa ataaatcacc aagacatgat acaaggacaa ttcctagaat   1800
gataaaacaa gaatattcat tataaaaggc cctatcacta aagcacaaca gaaacagact   1860
caaaagataa atcttcattg tcactggaga gaagtcatac tatcatagca ctcagaagga   1920
aataaaaatc aaaatgtcaa aaaggacctc agcctctgaa acacaaatac aaaatatgtc   1980
cgccttcttg acaggcatta ctcttcaatt aacattttaa gaaaactata aagagagctt   2040
agtattttaa gaaatctgta gctatttctt ttataagcat gacaactaag tttcctgatt   2100
taaacagacc taaaaaaccg gtgaagtgag tggagaaagg ggatacgaag acagcatccc   2160
acatgactgc tccagtaaa ggcaaggtct tcatccattt tatcctgaac ctgggaaat   2220 ttataaagaa cagaaatgta tttctctcag ttctggagcc tcagtccagg acactaagtc   2280
taggtactac actctcacat ggtggaaact agaaagcaag ctcacttgtc actcactacc   2340
tgatgcctct ttcatcaatc ccattgataa ggaagagacc tggcatctca gtttcctaag   2400
gactcagctc ttactaacat tagctgtcat ttctgggtca ctgcaacaga aagcctgaca   2460
gaagcaaccc aggggaagaa ggatgtattt tggctcactg tctctgagga tttcaactta   2520
tcccagcaat aaagggataa aggcattgca gcaggaatat gtgtggcaga agctgtttat   2580
gtcacaataa acaaataaac acacgctagc gcgcgcgcac acacacacac acacacacac   2640
acacacacac acacagagag agagagagag agagagagag agagagagag agagagggg   2700 ggggcagac agacagacag agggagagag gcagagaggg agagagagag agagagagag   2760
agagagagag agagagagag agagagagag agagaaatca aaggcccacc tccatcagac   2820
tggtcccata tcccaaattt ctagaacctc ctaaaacaac accatcaact gagggagaca   2880
```

```
ttttttggatt gaaagcataa tgccattacc caggcagaat ctgcctgtct gggggagtca   2940
catttaagcc atggtatcaa ttgacctcat gtaatttcag aatactacat aaaactatca   3000 gatattttc atgatgaatt tctaa                                          3025

<210> SEQ ID NO 12
<211> LENGTH: 3079
<212> TYPE: DNA
<213> ORGANISM: Cricetulus griseus

<400> SEQUENCE: 12
caggcctttg agctcagact agacagaact cacaggttct ctgagctttc cagcttgatg     60
aatgtccatg gcagtcttca cacttaacac ctgacagact taatgatcat atgaaccaat    120
tcaaatctga ccatcactcg ggtcattctt ttgattctgt cactttggag aactaatacc    180
gaggacataa aatgccatca catcgttatt ttcttcctgt ctgtgaatat tttctttttt    240
tttcttgttt tttttttttt tttttttttt tttttttttt ttttgttttt ctctgtgtag    300
ctttggagcc tatcctggca cttgctctgg agaccaggct gacctgaact ctcagagatc    360
cgcctgcctc tgcctcccga gtgctgggat taaaggcgtg taccaccaac gctcggcctg    420
tctgtgaata tttaaaatga aactttggaa aatgttctga accagctggt tgtcagatag    480
tcagagaact ttcgtaaggt aggtgtgggt tatagcataa tcccacacaa gaggctgaag    540
caggaggatt ttgtgtttga gggcagctag agccacatgg tgagtccctg cctcaaaaca    600
caaaagcaag acaaaaacaa gctccaaata agattcactg ggccctttct ttccttcctt    660
ctcagtgagt ccacttgctt taaaatcagg tcttaaagac gcactagatg ctgaacttaa    720
cagtaataat aaatatcttc tcttacagta cagattatgc tctataaaca ctgcactgat    780
aaagttcagc cttaaccttt gttctgtaaa tgtttcctag ttttctact gccgtattat    840 aagacaaatg tcagcatgaa ggcaggtttt tcagaaaaca cagcagctcc acagatggcc    900
tctaatccat aatcattaaa gacaagactg caactttttc aactggaaat cattcaagat    960 gttttctga gtccctacc aggacacaag ccaccctggt tgctgtgtga catcagttag   1020
gtagactctg aactggcttc ccaagaaatt atacaaaagc aaggtgtcac ctagtattag   1080
cataacttct gataactact gtcttagctg gggtttctat tgctgtgaag agacaccatg   1140
accacagaaa ctcttataaa ggaaagcaat tattgggtcc agcttacagt tcagaggttt   1200
aatccattgt catgattgca ggaagtatgg tggcccacag gcagacatgg tgctggagaa   1260
gtagatgaga gttctatatc agattgacac acttcttcca acaaggccac acctccactc   1320
actctgagcc tatggggcca ttttcattca aaccaccaaa gctacaaggt agcttatacc   1380
ccagcttgct atttctgatg agacttagta aatagtctta aaagcccata aaatgactca   1440
aaactagttt ttttattatt attattagtt caaattagga agaagcttgc tttacatgtc   1500
aatcccttct ccctctccct catcaaaact agttttttgt tttttaggtt ttttttcaag   1560
acagggtttc tctgtgtagc tttggagcct atcctggcac tcgctctgga gaccaggctg   1620
gcctcgaact cacagagatc tgcctgcctt tgcctcccga gtcctgggat taaaggcatg   1680
caccaccaac cctggccaa aattagtttt aagtccagtt ctaggagctc caatgccctc   1740
ttttggcttc catgggaacc aggaacacta tatatatata tatatatata tatatatata   1800
tatatatata tatattcagg caaatattta tgcatataaa aataaaataa atcttttttc   1860
cttttttttt taaagaagtg acattgtctt ggaattttg tggctgctct gcccttatgt   1920
gtaactggac actaccagca tctaaacact ggcctgaaac cagccaaaga aaacctttgt   1980
```

-continued

| | |
|---|---|
| gccaggtcct gtgtcaaagt attatgttcc ttttaggata tcctatatcc taaaggattt | 2040 |
| attttactga tagcatctta acttcctttg aaaggttggt cttctcaagc agtcctcgtg | 2100 |
| gagctggctc ctcagctaat gccaggggac aataatgatc ccctcccaaa accaaacaga | 2160 |
| aaaccatggc aactctggtt tccttgggca gcacctgctt taagaatgag caaatgacca | 2220 |
| atcagctcat gaaactaaat actctattat tactaaaata ttttttttgag acagggcatg | 2280 |
| gaattcatca catagttcag gttggccttg aactcagaga gactcactta cctttgcctc | 2340 |
| ccacgtgctg gaattaaagg catgaaccac cacaccaaac ataacacttg aattttggaa | 2400 |
| gagtccttct tccaatagat ttgaggtttt gaaaatgtgg cacagaaaat atgaattcaa | 2460 |
| atataatgaa acaagagat aactttcaac taagtttcta taggttcttg ctaggaatcc | 2520 |
| taagcttgtc tgaaactcta gagcttctgt ttctagtctt ctgagtgtta gtattgtagg | 2580 |
| tatgtgccct gcctcagtgt gatgtttttg ataatcttaa agaaatcaaa gaaattttat | 2640 |
| aaaagactag actgtgctac acaaaaagaa tattcagatg ccaagaaaga gttcttagaa | 2700 |
| attaagaaat atgctactag tataaatcct ttataaagtg gaatgacaaa tctgatgaaa | 2760 |
| tcttactaaa agtagaaaaa cataaacatc aaagacatga ataataagaa atcatattg | 2820 |
| tgcatatcat taacctaaaa cattaacttg caaaaataga atagtccaaa agtaaacaa | 2880 |
| aataaataaa tcaccaagac atgatacaag gacaattcct agaatgataa aacaagaata | 2940 |
| ttcattataa aaggccctat cactaaagca aacagaaac agactcaaaa gataaatctt | 3000 |
| cattgtcact ggagagaagt catactatca tagcactcag aaggaaataa aaatcaaaat | 3060 |
| gtcaaaaagg acctcagcc | 3079 |

<210> SEQ ID NO 13
<211> LENGTH: 2347
<212> TYPE: DNA
<213> ORGANISM: Cricetulus griseus

<400> SEQUENCE: 13

| | |
|---|---|
| tgaagagaca ccatgaccac agaaactctt ataaaggaaa gcaattattg ggtccagctt | 60 |
| acagttcaga ggtttaatcc attgtcatga ttgcaggaag tatggtggcc cacaggcaga | 120 |
| catggtgctg gagaagtaga tgagagttct atatcagatt gacacacttc ttccaacaag | 180 |
| gccacacctc cactcactct gagcctatgg ggccattttc attcaaacca ccaaagctac | 240 |
| aaggtagctt atacccccagc ttgctatttc tgatgagact tagtaaatag tcttaaaagc | 300 |
| ccataaaatc actcaaaact agtttttta ttattattat tagttcaaat taggaagaag | 360 |
| cttgctttac atgtcaatcc cttctccctc tccctcatca aaactagttt tttgttttt | 420 |
| aggtttttt tcaagacagg gtttctctgt gtagctttgg agcctatcct ggcactcgct | 480 |
| ctggagacca ggctggcctc gaactcacag agatctgcct gcctttgcct cccgagtcct | 540 |
| gggattaaag gcatgcacca ccaacacctg gccaaaatta gttttaagtc cagttctagg | 600 |
| agctccaatg ccctcttttg gcttccatgg gaaccaggaa cactatatat atatatatat | 660 |
| atatatatat atatatatat atatatatat tcaggcaaat atttatgcat ataaaaataa | 720 |
| aataaatctt ttttcctttt ttttttaaag aagtgacatt gtcttggaat ttttgtggct | 780 |
| gctctgccct tatgtgtaac tggacactac cagcatctaa acactggcct gaaaccagcc | 840 |
| aaagaaaacc tttgtgccag gtcctgtgtc aaagtattat gttccttta ggatatccta | 900 |
| tatcctaaag gatttatttt actgatagca tcttaacttc ctttgaaagg ttggtcttct | 960 |
| caagcagtcc tcgtggagct ggctcctcag ctaatgccag gggacaataa tgatcccctc | 1020 |

| | | | |
|---|---|---|---|
| ccaaaaccaa | acagaaaacc | atggcaactc | tggtttcctt | gggcagcacc | tgctttaaga | 1080 |
| atgagcaaat | gaccaatcag | ctcatgaaac | taaatactct | attattacta | aaatatttt | 1140 |
| ttgagacagg | gcatggaatt | catcacatag | ttcaggttgg | ccttgaactc | agagagactc | 1200 |
| acttaccttt | gcctcccacg | tgctggaatt | aaaggcatga | accaccacac | caaacataac | 1260 |
| acttgaattt | tggaagagtc | cttcttccaa | tagatttgag | gttttgaaaa | tgtggcacag | 1320 |
| aaaatatgaa | ttcaaatata | atgaaaacaa | gagataactt | tcaactaagt | ttctataggt | 1380 |
| tcttgctagg | aatcctaagc | ttgtctgaaa | ctctagagct | tctgtttcta | gtcttctgag | 1440 |
| tgttagtatt | gtaggtatgt | gccctgcctc | agtgtgatgt | ttttgataat | cttaaagaaa | 1500 |
| tcaaagaaat | tttataaaag | actagactgt | gctacacaaa | aagaatattc | agatgccaag | 1560 |
| aaagagttct | tagaaattaa | gaaatatgct | actagtataa | atcctttata | aagtggaatg | 1620 |
| acaaatctga | tgaaatctta | ctaaaagtag | aaaaacataa | acatcaaaga | catgaataat | 1680 |
| aagaaaatca | tattgtgcat | atcattaacc | taaaacatta | acttgcaaaa | atagaatagt | 1740 |
| ccaaaaagta | aacaaaataa | ataaatcacc | aagacatgat | acaaggacaa | ttcctagaat | 1800 |
| gataaaacaa | gaatattcat | tataaaaggc | cctatcacta | aagcacaaca | gaaacagact | 1860 |
| caaaagataa | atcttcattg | tcactggaga | gaagtcatac | tatcatagca | ctcagaagga | 1920 |
| aataaaaatc | aaaatgtcaa | aaaggacctc | agcctctgaa | acacaaatac | aaaatatgtc | 1980 |
| cgccttcttg | acaggcatta | ctcttcaatt | aacattttaa | gaaaactata | aagagagctt | 2040 |
| agtattttaa | gaaatctgta | gctatttctt | ttataagcat | gacaactaag | tttcctgatt | 2100 |
| taaacagacc | taaaaaaccg | gtgaagtgag | tggagaaagg | ggatacgaag | acagcatccc | 2160 |
| acatgactgc | tcccagtaaa | ggcaaggtct | tcatccattt | tatcctgaac | tctgggaaat | 2220 |
| ttataaagaa | cagaaatgta | tttctctcag | ttctggagcc | tcagtccagg | acactaagtc | 2280 |
| taggtactac | actctcacat | ggtggaaact | agaaagcaag | ctcacttgtc | actcactacc | 2340 |
| tgatgcc | | | | | | 2347 |

<210> SEQ ID NO 14
<211> LENGTH: 2484
<212> TYPE: DNA
<213> ORGANISM: Cricetulus griseus

<400> SEQUENCE: 14

| | | | |
|---|---|---|---|
| gggattaaag | gcgtgtacca | ccaacgctcg | gcctgtctgt | gaatatttaa | aatgaaaact | 60 |
| ttggaaatgt | tctgaaacca | gctggtgtca | gatagtcaga | gaactttcgt | aaggtaggtg | 120 |
| tgggttatag | cataatccca | cacaagaggc | tgaagcagga | ggattttgtg | tttgagggca | 180 |
| gctagagcca | catggtgagt | ccctgcctca | aaacacaaaa | gcaagacaaa | acaagctcc | 240 |
| aaataagatt | cactgggccc | tttctttcct | tccttctcag | tgagtccact | tgctttaaaa | 300 |
| tcaggtctta | aagacgcact | agatgctgaa | cttaacagta | ataataaata | tcttctctta | 360 |
| cagtacagat | tatgctctat | aaacactgca | ctgataaagt | tcagccttaa | cctttgttct | 420 |
| gtaaatgttt | cctagttttt | ctactgccgt | attataagac | aaatgtcagc | atgaaggcag | 480 |
| gttttttcaga | aaacacagca | gctccacaga | tggcctctaa | tccataatca | ttaaagacaa | 540 |
| gactgcaact | ttttcaactg | gaatcattc | aagatgtttt | tctgaagtcc | ctaccaggac | 600 |
| acaagccacc | ctggttgctg | tgtgacatca | gttaggtaga | ctctgaactg | gcttcccaag | 660 |
| aaattataca | aaagcaaggt | gtcacctagt | attagcataa | cttctgataa | ctactgtctt | 720 |
| agctgggtt | tctattgctg | tgaagagaca | ccatgaccac | agaaactctt | ataaaggaaa | 780 |

| | |
|---|---:|
| gcaattattg ggtccagctt acagttcaga ggtttaatcc attgtcatga ttgcaggaag | 840 |
| tatggtggcc cacaggcaga catggtgctg gagaagtaga tgagagttct atatcagatt | 900 |
| gacacacttc ttccaacaag gccacacctc cactcactct gagcctatgg ggccattttc | 960 |
| attcaaacca ccaaagctac aaggtagctt ataccccagc ttgctatttc tgatgagact | 1020 |
| tagtaaatag tcttaaaagc ccataaaatg actcaaaact agttttttta ttattattat | 1080 |
| tagttcaaat taggaagaag cttgctttac atgtcaatcc cttctccctc tccctcatca | 1140 |
| aaactagttt tttgttttt aggtttttt tcaagacagg gtttctctgt gtagctttgg | 1200 |
| agcctatcct ggcactcgct ctggagacca ggctggcctc gaactcacag agatctgcct | 1260 |
| gcctttgcct cccgagtcct gggattaaag gcatgcacca ccaacacctg gccaaaatta | 1320 |
| gttttaagtc cagttctagg agctccaatg ccctcttttg gcttccatgg gaaccaggaa | 1380 |
| cactatatat atatatatat atatatatat atatatatat atatatatat tcaggcaaat | 1440 |
| atttatgcat ataaaaataa aataaatctt ttttccttt ttttttaaag aagtgacatt | 1500 |
| gtcttggaat ttttgtggct gctctgccct tatgtgtaac tggacactac cagcatctaa | 1560 |
| acactggcct gaaaccagcc aaagaaaacc tttgtgccag gtcctgtgtc aaagtattat | 1620 |
| gttccttta ggatatccta tatcctaaag gatttatttt actgatagca tcttaacttc | 1680 |
| ctttgaaagg ttggtcttct caagcagtcc tcgtggagct ggctcctcag ctaatgccag | 1740 |
| gggacaataa tgatcccctc ccaaaaccaa acagaaaacc atggcaactc tggtttcctt | 1800 |
| gggcagcacc tgctttaaga atgagcaaat gaccaatcag ctcatgaaac taaatactct | 1860 |
| attattacta aaatatttt ttgagacagg gcatggaatt catcacatag ttcaggttgg | 1920 |
| ccttgaactc agagagactc acttacctt gcctcccacg tgctggaatt aaaggcatga | 1980 |
| accaccacac caaacataac acttgaattt tggaagagtc cttcttccaa tagatttgag | 2040 |
| gttttgaaaa tgtggcacag aaaatatgaa ttcaaatata atgaaaacaa gagataactt | 2100 |
| tcaactaagt ttctataggt tcttgctagg aatcctaagc ttgtctgaaa ctctagagct | 2160 |
| tctgtttcta gtcttctgag tgttagtatt gtaggtatgt gccctgcctc agtgtgatgt | 2220 |
| ttttgataat cttaaagaaa tcaaagaaat tttataaaag actagactgt gctacacaaa | 2280 |
| aagaatattc agatgccaag aaagagttct tagaaattaa gaaatatgct actagtataa | 2340 |
| atcctttata aagtggaatg acaaatctga tgaaatctta ctaaaagtag aaaaacataa | 2400 |
| acatcaaaga catgaataat aagaaaatca tattgtgcat atcattaacc taaaacatta | 2460 |
| acttgcaaaa atagaatagt ccaa | 2484 |

<210> SEQ ID NO 15
<211> LENGTH: 3078
<212> TYPE: DNA
<213> ORGANISM: Cricetulus griseus

<400> SEQUENCE: 15

| | |
|---|---:|
| ttcagcctta acctttgttc tgtaaatgtt tcctagtttt tctactgccg tattataaga | 60 |
| caaatgtcag catgaaggca ggttttcag aaaacacagc agctccacag atggcctcta | 120 |
| atccataatc attaaagaca agactgcaac tttttcaact ggaaatcatt caagatgttt | 180 |
| ttctgaagtc cctaccagga cacaagccac cctggttgct gtgtgacatc agttaggtag | 240 |
| actctgaact ggcttcccaa gaaattatac aaaagcaagg tgtcacctag tattagcata | 300 |
| acttctgata actactgtct tagctggggt ttcattgct gtgaagagac accatgacca | 360 |
| cagaaactct tataaaggaa agcaattatt gggtccagct tacagttcag aggtttaatc | 420 |

```
cattgtcatg attgcaggaa gtatggtggc ccacaggcag acatggtgct ggagaagtag    480
atgagagttc tatatcagat tgacacactt cttccaacaa ggccacacct ccactcactc    540
tgagcctatg gggccatttt cattcaaacc accaaagcta caaggtagct tatacccccag   600 cttgctattt ctgatgagac ttagtaaata gtcttaaaag cccataaaat gactcaaaac    660 tagtttttt attattatta ttagttcaaa ttaggaagaa gcttgcttta catgtcaatc     720
ccttctccct ctccctcatc aaaactagtt ttttgttttt taggtttttt ttcaagacag    780
ggtttctctg tgtagctttg gagcctatcc tggcactcgc tctggagacc aggctggcct    840
cgaactcaca gagatctgcc tgcctttgcc tcccgagtcc tgggattaaa ggcatgcacc    900
accaacacct ggccaaaatt agttttaagt ccagttctag gagctccaat gccctctttt    960
ggcttccatg gaaccaggaa cactatata tatatatata tatatatata tatatatata   1020
tatatatata ttcaggcaaa tatttatgca tataaaaata aaataaatct ttttcctttt   1080
tttttttaaa gaagtgacat tgtccttgaa ttttgtggc tgctctgccc ttatgtgtaa    1140
ctggacacta ccagcatcta aacactggcc tgaaaccagc caaagaaaac ctttgtgcca   1200
ggtcctgtgt caaagtatta tgttcctttt aggatatcct atatcctaaa ggatttattt   1260
tactgatagc atcttaactt cctttgaaag gttggtcttc tcaagcagtc ctcgtggagc   1320
tggctcctca gctaatgcca ggggacaata atgatcccct cccaaaacca acagaaaaac   1380
catggcaact ctggtttcct tgggcagcac ctgctttaag aatgagcaaa tgaccaatca   1440
gctcatgaaa ctaaatactc tattattact aaaatatttt tttgagacag ggcatggaat   1500
tcatcacata gttcaggttg gccttgaact cagagagact cacttacctt tgcctcccac   1560
gtgctggaat taaaggcatg aaccaccaca ccaaacataa cacttgaatt ttggaagagt   1620
ccttcttcca atagatttga ggttttgaaa atgtggcaca gaaaatatga attcaaatat   1680
aatgaaaaca agataaact ttcaactaag tttctatagg ttcttgctag gaatcctaag    1740
cttgtctgaa actctagagc ttctgttctc agtcttctga gtgttagtat tgtaggtatg   1800
tgccctgcct cagtgtgatg ttttgataa tcttaaagaa atcaaagaaa ttttataaaa    1860
gactagactg tgctacacaa aaagaatatt cagatgccaa gaaagagttc ttagaaatta   1920
agaaatatgc tactagtata aatcctttat aaagtggaat gacaaatctg atgaaatctt   1980
actaaaagta gaaaaacata aacatcaaag acatgaataa taagaaaatc atattgtgca   2040
tatcattaac ctaaaacatt aacttgcaaa aatagaatag tccaaaagt aaacaaaata    2100 aataaatcac caagacatga tacaaggaca attcctagaa tgataaaaca agaatattca   2160
ttataaaagg ccctatcact aaagcacaac agaaacagac tcaaaagata atcttcatt    2220 gtcactggag agaagtcata ctatcatagc actcagaagg aaataaaaat caaaatgtca   2280
aaaaggacct cagcctctga aacacaaata caaaatatgt ccgccttctt gacaggcatt   2340
actcttcaat taacatttta agaaaactat aagagagct tagtatttta agaaatctgt    2400
agctatttct tttataagca tgacaactaa gtttcctgat ttaaacagac ctaaaaaacc   2460
ggtgaagtga gtggagaaag gggatacgaa gacagcatcc cacatgactg ctcccagtaa   2520
aggcaaggtc ttcatccatt ttatcctgaa ctctgggaaa tttataaaga acagaaatgt   2580
atttctctca gttctgggagc tcagtccag gacactaagt ctaggtacta cactctcaca    2640
tggtggaaac tagaaagcaa gctcacttgt cactcactac ctgatgcctc tttcatcaat   2700
cccattgata aggaagagac ctggcatctc agtttcctaa ggactcagct cttactaaca   2760
ttagctgtca tttctgggtc actgcaacag aaagcctgac agaagcaacc caggggaaga   2820
```

```
aggatgtatt ttggctcact gtctctgagg atttcaactt atcccagcaa taagggata    2880 aaggcattgc agcaggaata tgtgtggcag aagctgttta tgtcacaata aacaaataaa   2940
cacacgctag cgcgcgcgca cacacacaca cacacacaca cacacacaca cacacagaga   3000
gagagagaga gagagagaga gagagagaga gagagagggg gggggcaga cagacagaca    3060 gagggagaga ggcagaga                                                 3078
```

<210> SEQ ID NO 16
<211> LENGTH: 3087
<212> TYPE: DNA
<213> ORGANISM: Cricetulus griseus

<400> SEQUENCE: 16

```
gggattaaag gcgtgtacca ccaacgctcg gcctgtctgt gaatatttaa aatgaaaact     60
ttggaaatgt tctgaaacca gctggtgtca gatagtcaga gaactttcgt aaggtaggtg   120
tgggttatag cataatccca cacaagaggc tgaagcagga ggattttgtg tttgagggca   180
gctagagcca catggtgagt ccctgcctca aaacacaaaa gcaagacaaa acaagctcc    240 aaataagatt cactgggccc tttctttcct tccttctcag tgagtccact tgctttaaaa   300
tcaggtctta aagacgcact agatgctgaa cttaacagta ataataaata tcttctctta   360
cagtacagat tatgctctat aaacactgca ctgataaagt tcagccttaa ccttgttct    420 gtaaatgttt cctagttttt ctactgccgt attataagac aaatgtcagc atgaaggcag   480 gttttcaga aaacacagca gctccacaga tggcctctaa tccataatca ttaaagacaa    540
gactgcaact ttttcaactg gaaatcattc aagatgtttt tctgaagtcc ctaccaggac   600
acaagccacc ctggttgctg tgtgacatca gttaggtaga ctctgaactg gcttcccaag   660
aaattataca aaagcaaggt gtcacctagt attagcataa cttctgataa ctactgtctt   720
agctggggtt tctattgctg tgaagagaca ccatgaccac agaaactctt ataaggaaa    780 gcaattattg ggtccagctt acagttcaga ggtttaatcc attgtcatga ttgcaggaag   840
tatggtggcc cacaggcaga catggtgctg gagaagtaga tgagagttct atatcagatt   900
gacacacttc ttccaacaag gccacacctc cactcactct gagcctatgg ggccattttc   960
attcaaacca ccaaagctac aaggtagctt ataccccagc ttgctatttc tgatgagact   1020
tagtaaatag tcttaaaagc ccataaaatg actcaaaact agttttttta ttattattat   1080
tagttcaaat taggaagaag cttgctttac atgtcaatcc cttctccctc tccctcatca   1140
aaactagttt tttgtttttt aggttttttt tcaagacagg gtttctctgt gtagctttgg   1200
agcctatcct ggcactcgct ctggagacca ggctggcctc gaactcacag agatctgcct   1260
gcctttgcct cccgagtcct gggattaaag gcatgcacca ccaacacctg gccaaaatta   1320
gttttaagtc cagttctagg agctccaatg ccctcttttg gcttccatgg gaaccaggaa   1380
cactatatat atatatatat atatatatat atatatatat atatatatat tcaggcaaat   1440
atttatgcat ataaaaataa aataaatctt ttttccttt tttttaaaag aagtgacatt    1500
gtcttggaat ttttgtggct gctctgccct tatgtgtaac tggacactac cagcatctaa   1560
acactggcct gaaaccagcc aaagaaaacc tttgtgccag gtcctgtgtc aaagtattat   1620
gttcctttta ggatatccta tatcctaaag gattatttt actgatagca tcttaacttc    1680
ctttgaaagg ttggtcttct caagcagtcc tcgtggagct ggctcctcag ctaatgccag   1740
gggacaataa tgatcccctc ccaaaaccaa acagaaaacc atggcaactc tggtttcctt   1800
gggcagcacc tgctttaaga atgagcaaat gaccaatcag ctcatgaaac taatactct    1860
```

-continued

```
attattacta aaatattttt ttgagacagg gcatggaatt catcacatag ttcaggttgg    1920
ccttgaactc agagagactc acttaccttt gcctcccacg tgctggaatt aaaggcatga    1980
accaccacac caaacataac acttgaattt tggaagagtc cttcttccaa tagatttgag    2040
gttttgaaaa tgtggcacag aaaatatgaa ttcaaatata atgaaaacaa gagataactt    2100
tcaactaagt ttctataggt tcttgctagg aatcctaagc ttgtctgaaa ctctagagct    2160
tctgttccta gtcttctgag tgttagtatt gtaggtatgt gccctgcctc agtgtgatgt    2220
ttttgataat cttaaagaaa tcaaagaaat tttataaaag actagactgt gctacacaaa    2280
aagaatattc agatgccaag aaagagttct tagaaattaa gaaatatgct actagtataa    2340
atcctttata aagtggaatg acaaatctga tgaaatctta ctaaaagtag aaaaacataa    2400
acatcaaaga catgaataat aagaaaatca tattgtgcat atcattaacc taaaacatta    2460
acttgcaaaa atagaatagt ccaaaaagta aacaaaataa ataaatcacc aagacatgat    2520
acaaggacaa ttcctagaat gataaaacaa gaatattcat tataaaaggc cctatcacta    2580
aagcacaaca gaaacagact caaaagataa atcttcattg tcactggaga aagtcatac    2640 tatcatagca ctcagaagga aataaaaatc aaaatgtcaa aaaggacctc agcctctgaa    2700
acacaaatac aaaatatgtc cgccttcttg acaggcatta ctcttcaatt aacatttta    2760 gaaaactata aagagagctt agtattttaa gaaatctgta gctatttctt ttataagcat    2820
gacaactaag tttcctgatt taaacagacc taaaaaaccg gtgaagtgag tggagaaagg    2880
ggatacgaag acagcatccc acatgactgc tcccagtaaa ggcaaggtct tcatccattt    2940
tatcctgaac tctgggaaat ttataaagaa cagaaatgta tttctctcag ttctggagcc    3000
tcagtccagg acactaagtc taggtactac actctcacat ggtggaaact agaaagcaag    3060
ctcacttgtc actcactacc tgatgcc                                        3087
```

```
<210> SEQ ID NO 17
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 17
ggccggtacc atatgctccg cattggtctt                                       30

<210> SEQ ID NO 18
<211> LENGTH: 31
<212> TYPE: DNA
<213> ORGANISM: Artificial sequence
<220> FEATURE:
<223> OTHER INFORMATION: Artificially Synthesized Primer Sequence

<400> SEQUENCE: 18
ggccggtacc ggccgctatc gtccattccg a                                     31

<210> SEQ ID NO 19
<211> LENGTH: 1357
<212> TYPE: DNA
<213> ORGANISM: Herpes simplex virus

<400> SEQUENCE: 19
ggccggtacc ggccgctatc gtccattccg acagcatcgc cagtcactat ggcgtgctgc     60
tagcgctata tgcgttgatg caatttctat gcgcacccgt tctcggagca ctgtccgacc    120
gctttggccg ccgcccagtc ctgctcgctt cgctacttgg agccactatc gactacgcga    180
```

| | |
|---|---|
| tcatggcgac cacacccgtc ctgtggatcc gtttggacaa accacaacta gaatgcagtg | 240 |
| aaaaaaatgc tttatttgtg aaatttgtga tgctattgct ttatttgtaa ccattataag | 300 |
| ctgcaataaa caagttaaca acaacaattg cattcatttt atgtttcagg ttcaggggga | 360 |
| ggtgtgggag gttttttaaa gcaagtaaaa cctctacaaa tgtggtatgg ctgattatga | 420 |
| tcctgcctcg cgcgtttcgg tgatgacggt gaaaacctct gacacatgca gctcccggag | 480 |
| acggtcacag cttgtctgta agcggatgcc gggagcagac aagcccgtca gggcgcgtca | 540 |
| gcgggtgttg gcgggtgtcg gggcgcagcc atgacccagt cacgtatcga ctagcttggc | 600 |
| acgccagaaa tccgcgcggt ggttttttggg ggtcggggggg gtttggcagc acagacgcc | 660 |
| cggtgttcgt gtcgcgccag tacatgcggt ccatgcccag gccatccaaa accatgggt | 720 |
| ctgtctgctc agtccagtcg tggaccagac cccacgcaac gcccaaaata taaccccca | 780 |
| cgaaccataa accattcccc atgggggacc ccgtccctaa cccacggggc cagtggctat | 840 |
| ggcagggcct gccgccccga cgttggctgc gagccctggg ccttcacccg aacttggggg | 900 |
| gtggggtggg gaaaggaag aaacgcgggc gtattggccc caatgggggtc tcggtggggt | 960 |
| atcgacagag tgccagccct gggaccgaac cccgcgttta tgaacaaacg acccaacacc | 1020 |
| cgtgcgtttt attctgtctt tttattgccg tcatagcgcg ggttccttcc ggtattgtct | 1080 |
| ccttccgtgt ttcagttagc ctcccccatc tcccctattc ctttgccctc ggacgagtgc | 1140 |
| tggggcgtcg gtttccacta tcggcgagta cttctacaca gccatcggtc cagacggccg | 1200 |
| cgcttctgcg ggcgatttgt gtacgcccga cagtcccggc tccggatcgg acgattgcgt | 1260 |
| cgcatcgacc ctgcgcccaa gctgcatcat cgaaattgcc gtcaaccaag ctctgataga | 1320 |
| gttggtcaag accaatgcgg agcatatggt accggcc | 1357 |

```
<210> SEQ ID NO 20
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 20
```

| | |
|---|---|
| cacccacgat ctttgtgaag | 20 |

```
<210> SEQ ID NO 21
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 21
```

| | |
|---|---|
| atcgactacg cgatcatgg | 19 |

```
<210> SEQ ID NO 22
<211> LENGTH: 900
<212> TYPE: DNA
<213> ORGANISM: Simian Virus 40

<400> SEQUENCE: 22
```

| | |
|---|---|
| cacccacgat ctttgtgaag gaaccttact tctgtggtgt gacataattg gacaaactac | 60 |
| ctacagagat ttaaagctct aaggtaaata taaaattttt aagtgtataa tgtgttaaac | 120 |
| tactgattct aattgtttgt gtattttaga ttccaaccta tggaactgat gaatgggagc | 180 |
| agtggtggaa tgcctttaat gaggaaaacc tgttttgctc agaagaaatg ccatctagtg | 240 |

-continued

| | |
|---|---|
| atgatgaggc tactgctgac tctcaacatt ctactcctcc aaaaaagaag agaaaggtag | 300 |
| aagaccccaa ggactttcct tcagaattgc taagttttt gagtcatgct gtgtttagta | 360 |
| atagaactct tgcttgcttt gctatttaca ccacaaagga aaaagctgca ctgctataca | 420 |
| agaaaattat ggaaaatat tctgtaacct ttataagtag gcataacagt tataatcata | 480 |
| acatactgtt ttttcttact ccacacaggc atagagtgtc tgctattaat aactatgctc | 540 |
| aaaaattgtg tacctttagc ttttttaattt gtaaagggt taataaggaa tatttgatgt | 600 |
| atagtgcctt gactagagat cgatcataat cagccatacc acatttgtag aggttttact | 660 |
| tgctttaaaa aacctcccac acctcccct gaacctgaaa cataaaatga atgcaattgt | 720 |
| tgttgttaac ttgtttattg cagcttataa tggttacaaa taaagcaata gcatcacaaa | 780 |
| tttcacaaat aaagcatttt tttcactgca ttctagttgt ggtttgtcca aactcatcaa | 840 |
| tgtatcttat catgtctgga tccacaggac gggtgtggtc gccatgatcg cgtagtcgat | 900 |

<210> SEQ ID NO 23
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 23
gggcggccgc gctggaggtc gaccagatgt c                                31

<210> SEQ ID NO 24
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 24
gggcggccgc aatttaaaaa aaaaaaaaaa aaaaaa                            36

<210> SEQ ID NO 25
<211> LENGTH: 118
<212> TYPE: DNA
<213> ORGANISM: Homo sapiens

<400> SEQUENCE: 25
ggccgcgctg gaggtcgacc agatgtccga aagtgtcccc ccccccccc ccccggcgc    60 ggagcggcgg ggccactctg gactcttttt tttttttttt tttttttttt taaattgc    118

<210> SEQ ID NO 26
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 26
tgcagcaaaa tccagcatag                                              20

<210> SEQ ID NO 27
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 27
aaggagctga ctgggttgaa                                              20

<210> SEQ ID NO 28
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 28
tcatacacgg tgcctgactg                                              20

<210> SEQ ID NO 29
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 29
ctgccctcca cacagagaac                                              20

<210> SEQ ID NO 30
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 30
tcatacacgg tgcctgactg                                              20

<210> SEQ ID NO 31
<211> LENGTH: 18
<212> TYPE: DNA
<213> ORGANISM: Artificial Sequence
<220> FEATURE:
<223> OTHER INFORMATION: Artificially Synthesized Primer Sequence

<400> SEQUENCE: 31
cagataccgc ccctcctg                                                18

<210> SEQ ID NO 32
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 32
tcatacacgg tgcctgactg                                              20

<210> SEQ ID NO 33
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 33
gggcaagtgg agagcttgt                                               19

<210> SEQ ID NO 34
<211> LENGTH: 20
<212> TYPE: DNA
<213> ORGANISM: Artificial Sequence
<220> FEATURE:

<223> OTHER INFORMATION: Artificially Synthesized Primer Sequence

<400> SEQUENCE: 34
ttgcgggtta catacagtgc					20

<210> SEQ ID NO 35
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 35
aaggagctga ctgggttgaa					20

<210> SEQ ID NO 36
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 36
ctccacttgc ccctttagg					20

<210> SEQ ID NO 37
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 37
aaggagctga ctgggttgaa					20

<210> SEQ ID NO 38
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 38
tctttcttcg gaccttctgc					20

<210> SEQ ID NO 39
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 39
cagccgagca ctctagctct					20

<210> SEQ ID NO 40
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 40
tctttcttcg gaccttctgc					20

<210> SEQ ID NO 41

```
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 41
ggaggaaaac gatgcctaga                                              20

<210> SEQ ID NO 42
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 42
tgcagcaaaa tccagcatag                                              20

<210> SEQ ID NO 43
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 43
ctgccctcca cacagagaac                                              20

<210> SEQ ID NO 44
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 44
ctttcccccg aattgttttc                                              20

<210> SEQ ID NO 45
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 45
cagccgagca ctctagctct                                              20

<210> SEQ ID NO 46
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 46
tcatacacgg tgcctgactg                                              20

<210> SEQ ID NO 47
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 47
```

```
tctcatcctt ggtccctcac                                               20

<210> SEQ ID NO 48
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 48
tgcagcaaaa tccagcatag                                               20

<210> SEQ ID NO 49
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 49
gggcaagtgg agagcttgt                                                19

<210> SEQ ID NO 50
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 50
tctttcttcg gaccttctgc                                               20

<210> SEQ ID NO 51
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 51
tgccttccag gcattaattt                                               20

<210> SEQ ID NO 52
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 52
tcatacacgg tgcctgactg                                               20

<210> SEQ ID NO 53
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 53
ccaatcgcta tgctggattt                                               20

<210> SEQ ID NO 54
<211> LENGTH: 20
<212> TYPE: DNA
<213> ORGANISM: Artificial Sequence
<220> FEATURE:
```

<223> OTHER INFORMATION: Artificially Synthesized Primer Sequence

<400> SEQUENCE: 54
tctttcttcg gaccttctgc                                              20

<210> SEQ ID NO 55
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 55
tctcatcctt ggtccctcac                                              20

<210> SEQ ID NO 56
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 56
tgcagcaaaa tccagcatag                                              20

<210> SEQ ID NO 57
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 57
tgccttccag gcattaattt                                              20

<210> SEQ ID NO 58
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 58
cccccgaatt gttttctctt                                              20

<210> SEQ ID NO 59
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 59
gggcaagtgg agagcttgt                                               19

<210> SEQ ID NO 60
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 60
cttggttatg ccggtactgc                                              20

<210> SEQ ID NO 61

```
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 61
tgaagagaca ccatgaccac a                                              21

<210> SEQ ID NO 62
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 62
tctctgcctc tctccctctg                                                20

<210> SEQ ID NO 63
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 63
ttcagcctta acctttgttc tgt                                            23

<210> SEQ ID NO 64
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 64
ggcatcaggt agtgagtgac aa                                             22

<210> SEQ ID NO 65
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 65
gggattaaag gcgtgtacca                                                20

<210> SEQ ID NO 66
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 66
ggctgaggtc ctttttgaca                                                20

<210> SEQ ID NO 67
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 67
```

```
caggcctttg agctcagact a                                              21

<210> SEQ ID NO 68
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 68
gaggcagggc acatacctac                                                20

<210> SEQ ID NO 69
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 69
tagtgactgg cgatgctgtc                                                20

<210> SEQ ID NO 70
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 70
cttggttatg ccggtactgc                                                20

<210> SEQ ID NO 71
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 71
gagctccaat gccctctttt                                                20

<210> SEQ ID NO 72
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 72
tctctgcctc tctccctctg                                                20

<210> SEQ ID NO 73
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 73
ccttctccct ctccctcatc                                                20

<210> SEQ ID NO 74
<211> LENGTH: 22
<212> TYPE: DNA
<213> ORGANISM: Artificial Sequence
<220> FEATURE:
```

-continued

<223> OTHER INFORMATION: Artificially Synthesized Primer Sequence

<400> SEQUENCE: 74
ggcatcaggt agtgagtgac aa                                          22

<210> SEQ ID NO 75
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 75
tgaagagaca ccatgaccac a                                           21

<210> SEQ ID NO 76
<211> LENGTH: 25
<212> TYPE: DNA
<213> ORGANISM: Artificial Sequence
<220> FEATURE:
<223> OTHER INFORMATION: Artificially Synthesized Primer Sequence

<400> SEQUENCE: 76
ttgggactat tctatttttg caagt                                       25

<210> SEQ ID NO 77
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 77
gggattaaag gcgtgtacca                                             20

<210> SEQ ID NO 78
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 78
tgtggtggtt catgcccttta                                            20

<210> SEQ ID NO 79
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 79
caggcctttg agctcagact a                                           21

<210> SEQ ID NO 80
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 80
tttctttggc tggtttcagg                                             20

<210> SEQ ID NO 81

```
<211> LENGTH: 20
<212> TYPE: DNA
<213> ORGANISM: Artificial Sequence
<220> FEATURE:
<223> OTHER INFORMATION: Artificially Synthesized Primer Sequence

<400> SEQUENCE: 81
tagtgactgg cgatgctgtc                                                   20

<210> SEQ ID NO 82
<211> LENGTH: 1991
<212> TYPE: DNA
<213> ORGANISM: Homo sapiens

<400> SEQUENCE: 82
tgcagcaaaa tccagcatag cgattggttg ctccccgcgt ttgcggcaaa ggcctggagg       60
caggagtaat ttgcaatcct taaagctgaa ttgtgcagtg catcggattt ggaagctact      120
atattcactt aacacttgaa cgctgagctg caaactcaac gggtaataac ccatcttgaa      180
cagcgtacat gctatacaca caccccttt ccccgaattg ttttctcttt tggaggtggt       240
ggagggagag aaaagtttac ttaaaatgcc tttgggtgag ggaccaagga tgagaagaat      300
gttttttgtt tttcatgccg tggaataaca caaaataaaa aatcccgagg aatatacat       360 tatatattaa atatagatca tttcagggag caaacaaatc atgtgtgggg ctgggcaact      420
agctgagtcg aagcgtaaat aaaatgtgaa tacacgtttg cgggttacat acagtgcact      480
ttcactagta ttcagaaaaa attgtgagtc agtgaactag gaaattaatg cctggaaggc      540
agccaaattt taattagctc aagactcccc ccccccccca aaaaaggca cggaagtaat       600 actcctctcc tcttctttga tcagaatcga tgcattttt gtgcatgacc gcatttccaa       660
taataaaagg ggaaagagga cctggaaagg aattaaacgt ccggtttgtc cggggaggaa      720
agagttaacg gtttttttca caagggtctc tgctgactcc cccggctcgg tccacaagct      780
ctccacttgc ccctttagg aagtccggtc ccgcggttcg ggtaccccct gccctccca        840 tattctcccg tctagcacct ttgatttctc ccaaacccgg cagcccgaga ctgttgcaaa      900
ccggcgccac agggcgcaaa ggggatttgt ctcttctgaa acctggctga gaaattggga      960
actccgtgtg ggaggcgtgg gggtgggacg gtggggtaca gactggcaga gagcaggcaa     1020
cctccctctc gccctagccc agctctggaa caggcagaca catctcaggg ctaaacagac     1080
gcctcccgca cggggcccca cggaagcctg agcaggcggg gcaggagggg cggtatctgc     1140
tgctttggca gcaaattggg ggactcagtc tgggtggaag gtatccaatc cagatagctg     1200
tgcatacata atgcataata catgactccc cccaacaaat gcaatgggag tttattcata     1260
acgcgctctc caagtatacg tggcaatgcg ttgctgggtt atttttaatca ttctaggcat    1320 cgttttcctc cttatgcctc tatcattcct ccctatctac actaacatcc cacgctctga     1380
acgcgcgccc attaataccc ttctttcctc cactctccct gggactcttg atcaaagcgc     1440
ggccctttcc ccagccttag cgaggcgccc tgcagcctgg tacgcgcgtg gcgtggcggt     1500
gggcgcgcag tgcgttctct gtgtggaggg cagctgttcc gcctgcgatg atttatactc     1560
acaggacaag gatgcggttt gtcaaacagt actgctacgg aggagcagca gagaaaggga     1620
gagggtttga gagggagcaa agaaaaatgg taggcgcgcg tagttaattc atgcggctct     1680
cttactctgt ttacatccta gagctagagt gctcggctgc ccggctgagt ctcctcccca     1740
ccttccccac cctccccacc ctccccataa gcgcccctcc cgggttccca agcagaggg      1800 cgtggggaa aagaaaaag atcctctctc gctaatctcc gcccaccggc cctttataat       1860
```

-continued

```
gcgagggtct ggacggctga ggaccccga gctgtgctgc tcgcggccgc caccgccggg      1920 cccggccgt ccctggctcc cctcctgcct cgaccgatgc ccttgagagc cttcaaccca      1980
gtcagctcct t                                                          1991
```

<210> SEQ ID NO 83
<211> LENGTH: 2034
<212> TYPE: DNA
<213> ORGANISM: Homo sapiens

<400> SEQUENCE: 83

```
tcatacacgg tgcctgactg cgttagcaat ttaactgtga taaactaccg cattaaagct       60
tgtttggccg ttttagggtt tgttggaatt ttttttttcgt ctatgtactt gtgaattatt     120
tcacgtttgc cattaccggt tctccatagg gtgatgttca ttagcagtgg tgataggtta     180
attttcacca tctcttatgc ggttgaatag tcacctctga accactttttt cctccagtaa    240 ctcctctttc ttcggaccttt ctgcagccaa cctgaaagaa taacaaggag gtggctggaa    300
acttgtttta aggaaccgcc tgtccttccc ccgctggaaa ccttgcacct cggacgctcc     360
tgctcctgcc cccacctgac ccccgccctc gttgacatcc aggcgcgatg atctctgctg     420
ccagtagagg gcacacttac tttactttcg caaacctgaa cgcgggtgct gcccagagag     480
ggggcggagg gaaagacgct ttgcagcaaa atccagcata gcgattggtt gctccccgcg     540
tttgcggcaa aggcctggag gcaggagtaa tttgcaatcc ttaaagctga attgtgcagt     600
gcatcggatt tggaagctac tatattcact taacacttga acgctgagct gcaaactcaa     660
cgggtaataa cccatcttga acagcgtaca tgctatacac acccccttt  cccccgaatt     720 gttttctctt ttggaggtgg tggagggaga gaaaagttta cttaaaatgc ctttgggtga     780
gggaccaagg atgagaagaa tgtttttttgt ttttcatgcc gtggaataac acaaaataaa     840
aaatcccgag ggaatataca ttatatatta aatatagatc atttcaggga gcaaacaaat     900
catgtgtggg gctgggcaac tagctgagtc gaagcgtaaa taaaatgtga atacacgttt     960
gcgggttaca tacagtgcac tttcactagt attcagaaaa aattgtgagt cagtgaacta   1020
ggaaattaat gcctggaagg cagccaaatt ttaattagct caagactccc cccccccccc   1080 aaaaaaggc acggaagtaa tactcctctc ctcttctttg atcagaatcg atgcattttt    1140
tgtgcatgac cgcatttcca ataataaaag gggaaagagg acctggaaag gaattaaacg   1200 tccggttttgt ccggggagga aagagttaac ggttttttttc acagggtctc ctgctgactc   1260
ccccggctcg gtccacaagc tctccacttg cccttttag gaagtccggt cccgcggttc    1320 gggtacccc tgcccctccc atattctccc gtctagcacc tttgatttct cccaaacccg     1380
gcagcccgag actgttgcaa accggcgcca cagggcgcaa aggggatttg tctcttctga    1440
aacctggctg agaaattggg aactccgtgt gggaggcgtg ggggtgggac ggtggggtac    1500
agactggcag agagcaggca acctccctct cgccctagcc cagctctgga acaggcagac    1560
acatctcagg gctaaacaga cgcctcccgc acggggcccc acggaagcct gagcaggcgg    1620
ggcaggaggg gcggtatctg ctgctttggc agcaaattgg gggactcagt ctgggtggaa    1680
ggtatccaat ccagatagct gtgcatacat aatgcataat acatgactcc ccccaacaaa    1740
tgcaatggga gtttattcat aacgcgctct ccaagtatac gtggcaatgc gttgctgggt    1800
tattttaatc attctaggca tcgttttcct ccttatgcct ctatcattcc tccctatcta    1860
cactaacatc ccacgctctg aacgcgcgcc cattaatacc cttctttcct ccactctccc    1920
tgggactctt gatcaaagcg cggcccttc cccagcctta gcgaggcgcc ctgcagcctg     1980
```

```
gtacgcgcgt ggcgtggcgg tgggcgcgca gtgcgttctc tgtgtggagg gcag        2034
```

<210> SEQ ID NO 84
<211> LENGTH: 1640
<212> TYPE: DNA
<213> ORGANISM: Homo sapiens

<400> SEQUENCE: 84

```
tcatacacgg tgcctgactg cgttagcaat ttaactgtga taaactaccg cattaaagct   60
tgtttggccg ttttagggtt tgttggaatt ttttttttcgt ctatgtactt gtgaattatt  120
tcacgtttgc cattaccggt tctccatagg gtgatgttca ttagcagtgg tgataggtta  180
atttcacca tctcttatgc ggttgaatag tcacctctga accactttt cctccagtaa    240
ctcctctttc ttcggaccttt ctgcagccaa cctgaaagaa taacaaggag gtggctggaa 300
acttgtttta aggaaccgcc tgtccttccc ccgctggaaa ccttgcacct cggacgctcc  360
tgctcctgcc cccacctgac ccccgccctc gttgacatcc aggcgcgatg atctctgctg  420
ccagtagagg gcacacttac tttactttcg caaacctgaa cgcgggtgct gcccagagag  480
ggggcggagg gaaagacgct tgcagcaaaa atccagcata gcgattggtt gctccccgcg  540
tttgcggcaa aggcctggag gcaggagtaa tttgcaatcc ttaaagctga attgtgcagt  600
gcatcggatt tggaagctac tatattcact taacacttga acgctgagct gcaaactcaa  660
cgggtaataa cccatcttga acagcgtaca tgctatacac acccccttt ccccccgaatt  720
gttttctctt ttggaggtgg tggagggaga gaaaagttta cttaaaatgc ctttgggtga  780
gggaccaagg atgagaagaa tgttttttgt ttttcatgcc gtggaataac acaaaataaa  840
aaatcccgag ggaatataca ttatatatta aatatagatc atttcaggga gcaaacaaat  900
catgtgtggg gctgggcaac tagctgagtc gaagcgtaaa taaaatgtga atacacgttt  960
gcgggttaca tacagtgcac tttcactagt attcagaaaa aattgtgagt cagtgaacta 1020
ggaaattaat gcctggaagg cagccaaatt ttaattagct caagactccc cccccccccc 1080
aaaaaaaggc acggaagtaa tactcctctc ctcttctttg atcagaatcg atgcatttt  1140
tgtgcatgac cgcatttcca ataataaaag gggaaagagg acctggaaag gaattaaacg 1200
tccggttttgt ccggggagga aagagttaac ggtttttttc acagggtct ctgctgactc  1260
ccccggctcg gtccacaagc tctccacttg cccctttag gaagtccggt cccgcgttc   1320
gggtaccccc tgccctccc atattctccc gtctagcacc tttgatttct cccaaacccg  1380
gcagcccgag actgttgcaa accggcgcca cagggcgcaa aggggatttg tctcttctga 1440
aacctggctg agaaattggg aactccgtgt gggaggcgtg ggggtgggac ggtggggtac 1500
agactggcag agagcaggca acctccctct cgccctagcc cagctctgga acaggcagac 1560
acatctcagg gctaaacaga cgcctcccgc acggggcccc acggaagcct gagcaggcgg 1620
ggcaggaggg gcggtatctg                                             1640
```

<210> SEQ ID NO 85
<211> LENGTH: 1293
<212> TYPE: DNA
<213> ORGANISM: Homo sapiens

<400> SEQUENCE: 85

```
tcatacacgg tgcctgactg cgttagcaat ttaactgtga taaactaccg cattaaagct   60
tgtttggccg ttttagggtt tgttggaatt ttttttttcgt ctatgtactt gtgaattatt  120
tcacgtttgc cattaccggt tctccatagg gtgatgttca ttagcagtgg tgataggtta  180
```

```
attttcacca tctcttatgc ggttgaatag tcacctctga accactttt  cctccagtaa      240 ctcctctttc ttcggacctt ctgcagccaa cctgaaagaa taacaaggag gtggctggaa      300
acttgtttta aggaaccgcc tgtccttccc ccgctggaaa ccttgcacct cggacgctcc      360
tgctcctgcc cccacctgac ccccgccctc gttgacatcc aggcgcgatg atctctgctg      420
ccagtagagg gcacacttac tttactttcg caaacctgaa cgcgggtgct gcccagagag      480
ggggcggagg gaaagacgct ttgcagcaaa atccagcata gcgattggtt gctccccgcg      540
tttgcggcaa aggcctggag gcaggagtaa tttgcaatcc ttaaagctga attgtgcagt      600
gcatcggatt tggaagctac tatattcact taacacttga acgctgagct gcaaactcaa      660
cgggtaataa cccatcttga acagcgtaca tgctatacac acccccttt  ccccgaatt       720 gttttctctt ttggaggtgg tgagggaga  gaaaagttta cttaaaatgc ctttgggtga      780
gggaccaagg atgagaagaa tgttttttgt ttttcatgcc gtggaataac acaaaataaa      840
aaatcccgag ggaatataca ttatatatta aatatagatc atttcaggga gcaaacaaat      900
catgtgtggg gctgggcaac tagctgagtc gaagcgtaaa taaaatgtga atacacgttt      960
gcgggttaca tacagtgcac tttcactagt attcagaaaa aattgtgagt cagtgaacta     1020
ggaaattaat gcctggaagg cagccaaatt ttaattagct caagactccc cccccccc       1080 aaaaaaaggc acgaagtaa  tactcctctc ctcttctttg atcagaatcg atgcatttt      1140 tgtgcatgac cgcatttcca ataataaaag gggaagagg  acctggaaag gaattaaacg     1200
tccggtttgt ccggggagga aagagttaac ggtttttttc acagggtct  ctgctgactc     1260 ccccggctcg gtccacaagc tctccacttg ccc                                  1293

<210> SEQ ID NO 86
<211> LENGTH: 1534
<212> TYPE: DNA
<213> ORGANISM: Homo sapiens

<400> SEQUENCE: 86
ttgcgggtta catacagtgc actttcacta gtattcagaa aaaattgtga gtcagtgaac       60
taggaaatta atgcctggaa ggcagccaaa ttttaattag ctcaagactc ccccccccc      120 ccaaaaaaag gcacggaagt aatactcctc tcctcttctt tgatcagaat cgatgcattt      180
tttgtgcatg accgcatttc aataataaaa gggggaaaga ggacctggaa aggaattaaa      240
cgtccggttt gtccggggag gaaagagtta acggtttttt tcacagggt  ctctgctgac      300 tccccggct  cggtccacaa gctctccact tgccccttt  aggaagtccg gtcccgcggt      360
tcgggtaccc cctgccctc  ccatattctc ccgtctagca cctttgattt ctcccaaacc      420
cggcagcccg agactgttgc aaaccggcgc acagggcgc  aaaggggatt tgtctcttct      480
gaaacctggc tgagaaattg gaactccgt  gtgggaggcg tgggggtggg acggtggggt      540 acagactgg  agagagcagg caacctccct ctcgccctag cccagctctg aacaggcag       600 acacatctca gggctaaaca gacgcctccc gcacggggcc ccacggaagc ctgagcaggc      660
ggggcaggag gggcggtatc tgctgctttg gcagcaaatt gggggactca gtctgggtgg      720
aaggtatcca atccagatag ctgtgcatac ataatgcata atacatgact cccccccaaca     780 aatgcaatgg gagtttattc ataacgcgct ctccaagtat acgtggcaat gcgttgctgg      840
gttattttaa tcattctagg catcgttttc ctccttatgc ctctatcatt cctccctatc      900
tacactaaca tccacgctc  tgaacgcgcg cccattaata cccttctttc ctccactctc      960
cctgggactc ttgatcaaag cgcggccctt tccccagcct tagcgaggcg ccctgcagcc     1020
```

```
tggtacgcgc gtggcgtggc ggtgggcgcg cagtgcgttc tctgtgtgga gggcagctgt      1080
tccgcctgcg atgatttata ctcacaggac aaggatgcgg tttgtcaaac agtactgcta      1140
cggaggagca gcagagaaag ggagagggtt tgagagggag caaaagaaaa tggtaggcgc      1200
gcgtagttaa ttcatgcggc tctcttactc tgtttacatc ctagagctag agtgctcggc      1260
tgcccggctg agtctcctcc ccaccttccc caccctcccc accctcccca taagcgcccc      1320
tcccgggttc ccaaagcaga gggcgtgggg gaaaagaaaa aagatcctct ctcgctaatc      1380
tccgcccacc ggccctttat aatgcgaggg tctggacggc tgaggacccc cgagctgtgc      1440
tgctcgcggc cgccaccgcc gggccccggc cgtccctggc tcccctcctg cctcgaccga      1500
tgcccttgag agccttcaac ccagtcagct cctt                                  1534

<210> SEQ ID NO 87
<211> LENGTH: 1211
<212> TYPE: DNA
<213> ORGANISM: Homo sapiens

<400> SEQUENCE: 87
ctccacttgc ccctttagg aagtccggtc ccgcggttcg ggtaccccct gcccctccca        60
tattctcccg tctagcacct tgatttctc ccaaacccgg cagcccgaga ctgttgcaaa       120
ccggcgccac agggcgcaaa ggggatttgt ctcttctgaa acctggctga aaattgggga      180
actccgtgtg ggaggcgtgg gggtgggacg gtggggtaca gactggcaga gagcaggcaa     240
cctccctctc gccctagccc agctctggaa caggcagaca catctcaggg ctaaacagac      300
gcctcccgca cggggcccca cggaagcctg agcaggcggg gcaggagggg cggtatctgc      360
tgctttggca gcaaattggg ggactcagtc tgggtggaag gtatccaatc cagatagctg      420
tgcatacata atgcataata catgactccc cccaacaaat gcaatgggag tttattcata      480
acgcgctctc caagtatacg tggcaatgcg ttgctgggtt attttaatca ttctaggcat      540
cgttttcctc cttatgcctc tatcattcct ccctatctac actaacatcc cacgctctga      600
acgcgcgccc attaataccc ttctttcctc cactctccct gggactcttg atcaaagcgc      660
ggccctttcc ccagccttag cgaggcgccc tgcagcctgg tacgcgcgtg gcgtggcggt      720
gggcgcgcag tgcgttctct gtgtggaggg cagctgttcc gcctgcgatg atttatactc      780
acaggacaag gatgcggttt gtcaaacagt actgctacgg aggagcagca gagaaaggga      840
gagggtttga gagggagcaa agaaaatgg taggcgcgcg tagttaattc atgcggctct      900
cttactctgt ttacatccta gagctagagt gctcggctgc ccggctgagt ctcctcccca      960
ccttccccac cctccccacc ctcccataa gcgcccctcc cgggttccca aagcagaggg      1020 cgtggggaa aagaaaaaag atcctctctc gctaatctcc gccaccggc cctttataat     1080 gcgagggtct ggacggctga ggacccccga gctgtgctgc tcgcggccgc caccgccggg     1140
ccccggccgt ccctggctcc cctcctgcct cgaccgatgc ccttgagagc cttcaaccca     1200
gtcagctcct t                                                         1211

<210> SEQ ID NO 88
<211> LENGTH: 1976
<212> TYPE: DNA
<213> ORGANISM: Homo sapiens

<400> SEQUENCE: 88
tctttcttcg gaccttctgc agccaacctg aaagaataac aaggaggtgg ctggaaactt       60
gttttaagga accgcctgtc cttccccgc tggaaacctt gcacctcgga cgctcctgct      120
```

| | |
|---|---|
| cctgccccca cctgacccec gccctcgttg acatccaggc gcgatgatct ctgctgccag | 180 |
| tagagggcac acttacttta ctttcgcaaa cctgaacgcg ggtgctgccc agagaggggg | 240 |
| cggagggaaa gacgctttgc agcaaaatcc agcatagcga ttggttgctc cccgcgtttg | 300 |
| cggcaaaggc ctggaggcag gagtaatttg caatccttaa agctgaattg tgcagtgcat | 360 |
| cggatttgga agctactata ttcacttaac acttgaacgc tgagctgcaa actcaacggg | 420 |
| taataaccca tcttgaacag cgtacatgct atacacacac ccctttcccc cgaattgttt | 480 |
| tctcttttgg aggtggtgga gggagagaaa agtttactta aaatgccttt gggtgaggga | 540 |
| ccaaggatga gaagaatgtt ttttgttttt catgccgtgg aataacacaa aataaaaaat | 600 |
| cccgagggaa tatacattat atattaaata tagatcattt cagggagcaa acaaatcatg | 660 |
| tgtgggctg gcaactagc tgagtcgaag cgtaaataaa atgtgaatac acgtttgcgg | 720 |
| gttacataca gtgcactttc actagtattc agaaaaaatt gtgagtcagt gaactaggaa | 780 |
| attaatgcct ggaaggcagc caaattttaa ttagctcaag actccccccc ccccccaaaa | 840 |
| aaaggcacgg aagtaatact cctctcctct tctttgatca gaatcgatgc attttttgtg | 900 |
| catgaccgca tttccaataa taaaggggga aagaggacct ggaaaggaat taaacgtccg | 960 |
| gtttgtccgg ggaggaaaga gttaacggtt tttttcacaa gggtctctgc tgactccccc | 1020 |
| ggctcggtcc acaagctctc cacttgcccc ttttaggaag tccggtcccg cggttcgggt | 1080 |
| acccctgcc cctcccatat tctcccgtct agcacctttg atttctccca aacccggcag | 1140 |
| cccgagactg ttgcaaaccg gcgccacagg gcgcaaaggg gatttgtctc ttctgaaacc | 1200 |
| tggctgagaa attgggaact ccgtgtggga ggcgtggggg tgggacggtg gggtacagac | 1260 |
| tggcagagag caggcaacct ccctctcgcc ctagcccagc tctggaacag gcagacacat | 1320 |
| ctcagggcta aacagacgcc tcccgcacgg ggccccacgg aagcctgagc aggcggggca | 1380 |
| ggaggggcgg tatctgctgc tttggcagca aattggggga ctcagtctgg gtggaaggta | 1440 |
| tccaatccag atagctgtgc atacataatg cataatacat gactccccec aacaaatgca | 1500 |
| atgggagttt attcataacg cgctctccaa gtatacgtgg caatgcgttg ctgggttatt | 1560 |
| ttaatcattc taggcatcgt tttcctcctt atgcctctat cattcctccc tatctacact | 1620 |
| aacatcccac gctctgaacg cgcgcccatt aataccettc tttcctccac tctccctggg | 1680 |
| actcttgatc aaagcgcggc cctttcccca gccttagcga ggcgcccgtc agcctggtac | 1740 |
| gcgcgtggcg tggcggtggg cgcgcagtgc gttctctgtg tggagggcag ctgttccgcc | 1800 |
| tgcgatgatt tatactcaca ggacaaggat gcggtttgtc aaacagtact gctacggagg | 1860 |
| agcagcagag aaagggagag ggtttgagag ggagcaaaag aaaatggtag gcgcgcgtag | 1920 |
| ttaattcatg cggctctctt actctgttta catcctagag ctagagtgct cggctg | 1976 |

<210> SEQ ID NO 89
<211> LENGTH: 1588
<212> TYPE: DNA
<213> ORGANISM: Homo sapiens

<400> SEQUENCE: 89

| | |
|---|---|
| tctttcttcg gaccttctgc agccaacctg aaagaataac aaggaggtgg ctggaaactt | 60 |
| gttttaagga accgcctgtc cttccccgc tggaaacctt gcacctcgga cgctcctgct | 120 |
| cctgccccca cctgacccec gccctcgttg acatccaggc gcgatgatct ctgctgccag | 180 |
| tagagggcac acttacttta ctttcgcaaa cctgaacgcg ggtgctgccc agagaggggg | 240 |
| cggagggaaa gacgctttgc agcaaaatcc agcatagcga ttggttgctc cccgcgtttg | 300 |

-continued

```
cggcaaaggc ctggaggcag gagtaatttg caatccttaa agctgaattg tgcagtgcat      360
cggatttgga agctactata ttcacttaac acttgaacgc tgagctgcaa actcaacggg      420
taataaccca tcttgaacag cgtacatgct atacacacac ccctttcccc cgaattgttt      480
tctcttttgg aggtggtgga gggagagaaa agtttactta aaatgccttt gggtgaggga      540
ccaaggatga aagaatgtt ttttgttttt catgccgtgg aataacacaa aataaaaaat       600
cccgagggaa tatacattat atattaaata tagatcattt cagggagcaa acaaatcatg      660
tgtggggctg gcaactagc tgagtcgaag cgtaaataaa atgtgaatac acgtttgcgg       720
gttacataca gtgcacttt actagtattc agaaaaaatt gtgagtcagt gaactaggaa       780
attaatgcct ggaaggcagc caaattttaa ttagctcaag actcccccc cccccaaaa        840
aaaggcacgg aagtaatact cctctcctct tctttgatca gaatcgatgc atttttttgtg    900
catgaccgca tttccaataa taaaagggga aagaggacct ggaaggaat taaacgtccg       960
gtttgtccgg ggaggaaaga gttaacggtt tttttcacaa gggtctctgc tgactcccc     1020
ggctcggtcc acaagctctc cacttgcccc ttttaggaag tccggtcccg cggttcgggt    1080
accccctgcc cctcccatat tctcccgtct agcacctttg atttctccca aacccggcag    1140
cccgagactg ttgcaaaccg gcgccacagg gcgcaaaggg gatttgtctc ttctgaaacc    1200
tggctgagaa attgggaact ccgtgtggga ggcgtggggg tggacggtg gggtacagac     1260
tggcagagag caggcaacct ccctctcgcc ctagcccagc tctggaacag gcagacacat    1320
ctcagggcta aacagacgcc tcccgcacgg ggccccacgg aagcctgagc aggcggggca    1380
ggagggggcgg tatctgctgc tttggcagca aattggggga ctcagtctgg gtggaaggta   1440
tccaatccag atagctgtgc atacataatg cataatacat gactccccc aacaaatgca     1500
atgggagttt attcataacg cgctctccaa gtatacgtgg caatgcgttg ctgggttatt    1560
ttaatcattc taggcatcgt tttcctcc                                         1588
```

<210> SEQ ID NO 90
<211> LENGTH: 1533
<212> TYPE: DNA
<213> ORGANISM: Homo sapiens

<400> SEQUENCE: 90

```
tgcagcaaaa tccagcatag cgattggttg ctccccgcgt ttgcggcaaa ggcctggagg       60
caggagtaat ttgcaatcct taaagctgaa ttgtgcagtg catcggattt ggaagctact      120
atattcactt aacacttgaa cgctgagctg caaactcaac gggtaataac ccatcttgaa      180
cagcgtacat gctatacaca caccccttc ccccgaattg ttttctcttt tggaggtggt       240
ggagggagag aaaagtttac ttaaaatgcc tttgggtgag gaccaagga tgagaagaat       300
gttttttgtt tttcatgccg tggaataaca caaaataaaa aatcccgagg gaatatacat      360
tatatattaa atatagatca tttcagggag caaacaaatc atgtgtgggg ctgggcaact      420
agctgagtcg aagcgtaaat aaaatgtgaa tacacgtttg cgggttacat acagtgcact      480
ttcactagta ttcagaaaaa attgtgagtc agtgaactag gaaattaatg cctgaaggc      540
agccaaattt taattagctc aagactcccc cccccccca aaaaaggca cggaagtaat       600
actcctctcc tcttctttga tcagaatcga tgcattttt tgtgcatgacc gcatttccaa      660
taataaaagg ggaaagagga cctggaaagg aattaaacgt ccggtttgtc cggggaggaa      720
agagttaacg gttttttca aagggtctc tgctgactcc ccggctcggt tccacaagct        780
ctccacttgc ccctttagg aagtccggtc ccgcggttcg ggtaccccct gcccctccca     840
```

```
tattctcccg tctagcacct ttgatttctc ccaaacccgg cagcccgaga ctgttgcaaa    900
ccggcgccac agggcgcaaa ggggatttgt ctcttctgaa acctggctga gaaattggga    960
actccgtgtg ggaggcgtgg gggtgggacg gtggggtaca gactggcaga gagcaggcaa   1020
cctccctctc gccctagccc agctctggaa caggcagaca catctcaggg ctaaacagac   1080
gcctcccgca cggggcccca cggaagcctg agcaggcggg caggaggggg cggtatctgc   1140
tgctttggca gcaaattggg ggactcagtc tgggtggaag gtatccaatc cagatagctg   1200
tgcatacata atgcataata catgactccc cccaacaaat gcaatgggag tttattcata   1260
acgcgctctc caagtatacg tggcaatgcg ttgctgggtt attttaatca ttctaggcat   1320
cgttttcctc cttatgcctc tatcattcct ccctatctac actaacatcc cacgctctga   1380
acgcgcgccc attaataccc ttctttcctc cactctccct gggactcttg atcaaagcgc   1440 ggcccttttcc ccagccttag cgaggcgccc tgcagcctgg tacgcgcgtg cgtggcggt   1500 gggcgcgcag tgcgttctct gtgtggaggg cag                                1533
```

<210> SEQ ID NO 91
<211> LENGTH: 1514
<212> TYPE: DNA
<213> ORGANISM: Homo sapiens

<400> SEQUENCE: 91

```
ctttcccccg aattgttttc tcttttggag gtggtggagg gagagaaaag tttacttaaa     60
atgcctttgg gtgagggacc aaggatgaga agaatgtttt tgttttttca tgccgtggaa    120
taacacaaaa taaaaaatcc cgagggaata tacattatat attaaatata gatcatttca    180
gggagcaaac aaatcatgtg tggggctggg caactagctg agtcgaagcg taaataaaat    240
gtgaatacac gtttgcgggt tacatacagt gcactttcac tagtattcag aaaaaattgt    300
gagtcagtga actaggaaat taatgcctgg aaggcagcca aatttttaatt agctcaagac    360 tcccccccc cccaaaaaa aggcacggaa gtaatactcc tctcctcttc tttgatcaga    420
atcgatgcat tttttgtgca tgaccgcatt tccaataata aaaggggaaa gaggacctgg    480
aaaggaatta aacgtccggt ttgtccgggg aggaaagagt taacgttttt tttcacaagg    540
gtctctgctg actcccccgg ctcggtccac aagctctcca cttgcccctt ttaggaagtc    600
cggtcccgcg gttcgggtac ccctgcccc tccatattc tcccgtctag cacctttgat    660
ttctcccaaa cccggcagcc cgagactgtt gcaaaccggc gccacagggc gcaaagggga    720
tttgtctctt ctgaaacctg gctgagaaat tgggaactcc gtgtgggagg cgtggggtg    780 ggacggtggg gtacagactg gcagagagca ggcaacctcc ctctcgccct agcccagctc    840
tggaacaggc agacacatct cagggctaaa cagacgcctc ccgcacgggg ccccacggaa    900
gcctgagcag gcggggcagg aggggcggta tctgctgctt tggcagcaaa ttggggact    960 cagtctgggt ggaaggtatc caatccagat agctgtgcat acataatgca taatacatga   1020 ctcccccca caaatgcaat gggagtttat tcataacgcg ctctccaagt atacgtggca   1080
atgcgttgct gggttatttt aatcattcta ggcatcgttt tcctccttat gcctctatca   1140
ttcctcccta tctacactaa catcccacgc tctgaacgcg cgccattaa taccttctt    1200 tcctccactc tccctgggac tcttgatcaa agcgcggccc tttccccagc cttagcgagg   1260
cgccctgcag cctggtacgc gcgtggcgtg cggtgggcg cgcagtgcgt tctctgtgtg   1320
gagggcagct gttccgcctg cgatgattta tactcacagg acaaggatgc ggtttgtcaa   1380
acagtactgc tacggaggag cagcagagaa agggagaggg tttgagaggg agcaaaagaa   1440
```

```
aatggtaggc gcgcgtagtt aattcatgcg gctctcttac tctgtttaca tcctagagct   1500
agagtgctcg gctg                                                      1514

<210> SEQ ID NO 92
<211> LENGTH: 796
<212> TYPE: DNA
<213> ORGANISM: Homo sapiens

<400> SEQUENCE: 92
tcatacacgg tgcctgactg cgttagcaat ttaactgtga taaactaccg cattaaagct     60
tgtttggccg ttttagggtt tgttggaatt ttttttttcgt ctatgtactt gtgaattatt   120
tcacgtttgc cattaccggt tctccatagg gtgatgttca ttagcagtgg tgataggtta   180
attttcacca tctcttatgc ggttaaatag tcacctctga ccactttttt cctccagtaa   240
ctcctctttc ttcggacctt ctgcagccaa cctgaaagaa taacaaggag gtggctggaa   300
acttgtttta aggaaccgcc tgtccttccc ccgctggaaa ccttgcacct cggacgctcc   360
tgctcctgcc cccacctgac ccccgccctc gttgacatcc aggcgcgatg atctctgctg   420
ccagtagagg gcacacttac tttactttcg caaacctgaa cgcgggtgct gcccagagag   480
ggggcggagg gaaagacgct tgcagcaaaa atccagcata gcgattggtt gctccccgcg   540
tttgcggcaa aggcctggag gcaggagtaa tttgcaatcc ttaaagctga attgtgcagt   600
gcatcggatt tggaagctac tatattcact taacacttga acgctgagct gcaaactcaa   660
cgggtaataa cccatcttga acagcgtaca tgctatacac acccccttt ccccgaatt    720 gttttctctt ttggaggtgg tggagggaga gaaaagttta cttaaaatgc ctttgggtga   780
gggaccaagg atgaga                                                    796

<210> SEQ ID NO 93
<211> LENGTH: 792
<212> TYPE: DNA
<213> ORGANISM: Homo sapiens

<400> SEQUENCE: 93
tgcagcaaaa tccagcatag cgattggttg ctccccgcgt ttgcggcaaa ggcctggagg     60
caggagtaat ttgcaatcct taaagctgaa ttgtgcagtg catcggattt ggaagctact   120
atattcactt aacacttgaa cgctgagctg caaactcaac gggtaataac ccatcttgaa   180
cagcgtacat gctatacaca ccccctttc ccccgaattg ttttctcttt tggaggtggt    240
ggagggagag aaaagtttac ttaaaatgcc tttgggtgag ggaccaagga tgaagaat    300 gttttttgtt tttcatgccg tggaataaca caaaataaaa aatcccgagg gaatatacat   360
tatatattaa atatagatca tttcagggag caaacaaatc atgtgtgggg ctgggcaact   420
agctgagtcg aagcgtaaat aaaatgtgaa tacacgtttg cgggttacat acagtgcact   480
ttcactagta ttcagaaaaa attgtgagtc agtgaactag gaaattaatg cctggaaggc   540
agccaaattt taattagctc aagactcccc cccccccca aaaaaggca cggaagtaat    600 actcctctcc tcttctttga tcagaatcga tgcattttt gtgcatgacc gcatttccaa    660
taataaaagg ggaaagagga cctggaaagg aattaaacgt ccggtttgtc cggggaggaa   720
agagttaacg gttttttttca caagggtctc tgctgactcc cccggctcgg tccacaagct   780
ctccacttgc cc                                                        792

<210> SEQ ID NO 94
<211> LENGTH: 798
<212> TYPE: DNA
```

<213> ORGANISM: Homo sapiens

<400> SEQUENCE: 94

```
tctttcttcg gaccttctgc agccaacctg aaagaataac aaggaggtgg ctggaaactt    60
gttttaagga accgcctgtc cttccccgc tggaaacctt gcacctcgga cgctcctgct    120
cctgccccca cctgacccc gccctcgttg acatccaggc gcgatgatct ctgctgccag    180
tagagggcac acttacttta ctttcgcaaa cctgaacgcg ggtgctgccc agagaggggg    240
cggagggaaa gacgctttgc agcaaaatcc agcatagcga ttggttgctc cccgcgtttg    300
cggcaaaggc ctggaggcag gagtaatttg caatccttaa agctgaattg tgcagtgcat    360
cggatttgga agctactata ttcacttaac acttgaacgc tgagctgcaa actcaacggg    420
taataaccca tcttgaacag cgtacatgct atacacacac ccctttcccc cgaattgttt    480
tctcttttgg aggtggtgga gggagagaaa agtttactta aaatgccttt gggtgaggga    540
ccaaggatga gaagaatgtt ttttgttttt catgccgtgg aataacacaa aataaaaaat    600
cccgagggaa tatacattat atattaaata tagatcattt cagggagcaa acaaatcatg    660
tgtgggctg gcaactagc tgagtcgaag cgtaaataaa atgtgaatac acgtttgcgg    720
gttacataca gtgcactttc actagtattc agaaaaaatt gtgagtcagt gaactaggaa    780
attaatgcct ggaaggca                                                  798
```

<210> SEQ ID NO 95
<211> LENGTH: 528
<212> TYPE: DNA
<213> ORGANISM: Homo sapiens

<400> SEQUENCE: 95

```
tcatacacgg tgcctgactg cgttagcaat ttaactgtga taaactaccg cattaaagct    60
tgtttggccg ttttaggggtt tgttggaatt ttttttttcgt ctatgtactt gtgaattatt    120
tcacgtttgc cattaccggt tctccatagg gtgatgttca ttagcagtgg tgataggtta    180
attttcacca tctcttatgc ggttgaatag tcacctctga accacttttt cctccagtaa    240
ctcctctttc ttcggacctt ctgcagccaa cctgaaagaa taacaaggag gtggctggaa    300
acttgtttta aggaaccgcc tgtccttccc ccgctggaaa ccttgcacct cggacgctcc    360
tgctcctgcc cccacctgac ccccgccctc gttgacatcc aggcgcgatg atctctgctg    420
ccagtagagg gcacacttac tttactttcg caaacctgaa cgcgggtgct gcccagagag    480
ggggcggagg gaaagacgct ttgcagcaaa atccagcata gcgattgg                 528
```

<210> SEQ ID NO 96
<211> LENGTH: 552
<212> TYPE: DNA
<213> ORGANISM: Homo sapiens

<400> SEQUENCE: 96

```
tctttcttcg gaccttctgc agccaacctg aaagaataac aaggaggtgg ctggaaactt    60
gttttaagga accgcctgtc cttccccgc tggaaacctt gcacctcgga cgctcctgct    120
cctgccccca cctgacccc gccctcgttg acatccaggc gcgatgatct ctgctgccag    180
tagagggcac acttacttta ctttcgcaaa cctgaacgcg ggtgctgccc agagaggggg    240
cggagggaaa gacgctttgc agcaaaatcc agcatagcga ttggttgctc cccgcgtttg    300
cggcaaaggc ctggaggcag gagtaatttg caatccttaa agctgaattg tgcagtgcat    360
cggatttgga agctactata ttcacttaac acttgaacgc tgagctgcaa actcaacggg    420
```

| | |
|---|---|
| taataaccca tcttgaacag cgtacatgct atacacacac cccttttccc cgaattgttt | 480 |
| tctcttttgg aggtggtgga gggagagaaa agtttactta aaatgccttt gggtgaggga | 540 |
| ccaaggatga ga | 552 |

<210> SEQ ID NO 97
<211> LENGTH: 541
<212> TYPE: DNA
<213> ORGANISM: Homo sapiens

<400> SEQUENCE: 97

| | |
|---|---|
| tgcagcaaaa tccagcatag cgattggttg ctccccgcgt ttgcggcaaa ggcctggagg | 60 |
| caggagtaat ttgcaatcct aaagctgaaa ttgtgcagtg catcggattt ggaagctact | 120 |
| atattcactt aacacttgaa cgctgagctg caaactcaac gggtaataac ccatcttgaa | 180 |
| cagcgtacat gctatacaca cacccctttc ccccgaattg ttttctcttt tggaggtggt | 240 |
| ggagggagag aaaagtttac ttaaaatgcc tttgggtgag gaccaagga tgagaagaat | 300 |
| gttttttgtt tttcatgccg tggaataaca caaaataaaa aatcccgagg gaatatacat | 360 |
| tatatattaa atatagatca tttcagggag caaacaaatc atgtgtgggg ctgggcaact | 420 |
| agctgagtcg aagcgtaaat aaaatgtgaa tacacgtttg cgggttacat acagtgcact | 480 |
| ttcactagta ttcagaaaaa attgtgagtc agtgaactag gaaattaatg cctggaaggc | 540 |
| a | 541 |

<210> SEQ ID NO 98
<211> LENGTH: 583
<212> TYPE: DNA
<213> ORGANISM: Homo sapiens

<400> SEQUENCE: 98

| | |
|---|---|
| cccccgaatt gttttctctt ttggaggtgg tggagggaga gaaaagttta cttaaaatgc | 60 |
| ctttgggtga gggaccaagg atgagaagaa tgttttttgt ttttcatgcc gtggaataac | 120 |
| acaaaataaa aaatcccgag ggaatataca ttatatatta aatatagatc atttcaggga | 180 |
| gcaaacaaat catgtgtggg gctgggcaac tagctgagtc gaagcgtaaa taaaatgtga | 240 |
| atacacgttt gcgggttaca tacagtgcac tttcactagt attcagaaaa aattgtgagt | 300 |
| cagtgaacta ggaaattaat gcctggaagg cagccaaatt ttaattagct caagactccc | 360 |
| cccccccccc aaaaaaggc acggaagtaa tactcctctc ctcttctttg atcagaatcg | 420 |
| atgcattttt tgtgcatgac cgcatttcca ataataaaag gggaagagg acctggaaag | 480 |
| gaattaaacg tccggtttgt ccggggagga aagagttaac ggttttttc acaagggtct | 540 |
| ctgctgactc ccccggctcg gtccacaagc tctccacttg ccc | 583 |

<210> SEQ ID NO 99
<211> LENGTH: 3089
<212> TYPE: DNA
<213> ORGANISM: Cricetulus griseus

<400> SEQUENCE: 99

| | |
|---|---|
| cttggttatg ccggtactgc cgggcctctt gcgggatagc ggccgcaagc tttagaaatt | 60 |
| catcatgaaa atatctgat agttttatgt agtattctga aattcatga ggtcaattga | 120 |
| taccatggct taaatgtgac tcccccagac aggcagattc tgcctgggta atggcattat | 180 |
| gctttcaatc caaaaatgtc tccctcagtt gatggtgttg ttttaggagg ttctagaaat | 240 |
| ttgggatatg ggaccagtct gatggaggtg ggcctttgat ttctctctct ctctctctct | 300 |

```
ctctctctct ctctctctct ctctctccct ctctgcctct ctccctctgt      360
ctgtctgtct gccccccccc ctctctctct ctctctctct ctctctctct      420
ctgtgtgtgt gtgtgtgtgt gtgtgtgtgt gtgtgtgtgc gcgcgcgcta gcgtgtgttt  480
atttgtttat tgtgacataa acagcttctg ccacacatat tcctgctgca atgcctttat  540
cccttttattg ctgggataag ttgaaatcct cagagacagt gagccaaaat acatccttct 600
tccctgggt tgcttctgtc aggctttctg ttgcagtgac ccagaaatga cagctaatgt   660
tagtaagagc tgagtcctta ggaaactgag atgccaggtc tcttccttat caatgggatt  720
gatgaaagag gcatcaggta gtgagtgaca agtgagcttg cttttctagtt tccaccatgt 780
gagagtgtag tacctagact tagtgtcctg gactgaggct ccagaactga gagaaataca  840
tttctgttct ttataaattt cccagagttc aggataaaat ggatgaagac cttgccttta  900
ctgggagcag tcatgtggga tgctgtcttc gtatcccctt tctccactca cttcaccggt  960
tttttaggtc tgtttaaatc agggaaactt agttgtcatg cttataaaag aaatagctac  1020
agatttctta aaatactaag ctctctttaa cagtttatag ttttcttaaa atgttaattg  1080
aagagtaatg cgtgtcaaga aggcgggaca tattttgtat ttgtgtttca gaggctgagg  1140
tccttttttga cattttgatt tttatttcct tctgagtgct atgatagtat ggacttctct  1200
ccagtgacaa tgaagattta tcttttgagt ctgtttctgt tgtgctttag tgatagggcc  1260
ttttataatg aatattcttg ttttatcatt ctaggaattg tccttgtatc atgttcttgg  1320
tgatttattt attttgttta cttttttggga ctattctatt tttgcaagtt aatgttttag  1380
gttaatcata tgcacaatat gattttctta ttattcatgt ctttgatgtt tatgtttttc  1440
tactttttagt aagatttcat cagatttgtc attccacttt ataaaggatt tatactagta  1500
gcatatttct taatttctaa gaactctttc ttggcatctg aatattcttt ttgtgtagca  1560
cagtctagtc ttttataaaa tttctttgat ttctttaaga ttatcaaaaa catcacactg  1620
aggcagggca cataacctaca atactaacac tcagaagcta gaaacaggaa gctctagagt 1680
ttcagacaag cttaggattc ctagcaagaa cctatagaaa cttagttgaa agttatctct  1740
tgttttcatt atatttgaat tcatattttc tgtgccacat tttcaaaacc tcaaatctat  1800
tggaagaagg actcttccaa aattcaagtg ttatgtttgg tgtggtggtt catgcccttta 1860
attccagcac gtgggaggca aaggtaagtg agtctctctg agttcaaggc caacctgaac  1920
tatgtgatga attccatgcc ctgtctcaaa aaaatatttt agtaataata gagtatttag  1980
tttcatgagc tgattggtca tttgctcatt cttaaagcag gtgctgccca aggaaaccag  2040
agttgccatg gttttctgtt tggttttggg aggggatcat tattgtcccc tggcattagc  2100
tgaggagcca gctccacgag gactgcttga gaagaccaac cttcaaagg aagttaagat   2160
gctatcagta aaataaatcc tttaggatat aggatatcct aaaaggaaca taatactttg  2220
acacaggacc tggcacaaag gttttctttg gctggtttca ggccagtgtt tagatgctgg  2280
tagtgtccag ttacacataa gggcagagca gccacaaaaa ttccaagaca atgtcacttc  2340
tttaaaaaaa aaaggaaaaa agattttattt tattttttata tgcataaata tttgcctgaa 2400
tatatatata tatatatata tatatatata tatatatata tatatagtgt tcctggttcc  2460
catgaagcc aaaagagggc attggagctc ctagaactgg acttaaaact aattttggcc    2520
aggtgttggt ggtgcatgcc tttaatccca gcactcggga ggcaaaggca ggcagatctc  2580
tgtgagttcg aggccagcct ggtctccaga gcgagtgcca ggataggctc caaagctaca  2640
cagagaaacc ctgtcttgaa aaaaaaccta aaaaacaaaa aactagtttt gatgagggag  2700
```

| | | | | |
|---|---|---|---|---|
| agggagaagg | gattgacatg | taaagcaagc | ttcttcctaa | tttgaactaa taataataat | 2760 |
| aaaaaaacta | gttttgagtc | attttatggg | cttttaagac | tatttactaa gtctcatcag | 2820 |
| aaatagcaag | ctggggtata | agctaccttg | tagctttggt | ggtttgaatg aaaatggccc | 2880 |
| cataggctca | gagtgagtgg | aggtgtggcc | ttgttggaag | aagtgtgtca atctgatata | 2940 |
| gaactctcat | ctacttctcc | agcaccatgt | ctgcctgtgg | gccaccatac ttcctgcaat | 3000 |
| catgacaatg | gattaaacct | ctgaactgta | agctggaccc | aataattgct ttcctttata | 3060 |
| agagtttctg | tggtcatggt | gtctcttca | | | 3089 |

<210> SEQ ID NO 100
<211> LENGTH: 3091
<212> TYPE: DNA
<213> ORGANISM: Cricetulus griseus

<400> SEQUENCE: 100

| | | | | | |
|---|---|---|---|---|---|
| tctctgcctc | tctccctctg | tctgtctgtc | tgcccccccc | cctctctctc tctctctctc | 60 |
| tctctctctc | tctctctctc | tctgtgtgtg | tgtgtgtgtg | tgtgtgtgtg tgtgtgtgtg | 120 |
| cgcgcgcgct | agcgtgtgtt | tatttgttta | ttgtgacata | aacagcttct gccacacata | 180 |
| ttcctgctgc | aatgccttta | tccctttatt | gctgggataa | gttgaaatcc tcagagacag | 240 |
| tgagccaaaa | tacatccttc | ttcccctggg | ttgcttctgt | caggctttct gttgcagtga | 300 |
| cccagaaatg | acagctaatg | ttagtaagag | ctgagtcctt | aggaaactga gatgccaggt | 360 |
| ctcttcctta | tcaatgggat | tgatgaaaga | ggcatcaggt | agtgagtgac aagtgagctt | 420 |
| gctttctagt | ttccaccatg | tgagagtgta | gtacctagac | ttagtgtcct ggactgaggc | 480 |
| tccagaactg | agagaaatac | atttctgttc | tttataaatt | tcccagagtt caggataaaa | 540 |
| tggatgaaga | ccttgccttt | actgggagca | gtcatgtggg | atgctgtctt cgtatcccct | 600 |
| ttctccactc | acttcaccgg | ttttttaggt | ctgtttaaat | cagggaaact tagttgtcat | 660 |
| gcttataaaa | gaaatagcta | cagatttctt | aaaatactaa | gctctcttta acagtttata | 720 |
| gttttcttaa | aatgttaatt | gaagagtaat | gcgtgtcaag | aaggcgggac atattttgta | 780 |
| tttgtgtttc | agaggctgag | gtccttttg | acattttgat | ttttatttcc ttctgagtgc | 840 |
| tatgatagta | tggacttctc | tccagtgaca | atgaagattt | atcttttgag tctgtttctg | 900 |
| ttgtgcttta | gtgatagggc | cttttataat | gaatattctt | gttttatcat tctaggaatt | 960 |
| gtccttgtat | catgttcttg | gtgatttatt | tattttgttt | acttttgggg actattctat | 1020 |
| ttttgcaagt | taatgtttta | ggttaatcat | atgcacaata | tgattttctt attattcatg | 1080 |
| tctttgatgt | ttatgttttt | ctacttttag | taagatttca | tcagatttgt cattccactt | 1140 |
| tataaaggat | ttatactagt | agcatatttc | ttaatttcta | agaactcttt cttggcatct | 1200 |
| gaatattctt | tttgtgtagc | acagtctagt | cttttataaa | atttctttga tttctttaag | 1260 |
| attatcaaaa | acatcacact | gaggcagggc | acatacctac | aatactaaca ctcagaagct | 1320 |
| agaaacagga | agctctagag | tttcagacaa | gcttaggatt | cctagcaaga acctatagaa | 1380 |
| acttagttga | aagttatctc | ttgttttcat | tatatttgaa | ttcatatttt ctgtgccaca | 1440 |
| ttttcaaaac | ctcaaatcta | ttggaagaag | gactcttcca | aaattcaagt gttatgtttg | 1500 |
| gtgtggtggt | tcatgccttt | aattccagca | cgtgggaggc | aaaggtaagt gagtctctct | 1560 |
| gagttcaagg | ccaacctgaa | ctatgtgatg | aattccatgc | cctgtctcaa aaaaatattt | 1620 |
| tagtaataat | agagtatttta | gtttcatgag | ctgattggtc | atttgctcat tcttaaagca | 1680 |
| ggtgctgccc | aaggaaacca | gagttgccat | ggttttctgt | ttggtttttgg gaggggatca | 1740 |

```
ttattgtccc ctggcattag ctgaggagcc agctccacga ggactgcttg agaagaccaa    1800
cctttcaaag gaagttaaga tgctatcagt aaaataaatc ctttaggata taggatatcc    1860
taaaaggaac ataatacttt gacacaggac ctggcacaaa ggttttcttt ggctggtttc    1920
aggccagtgt ttagatgctg gtagtgtcca gttacacata agggcagagc agccacaaaa    1980
attccaagac aatgtcactt ctttaaaaaa aaaggaaaa aagatttatt ttattttttat    2040 atgcataaat atttgcctga atatatatat atatatatat atatatatat atatatatat    2100
atatatagtg ttcctggttc ccatggaagc caaagagggg cattggagct cctagaactg    2160
gacttaaaac taattttggc caggtgttgg tggtgcatgc ctttaatccc agcactcggg    2220
aggcaaaggc aggcagatct ctgtgagttc gaggccagcc tggtctccag agcgagtgcc    2280
aggataggct ccaaagctac acagagaaac cctgtcttga aaaaaacct aaaaaacaaa    2340 aaactagttt tgatgaggga gagggagaag ggattgacat gtaaagcaag cttcttccta    2400
atttgaacta ataataataa taaaaaaact agttttgagt cattttatgg gcttttaaga    2460
ctatttacta agtctcatca gaaatagcaa gctggggtat aagctaccct gtagctttgg    2520
tggtttgaat gaaaatggcc ccataggctc agagtgagtg gaggtgtggc cttgttggaa    2580
gaagtgtgtc aatctgatat agaactctca tctacttctc cagcaccatg tctgcctgtg    2640
ggccaccata cttcctgcaa tcatgacaat ggattaaacc tctgaactgt aagctggacc    2700
caataattgc tttcctttat aagagtttct gtggtcatgg tgtctcttca cagcaataga    2760
aaccccagct aagacagtag ttatcagaag ttatgctaat actaggtgac accttgcttt    2820
tgtataattt cttgggaagc cagttcagag tctacctaac tgatgtcaca cagcaaccag    2880
ggtggcttgt gtcctggtag ggacttcaga aaaacatctt gaatgatttc cagttgaaaa    2940
agttgcagtc ttgtctttaa tgattatgga ttagaggcca tctgtggagc tgctgtgttt    3000
tctgaaaaac ctgccttcat gctgacattt gtcttataat acggcagtag aaaaactagg    3060
aaacatttac agaacaaagg ttaaggctga a                                   3091

<210> SEQ ID NO 101
<211> LENGTH: 3100
<212> TYPE: DNA
<213> ORGANISM: Cricetulus griseus

<400> SEQUENCE: 101
ggcatcaggt agtgagtgac aagtgagctt gctttctagt ttccaccatg tgagagtgta      60
gtacctagac ttagtgtcct ggactgaggc tccagaactg agagaaatac atttctgttc     120
tttataaatt tcccagagtt caggataaaa tggatgaaga ccttgccttt actgggagca     180
gtcatgtggg atgctgtctt cgtatcccct ttctccactc acttcaccgg ttttttaggt     240
ctgtttaaat cagggaaact tagttgtcat gcttataaaa gaaatagcta cagatttctt     300
aaaatactaa gctctctttta acagtttata gttttcttaa aatgttaatt gaagagtaat     360
gcgtgtcaag aaggcgggac atattttgta tttgtgtttc agaggctgag gtccttttttg     420 acattttgat ttttatttcc ttctgagtgc tatgatagta tggacttctc tccagtgaca     480
atgaagattt atcttttgag tctgtttctg ttgtgcttta gtgatagggc cttttataat     540
gaatattctt gttttatcat tctaggaatt gtccttgtat catgttcttg gtgatttatt     600
tattttgttt actttttggg actattctat ttttgcaagt taatgttttta ggttaatcat     660 atgcacaata tgattttctt attattcatg tctttgatgt ttatgttttt ctactttttag    720 taagatttca tcagatttgt cattccactt tataaaggat ttatactagt agcatatttc     780
```

-continued

| | |
|---|---|
| ttaatttcta agaactcttt cttggcatct gaatattctt tttgtgtagc acagtctagt | 840 |
| cttttataaa atttctttga tttctttaag attatcaaaa acatcacact gaggcagggc | 900 |
| acatacctac aatactaaca ctcagaagct agaaacagga agctctagag tttcagacaa | 960 |
| gcttaggatt cctagcaaga acctatagaa acttagttga aagttatctc ttgttttcat | 1020 |
| tatatttgaa ttcatatttt ctgtgccaca ttttcaaaac ctcaaatcta ttggaagaag | 1080 |
| gactcttcca aaattcaagt gttatgtttg gtgtggtggt tcatgccttt aattccagca | 1140 |
| cgtgggaggc aaaggtaagt gagtctctct gagttcaagg ccaacctgaa ctatgtgatg | 1200 |
| aattccatgc cctgtctcaa aaaatatttt tagtaataat agagtattta gtttcatgag | 1260 |
| ctgattggtc atttgctcat tcttaaagca ggtgctgccc aaggaaacca gagttgccat | 1320 |
| ggttttctgt ttggttttgg gagggggatca ttattgtccc ctggcattag ctgaggagcc | 1380 |
| agctccacga ggactgcttg agaagaccaa cctttcaaag gaagttaaga tgctatcagt | 1440 |
| aaaataaatc ctttaggata taggatatcc taaaaggaac ataatacttt gacacaggac | 1500 |
| ctggcacaaa ggttttcttt ggctggtttc aggccagtgt ttagatgctg gtagtgtcca | 1560 |
| gttacacata agggcagagc agccacaaaa attccaagac aatgtcactt ctttaaaaaa | 1620 |
| aaaaggaaaa aagatttatt ttattttttat atgcataaat atttgcctga atatatatat | 1680 |
| atatatatat atatatatat atatatatat atatatagtg ttcctggttc ccatggaagc | 1740 |
| caaaagaggg cattggagct cctagaactg gacttaaaac taattttggc caggtgttgg | 1800 |
| tggtgcatgc ctttaatccc agcactcggg aggcaaaggc aggcagatct ctgtgagttc | 1860 |
| gaggccagcc tggtctccag agcgagtgcc aggataggct ccaaagctac acagagaaac | 1920 |
| cctgtcttga aaaaaaacct aaaaaacaaa aaactagttt tgatgaggga gagggagaag | 1980 |
| ggattgacat gtaaagcaag cttcttccta atttgaacta ataataataa taaaaaaact | 2040 |
| agttttgagt cattttatgg gcttttaaga ctatttacta agtctcatca gaaatagcaa | 2100 |
| gctggggtat aagctacctt gtagctttgg tggtttgaat gaaaatggcc ccataggctc | 2160 |
| agagtgagtg gaggtgtggc cttgttggaa gaagtgtgtc aatctgatat agaactctca | 2220 |
| tctacttctc cagcaccatg tctgcctgtg gccaccata cttcctgcaa tcatgacaat | 2280 |
| ggattaaacc tctgaactgt aagctggacc caataattgc tttcctttat aagagtttct | 2340 |
| gtggtcatgg tgtctcttca cagcaataga aaccccagct aagacagtag ttatcagaag | 2400 |
| ttatgctaat actaggtgac accttgcttt tgtataattt cttgggaagc cagttcagag | 2460 |
| tctacctaac tgatgtcaca cagcaaccag ggtggcttgt gtcctggtag ggacttcaga | 2520 |
| aaaacatctt gaatgatttc cagttgaaaa agttgcagtc ttgtctttaa tgattatgga | 2580 |
| ttagaggcca tctgtggagc tgctgtgttt tctgaaaaac ctgccttcat gctgacattt | 2640 |
| gtcttataat acggcagtag aaaaactagg aaacatttac agaacaaagg ttaaggctga | 2700 |
| actttatcag tgcagtgttt atagagcata atctgtactg taagagaaga tatttattat | 2760 |
| tactgttaag ttcagcatct agtgcgtctt taagacctga ttttaaagca agtggactca | 2820 |
| ctgagaagga aggaaagaaa gggcccagtg aatcttattt ggagcttgtt tttgtcttgc | 2880 |
| ttttgtgttt tgaggcaggg actcaccatg tggctctagc tgccctcaaa cacaaaatcc | 2940 |
| tcctgcttca gcctcttgtg tgggattatg ctataaccca cacctacctt acgaaagttc | 3000 |
| tctgactatc tgacaccagc tggtttcaga acatttccaa agttttcatt ttaaatattc | 3060 |
| acagacaggc cgagcgttgg tggtacacgc ctttaatccc | 3100 |

<210> SEQ ID NO 102

```
<211> LENGTH: 3079
<212> TYPE: DNA
<213> ORGANISM: Cricetulus griseus

<400> SEQUENCE: 102
ggctgaggtc cttttttgaca ttttgatttt tatttccttc tgagtgctat gatagtatgg      60
acttctctcc agtgacaatg aagatttatc ttttgagtct gtttctgttg tgctttagtg     120
atagggcctt ttataatgaa tattcttgtt ttatcattct aggaattgtc cttgtatcat     180
gttcttggtg atttatttat tttgtttact ttttgggact attctatttt tgcaagttaa     240
tgttttaggt taatcatatg cacaatatga ttttcttatt attcatgtct ttgatgttta     300
tgtttttcta cttttagtaa gatttcatca gatttgtcat tccactttat aaaggattta     360
tactagtagc atatttctta atttctaaga actctttctt ggcatctgaa tattcttttt     420
gtgtagcaca gtctagtctt ttataaaatt tctttgattt ctttaagatt atcaaaaaca     480
tcacactgag gcagggcaca tacctacaat actaacactc agaagctaga acaggaagc     540
tctagagttt cagacaagct taggattcct agcaagaacc tatagaaact tagttgaaag     600
ttatctcttg ttttcattat atttgaattc atatttctg tgccacattt tcaaaacctc     660
aaatctattg gaagaaggac tcttccaaaa ttcaagtgtt atgtttggtg tggtggttca     720
tgcctttaat tccagcacgt gggaggcaaa ggtaagtgag tctctctgag ttcaaggcca     780
acctgaacta tgtgatgaat tccatgccct gtctcaaaaa atattttag taataataga     840
gtatttagtt tcatgagctg attggtcatt tgctcattct taaagcaggt gctgcccaag     900
gaaaccagag ttgccatggt tttctgtttg gttttgggag gggatcatta ttgtcccctg     960
gcattagctg aggagccagc tccacgagga ctgcttgaga agaccaacct ttcaaaggaa    1020
gttaagatgc tatcagtaaa ataaatcctt taggatatag gatatcctaa aaggaacata    1080
atactttgac acaggacctg gcacaaaggt tttctttggc tggtttcagg ccagtgttta    1140
gatgctggta gtgtccagtt acacataagg gcagagcagc cacaaaaatt ccaagacaat    1200
gtcacttctt taaaaaaaaa aggaaaaaag atttatttta tttttatatg cataaatatt    1260
tgcctgaata tatatatata tatatatata tatatatata tatatatata tatagtgttc    1320
ctggttccca tggaagccaa agagggcat tggagctcct agaactggac ttaaaactaa     1380
ttttggccag gtgttggtgg tgcatgcctt taatcccagc actcgggagg caaaggcagg    1440
cagatctctg tgagttcgag gccagcctgg tctccagagc gagtgccagg ataggctcca    1500
aagctacaca gagaaacccct gtcttgaaaa aaaacctaaa aaacaaaaaa ctagttttga    1560
tgagggagag ggagaaggga ttgacatgta aagcaagctt cttcctaatt tgaactaata    1620
ataataataa aaaaactagt tttgagtcat tttatgggct tttaagacta tttactaagt    1680
ctcatcagaa atagcaagct ggggtataag ctaccttgta gctttggtgg tttgaatgaa    1740
aatgccccca taggctcaga gtgagtggag gtgtggcctt gttggaagaa gtgtgtcaat    1800
ctgatataga actctcatct acttctccag caccatgtct gcctgtgggc caccatactt    1860
cctgcaatca tgacaatgga ttaaacctct gaactgtaag ctggacccaa taattgcttt    1920
cctttataag agtttctgtg gtcatggtgt ctcttcacag caatagaaac cccagctaag    1980
acagtagtta tcagaagtta tgctaatact aggtgacacc ttgcttttgt ataatttctt    2040
gggaagccag ttcagagtct acctaactga tgtcacacag caaccagggt ggcttgtgtc    2100
ctggtaggga cttcagaaaa acatcttgaa tgatttccag ttgaaaaagt tgcagtcttg    2160
tctttaatga ttatggatta gaggccatct gtggagctgc tgtgtttct gaaaaacctg     2220
```

-continued

```
ccttcatgct gacatttgtc ttataatacg gcagtagaaa aactaggaaa catttacaga    2280
acaaaggtta aggctgaact ttatcagtgc agtgtttata gagcataatc tgtactgtaa    2340
gagaagatat ttattattac tgttaagttc agcatctagt gcgtctttaa gacctgattt    2400
taaagcaagt ggactcactg agaaggaagg aaagaaaggg cccagtgaat cttatttgga    2460
gcttgttttt gtcttgcttt tgtgttttga ggcagggact caccatgtgg ctctagctgc    2520
cctcaaacac aaaatcctcc tgcttcagcc tcttgtgtgg gattatgcta taacccacac    2580
ctaccttacg aaagttctct gactatctga caccagctgg tttcagaaca tttccaaagt    2640
tttcatttta aatattcaca gacaggccga gcgttggtgg tacacgcctt taatcccagc    2700
actcgggagg cagaggcagg cggatctctg agagttcaag gtcagcctgg tctccagagc    2760
aagtgccagg ataggctcca aagctacaca gagaaaaaca aaaaaaaaaa aaaaaaaaa     2820 aaaaaaaaaa aacaagaaaa aaaagaaaaa tattcacaga caggaagaaa ataacgatgt    2880
gatggcattt tatgtcctcg gtattagttc tccaaagtga cagaatcaaa gaatgaccc     2940 gagtgatggt cagatttgaa ttggttcata tgatcattaa gtctgtcagg tgttaagtgt    3000
gaagactgcc atggacattc atcaagctgg aaagctcaga gaacctgtga gttctgtcta    3060
gtctgagctc aaaggcctg                                                 3079
```

<210> SEQ ID NO 103
<211> LENGTH: 3118
<212> TYPE: DNA
<213> ORGANISM: Cricetulus griseus

<400> SEQUENCE: 103

```
gaggcagggc acatacctac aatactaaca ctcagaagct agaaacagga agctctagag      60
tttcagacaa gcttaggatt cctagcaaga acctatagaa acttagttga aagttatctc     120 ttgtttcat tatatttgaa ttcatatttt ctgtgccaca ttttcaaaac ctcaaatcta      180
ttggaagaag gactcttcca aaattcaagt gttatgtttg gtgtggtggt tcatgccttt     240
aattccagca cgtgggaggc aaaggtaagt gagtctctct gagttcaagg ccaacctgaa     300
ctatgtgatg aattccatgc cctgtctcaa aaaatatttt tagtaataat agagtattta     360
gtttcatgag ctgattggtc atttgctcat tcttaaagca ggtgctgccc aaggaaacca     420
gagttgccat ggttttctgt ttggttttgg gaggggatca ttattgtccc ctggcattag     480
ctgaggagcc agctccacga ggactgcttg agaagaccaa cctttcaaag gaagttaaga     540
tgctatcagt aaaataaatc ctttaggata taggatatcc taaaaggaac ataatacttt     600
gacacaggac ctggcacaaa ggttttcttt ggctggtttc aggccagtgt ttagatgctg     660
gtagtgtcca gttacacata agggcagagc agccacaaaa attccaagac aatgtcactt     720
ctttaaaaaa aaaaggaaaa aagatttatt ttatttttat atgcataaat atttgcctga     780
atatatatat atatatatat atatatatat atatatatat atatatagtg ttcctggttc     840
ccatggaagc caaaagaggg cattggagct cctagaactg gacttaaaac taattttggc     900
caggtgttgg tggtgcatgc ctttaatccc agcactcggg aggcaaaggc aggcagatct     960
ctgtgagttc gaggccagcc tggtctccag agcgagtgcc aggataggct ccaaagctac    1020
acagagaaac cctgtcttga aaaaaaacct aaaaaacaaa aaactagttt tgatgaggga    1080
gagggagaag ggattgacat gtaaagcaag cttcttccta atttgaacta ataataataa    1140
taaaaaaact agtttgagt catttttatgg gcttttaaga ctatttacta agtctcatca    1200
gaaatagcaa gctggggtat aagctacctt gtagctttgg tggtttgaat gaaaatggcc    1260
```

-continued

| | |
|---|---|
| ccataggctc agagtgagtg gaggtgtggc cttgttggaa gaagtgtgtc aatctgatat | 1320 |
| agaactctca tctacttctc cagcaccatg tctgcctgtg ggccaccata cttcctgcaa | 1380 |
| tcatgacaat ggattaaacc tctgaactgt aagctggacc caataattgc tttccttat | 1440 |
| aagagtttct gtggtcatgg tgtctcttca cagcaataga aaccccagct aagacagtag | 1500 |
| ttatcagaag ttatgctaat actaggtgac accttgcttt tgtataattt cttgggaagc | 1560 |
| cagttcagag tctacctaac tgatgtcaca cagcaaccag ggtggcttgt gtcctggtag | 1620 |
| ggacttcaga aaacatctt gaatgatttc cagttgaaaa agttgcagtc ttgtctttaa | 1680 |
| tgattatgga ttagaggcca tctgtggagc tgctgtgttt tctgaaaaac ctgccttcat | 1740 |
| gctgacattt gtcttataat acggcagtag aaaaactagg aaacatttac agaacaaagg | 1800 |
| ttaaggctga actttatcag tgcagtgttt atagagcata atctgtactg taagagaaga | 1860 |
| tatttattat tactgttaag ttcagcatct agtgcgtctt taagacctga ttttaaagca | 1920 |
| agtggactca ctgagaagga aggaaagaaa gggcccagtg aatcttattt ggagcttgtt | 1980 |
| tttgtcttgc ttttgtgttt tgaggcaggg actcaccatg tggctctagc tgccctcaaa | 2040 |
| cacaaaatcc tcctgcttca gcctcttgtg tgggattatg ctataaccca cacctacctt | 2100 |
| acgaaagttc tctgactatc tgacaccagc tggtttcaga acatttccaa agttttcatt | 2160 |
| ttaaatattc acagacaggc cgagcgttgg tggtacacgc ctttaatccc agcactcggg | 2220 |
| aggcagaggc aggcggatct ctgagagttc aaggtcagcc tggtctccag agcaagtgcc | 2280 |
| aggataggct ccaaagctac acagagaaaa acaaaaaaaa aaaaaaaaaa aaaaaaaaa | 2340 |
| aaaaacaaga aaaaaagaa aaatattcac agacaggaag aaaataacga tgtgatggca | 2400 |
| ttttatgtcc tcggtattag ttctccaaag tgacagaatc aaaagaatga cccgagtgat | 2460 |
| ggtcagattt gaattggttc atatgatcat taagtctgtc aggtgttaag tgtgaagact | 2520 |
| gccatggaca ttcatcaagc tggaaagctc agagaacctg tgagttctgt ctagtctgag | 2580 |
| ctcaaaggcc tgagaactat gagagaggca gacttttcta ttccagctgt catctagttg | 2640 |
| gacaaagccc atgccattg ggatggacaa tgtatttac ccagcatact aatctaaatg | 2700 |
| tttatgtcat ccaaaactat ccttacgtgc acccagaatg gttaccaag tgtctgtacc | 2760 |
| tctgtgcccc actcaagttg tcacataata ttaaccatca catctgtatt agttgtgtat | 2820 |
| tactgcacag tagcataacc agaaatgcag cagcctagac acaatacata tttactatat | 2880 |
| cactaaggct ttgtgtgttg ggattctggc atggcttatc tgcatcctat tcttgggacc | 2940 |
| tcaaaagact gcataaggtg ccatgcaggt ctgtgactca tctgagactt ggctgggaag | 3000 |
| gagccacaca atggattcct ttgtgtctat aaaattaagg gcttcagttc cttgctgact | 3060 |
| ccgagctagg aggatccgcg gccgctatcg tccattccga cagcatcgcc agtcacta | 3118 |

<210> SEQ ID NO 104
<211> LENGTH: 2490
<212> TYPE: DNA
<213> ORGANISM: Cricetulus griseus

<400> SEQUENCE: 104

| | |
|---|---|
| cttggttatg ccggtactgc cgggcctctt gcgggatagc ggccgcaagc tttagaaatt | 60 |
| catcatgaaa aatatctgat agttttatgt agtattctga aattacatga ggtcaattga | 120 |
| taccatggct taaatgtgac tcccccagac aggcagattc tgcctgggta atggcattat | 180 |
| gctttcaatc caaaaatgtc tccctcagtt gatggtgttg ttttaggagg ttctagaaat | 240 |
| ttgggatatg ggaccagtct gatggaggtg ggcctttgat ttctctctct ctctctctct | 300 |

```
ctctctctct ctctctctct ctctctctct ctctctccct ctctgcctct ctccctctgt    360
ctgtctgtct gcccccgccc ctctctctct ctctctctct ctctctctct ctctctctct    420
ctgtgtgtgt gtgtgtgtgt gtgtgtgtgt gtgtgtgtgc gcgcgcgcta gcgtgtgttt    480
atttgtttat tgtgacataa acagcttctg ccacacatat tcctgctgca atgcctttat    540
cccttattg ctgggataag ttgaaatcct cagagacagt gagccaaaat acatccttct     600
tccctgggt tgcttctgtc aggctttctg ttgcagtgac ccagaaatga cagctaatgt     660
tagtaagagc tgagtcctta ggaaactgag atgccaggtc tcttccttat caatgggatt    720
gatgaaagag gcatcaggta gtgagtgaca agtgagcttg cttctagtt tccaccatgt     780
gagagtgtag tacctagact tagtgtcctg gactgaggct ccagaactga gagaaataca    840
tttctgttct ttataaattt cccagagttc aggataaaat ggatgaagac cttgccttta    900
ctgggagcag tcatgtggga tgctgtcttc gtatccctt tctccactca cttcaccggt     960
ttttaggtc tgtttaaatc agggaaactt agttgtcatg cttataaaag aaatagctac    1020
agatttctta aaatactaag ctctctttaa cagtttatag ttttcttaaa atgttaattg   1080
aagagtaatg cgtgtcaaga aggcgggaca tattttgtat ttgtgttca gaggctgagg    1140
tcctttttga catttttgatt tttatttcct tctgagtgct atgatagtat ggacttctct   1200
ccagtgacaa tgaagattta tcttttgagt ctgtttctgt tgtgctttag tgataggggcc  1260
ttttataatg aatattcttg ttttatcatt ctaggaattg tccttgtatc atgttcttgg   1320
tgatttattt attttgttta cttttggga ctattctatt tttgcaagtt aatgttttag    1380
gttaatcata tgcacaatat gatttctta ttattcatgt ctttgatgtt tatgttttc     1440
tacttttagt aagatttcat cagatttgtc attccacttt ataaaggatt tatactagta   1500
gcatatttct taatttctaa gaactctttc ttggcatctg aatattcttt ttgtgtagca   1560
cagtctagtc ttttataaaa tttctttgat ttctttaaga ttatcaaaaa catcacactg   1620
aggcagggca cataccctaca atactaacac tcagaagcta gaaacaggaa gctctagagt  1680
ttcagacaag cttaggattc ctagcaagaa cctatagaaa cttagttgaa agttatctct   1740
tgttttcatt atatttgaat tcatatttttc tgtgccacat tttcaaaacc tcaaatctat  1800
tggaagaagg actcttccaa aattcaagtg ttatgtttgg tgtggtggtt catgccttta   1860
attccagcac gtgggaggca aaggtaagtg agtctctctg agttcaaggc caacctgaac   1920
tatgtgatga attccatgcc ctgtctcaaa aaatatttt agtaataata gagtatttag    1980
tttcatgagc tgattggtca tttgctcatt cttaaagcag gtgctgccca aggaaaccag   2040
agttgccatg gttttctgtt tggttttggg aggggatcat tattgtcccc tggcattagc   2100
tgaggagcca gctccacgag gactgcttga gaagaccaac cttcaaagg aagttaagat    2160
gctatcagta aaataaatcc tttaggatat aggatatcct aaaaggaaca taatactttg   2220
acacaggacc tggcacaaag gtttttcttt gctggttttca ggccagtgtt tagatgctgg  2280
tagtgtccag ttacacataa gggcagagca gccacaaaaa ttccaagaca atgtcacttc   2340
tttaaaaaaa aaaggaaaaa agattttattt tatttttata tgcataaata tttgcctgaa  2400
tatatatata tatatatata tatatatata tatatatata tatatagtgt tcctggttcc   2460
catggaagcc aaaagagggc attggagctc                                    2490
```

<210> SEQ ID NO 105
<211> LENGTH: 2371
<212> TYPE: DNA
<213> ORGANISM: Cricetulus griseus

<400> SEQUENCE: 105

```
tctctgcctc tctccctctg tctgtctgtc tgccccccc cctctctctc tctctctctc      60
tctctctctc tctctctctc tctgtgtgtg tgtgtgtgtg tgtgtgtgtg tgtgtgtgtg     120
cgcgcgcgct agcgtgtgtt tatttgttta ttgtgacata aacagcttct gccacacata    180
ttcctgctgc aatgccttta tccctttatt gctgggataa gttgaaatcc tcagagacag    240
tgagccaaaa tacatccttc ttcccctggg ttgcttctgt caggctttct gttgcagtga    300
cccagaaatg acagctaatg ttagtaagag ctgagtcctt aggaaactga gatgccaggt    360
ctcttcctta tcaatgggat tgatgaaaga ggcatcaggt agtgagtgac aagtgagctt    420
gctttctagt ttccaccatg tgagagtgta gtacctagac ttagtgtcct ggactgaggc    480
tccagaactg agagaaatac atttctgttc tttataaatt tcccagagtt caggataaaa    540
tggatgaaga ccttgccttt actgggagca gtcatgtggg atgctgtctt cgtatcccct    600
ttctccactc acttcaccgg ttttttaggt ctgtttaaat cagggaaact tagttgtcat    660
gcttataaaa gaaatagcta cagatttctt aaaatactaa gctctcttta acagtttata    720
gttttcttaa aatgttaatt gaagagtaat gcgtgtcaag aaggcgggac atattttgta    780
tttgtgtttc agaggctgag gtccttttg acattttgat ttttatttcc ttctgagtgc    840
tatgatagta tggacttctc tccagtgaca atgaagattt atcttttgag tctgtttctg    900
ttgtgcttta gtgatagggc cttttataat gaatattctt gttttatcat tctaggaatt    960
gtccttgtat catgttcttg gtgatttatt tattttgttt acttttgggg actattctat   1020
ttttgcaagt taatgtttta ggttaatcat atgcacaata tgattttctt attattcatg   1080
tctttgatgt ttatgttttt ctacttttag taagatttca tcagatttgt cattccactt   1140
tataaaggat ttatactagt agcatatttc ttaatttcta agaactcttt cttggcatct   1200
gaatattctt tttgtgtagc acagtctagt cttttataaa atttctttga tttctttaag   1260
attatcaaaa acatcacact gaggcagggc acatacctac aatactaaca ctcagaagct   1320
agaaacagga agctctagag tttcagacaa gcttaggatt cctagcaaga acctatagaa   1380
acttagttga aagttatctc ttgttttcat tatatttgaa ttcatatttt ctgtgccaca   1440
ttttcaaaac ctcaaatcta ttggaagaag gactcttcca aaattcaagt gttatgtttg   1500
gtgtggtggt tcatgccttt aattccagca cgtgggaggc aaaggtaagt gagtctctct   1560
gagttcaagg ccaacctgaa ctatgtgatg aattccatgc cctgtctcaa aaaaatattt   1620
tagtaataat agagtattta gtttcatgag ctgattggtc atttgctcat tcttaaagca   1680
ggtgctgccc aaggaaacca gagttgccat ggttttctgt ttggttttgg gaggggatca   1740
ttattgtccc ctggcattag ctgaggagcc agctccacga ggactgcttg agaagaccaa   1800
cctttcaaag gaagttaaga tgctatcagt aaaataaatc ctttaggata taggatatcc   1860
taaaaggaac ataatacttt gacacaggac ctggcacaaa ggttttcttt ggctggtttc   1920
aggccagtgt ttagatgctg gtagtgtcca gttacacata agggcagagc agccacaaaa   1980
attccaagac aatgtcactt ctttaaaaaa aaaggaaaa aagatttatt ttatttttat   2040
atgcataaat atttgcctga atatatatat atatatatat atatatatat atatatatat   2100
atatatagtg ttcctggttc ccatggaagc caaagagggc attggagct cctagaactg    2160
gacttaaaac taattttggc caggtgttgg tggtgcatgc ctttaatccc agcactcggg   2220
aggcaaaggc aggcagatct ctgtgagttc gaggccagcc tggtctccag agcgagtgcc   2280
aggataggct ccaaagctac acagagaaac cctgtcttga aaaaaaacct aaaaaacaaa   2340
```

<210> SEQ ID NO 106
<211> LENGTH: 2360
<212> TYPE: DNA
<213> ORGANISM: Cricetulus griseus

<400> SEQUENCE: 106

| | |
|---|---|
| ggcatcaggt agtgagtgac aagtgagctt gctttctagt ttccaccatg tgagagtgta | 60 |
| gtacctagac ttagtgtcct ggactgaggc tccagaactg agagaaatac atttctgttc | 120 |
| tttataaatt tcccagagtt caggataaaa tggatgaaga ccttgccttt actgggagca | 180 |
| gtcatgtggg atgctgtctt cgtatcccct ttctccactc acttcaccgg ttttttaggt | 240 |
| ctgtttaaat cagggaaact tagttgtcat gcttataaaa gaaatagcta cagatttctt | 300 |
| aaaatactaa gctctcttta acagtttata gttttcttaa aatgttaatt gaagagtaat | 360 |
| gcgtgtcaag aaggcgggac atattttgta tttgtgtttc agaggctgag gtcctttttg | 420 |
| acattttgat ttttatttcc ttctgagtgc tatgatagta tggacttctc tccagtgaca | 480 |
| atgaagattt atcttttgag tctgtttctg ttgtgcttta gtgatagggc cttttataat | 540 |
| gaatattctt gttttatcat tctaggaatt gtccttgtat catgttcttg gtgatttatt | 600 |
| tattttgttt acttttgggg actattctat ttttgcaagt taatgttttta ggttaatcat | 660 |
| atgcacaata tgattttctt attattcatg tctttgatgt ttatgttttt ctactttag | 720 |
| taagatttca tcagatttgt cattccactt tataaaggat ttatactagt agcatatttc | 780 |
| ttaatttcta agaactcttt cttggcatct gaatattctt tttgtgtagc acagtctagt | 840 |
| cttttataaa atttctttga tttctttaag attatcaaaa acatcacact gaggcagggc | 900 |
| acatacctac aatactaaca ctcagaagct agaaacagga agctctagag tttcagacaa | 960 |
| gcttaggatt cctagcaaga acctatagaa acttagttga aagttatctc ttgttttcat | 1020 |
| tatatttgaa ttcatatttt ctgtgccaca ttttcaaaac ctcaaatcta ttggaagaag | 1080 |
| gactcttcca aaattcaagt gttatgtttg gtgtggtggt tcatgccttt aattccagca | 1140 |
| cgtgggaggc aaaggtaagt gagtctctct gagttcaagg ccaacctgaa ctatgtgatg | 1200 |
| aattccatgc cctgtctcaa aaaaatattt tagtaataat agagtattta gtttcatgag | 1260 |
| ctgattggtc atttgctcat tcttaaagca ggtgctgccc aaggaaacca gagttgccat | 1320 |
| ggttttctgt ttggttttgg gaggggatca ttattgtccc ctggcattag ctgaggagcc | 1380 |
| agctccacga ggactgcttg agaagaccaa cctttcaaag gaagttaaga tgctatcagt | 1440 |
| aaaataaatc ctttaggata taggatatcc taaaaggaac ataatacttt gacacaggac | 1500 |
| ctggcacaaa ggttttcttt ggctggtttc aggccagtgt ttagatgctg gtagtgtcca | 1560 |
| gttacacata agggcagagc agccacaaaa attccaagac aatgtcactt ctttaaaaaa | 1620 |
| aaaaggaaaa aagatttatt ttattttat atgcataaat atttgcctga atatatatat | 1680 |
| atatatatat atatatatat atatatatat atatatagtg ttcctggttc ccatggaagc | 1740 |
| caaaagaggg cattggagct cctagaactg gacttaaaac taattttggc caggtgttgg | 1800 |
| tggtgcatgc ctttaatccc agcactcggg aggcaaaggc aggcagatct ctgtgagttc | 1860 |
| gaggccagcc tggtctccag agcgagtgcc aggataggct ccaaagctac acagagaaac | 1920 |
| cctgtcttga aaaaaaacct aaaaaacaaa aaactagttt tgatgaggga gagggagaag | 1980 |
| ggattgacat gtaaagcaag cttcttccta atttgaacta ataataataa taaaaaaact | 2040 |
| agttttgagt cattttatgg gcttttaaga ctatttacta agtctcatca gaaatagcaa | 2100 |

```
gctgggtat aagctacctt gtagctttgg tggtttgaat gaaaatggcc ccataggctc    2160
agagtgagtg gaggtgtggc cttgttggaa gaagtgtgtc aatctgatat agaactctca    2220
tctacttctc cagcaccatg tctgcctgtg ggccaccata cttcctgcaa tcatgacaat    2280
ggattaaacc tctgaactgt aagctggacc caataattgc tttcctttat aagagtttct    2340
gtggtcatgg tgtctcttca                                                2360

<210> SEQ ID NO 107
<211> LENGTH: 2485
<212> TYPE: DNA
<213> ORGANISM: Cricetulus griseus

<400> SEQUENCE: 107
ttgggactat tctattttg caagttaatg ttttaggtta atcatatgca caatatgatt      60
ttcttattat tcatgtcttt gatgtttatg tttttctact tttagtaaga tttcatcaga    120
tttgtcattc cactttataa aggatttata ctagtagcat atttcttaat ttctaagaac    180
tctttcttgg catctgaata ttctttttgt gtagcacagt ctagtctttt ataaaatttc    240
tttgatttct ttaagattat caaaaacatc acactgaggc agggcacata cctacaatac    300
taacactcag aagctagaaa caggaagctc tagagtttca gacaagctta ggattcctag    360
caagaaccta tagaaactta gttgaaagtt atctcttgtt ttcattatat ttgaattcat    420
attttctgtg ccacattttc aaaacctcaa atctattgga agaaggactc ttccaaaatt    480
caagtgttat gtttggtgtg gtggttcatg cctttaattc cagcacgtgg gaggcaaagg    540
taagtgagtc tctctgagtt caaggccaac ctgaactatg tgatgaattc catgccctgt    600
ctcaaaaaaa tattttagta ataatagagt atttagtttc atgagctgat tggtcatttg    660
ctcattctta aagcaggtgc tgcccaagga accagagtt gccatggttt tctgtttggt    720
tttgggaggg gatcattatt gtcccctggc attagctgag gagccagctc cacgaggact    780
gcttgagaag accaaccttt caaggaagt taagatgcta tcagtaaaat aaatccttta    840
ggatatagga tatcctaaaa ggaacataat actttgacac aggacctggc acaaaggttt    900
tctttggctg gtttcaggcc agtgtttaga tgctggtagt gtccagttac ataagggc     960 agagcagcca caaaaattcc aagacaatgt cacttcttta aaaaaaaaag gaaaaaagat   1020
ttattttatt tttatatgca taaatatttg cctgaatata tatatatata tatatatata   1080
tatatatata tatatatata tagtgttcct ggttcccatg gaagccaaaa gagggcattg   1140
gagctcctag aactggactt aaaactaatt ttggccaggt gttggtggtg catgcccttta  1200 atcccagcac tcgggaggca aaggcaggca gatctctgtg agttcgaggc cagcctggtc   1260
tccagagcga gtgccaggat aggctccaaa gctacacaga gaaaccctgt cttgaaaaaa   1320
aacctaaaaa acaaaaaact agttttgatg agggagaggg agaagggatt gacatgtaaa   1380
gcaagcttct tcctaatttg aactaataat aataataaaa aaactagttt tgagtcattt   1440
tatgggcttt taagactatt tactaagtct catcagaaat agcaagctgg ggtataagct   1500
accttgtagc tttggtggtt tgaatgaaaa tggccccata ggctcagagt gagtggaggt   1560
gtggccttgt tggaagaagt gtgtcaatct gatatagaac tctcatctac ttctccagca   1620
ccatgtctgc ctgtgggcca ccatacttcc tgcaatcatg acaatggatt aaacctctga   1680
actgtaagct ggacccaata attgctttcc tttataagag tttctgtggt catggtgtct   1740
cttcacagca atagaaaccc cagctaagac agtagttatc agaagttatg ctaatactag   1800
gtgacacctt gcttttgtat aatttcttgg gaagccagtt cagagtctac ctaactgatg   1860
```

```
tcacacagca accagggtgg cttgtgtcct ggtagggact tcagaaaaac atcttgaatg      1920
atttccagtt gaaaaagttg cagtcttgtc tttaatgatt atggattaga ggccatctgt      1980
ggagctgctg tgttttctga aaaacctgcc ttcatgctga catttgtctt ataatacggc      2040
agtagaaaaa ctaggaaaca tttacagaac aaaggttaag gctgaacttt atcagtgcag      2100
tgtttataga gcataatctg tactgtaaga gaagatattt attattactg ttaagttcag      2160
catctagtgc gtctttaaga cctgatttta aagcaagtgg actcactgag aaggaaggaa      2220
agaaagggcc cagtgaatct tatttggagc ttgtttttgt cttgcttttg tgttttgagg      2280
cagggactca ccatgtggct ctagctgccc tcaaacacaa aatcctcctg cttcagcctc      2340
ttgtgtggga ttatgctata acccacacct accttacgaa agttctctga ctatctgaca      2400
ccagctggtt tcagaacatt tccaaagttt tcattttaaa tattcacaga caggccgagc      2460
gttggtggta cacgccttta atccc                                            2485

<210> SEQ ID NO 108
<211> LENGTH: 2371
<212> TYPE: DNA
<213> ORGANISM: Cricetulus griseus

<400> SEQUENCE: 108
tgtggtggtt catgccttta attccagcac gtgggaggca aaggtaagtg agtctctctg        60
agttcaaggc caacctgaac tatgtgatga attccatgcc ctgtctcaaa aaaatatttt       120
agtaataata gagtatttag tttcatgagc tgattggtca tttgctcatt cttaaagcag       180
gtgctgccca aggaaaccag agttgccatg gtttctgtt tggttttggg aggggatcat        240
tattgtcccc tggcattagc tgaggagcca gctccacgag gactgcttga gaagaccaac       300 cttttcaaagg aagttaagat gctatcagta aaataaatcc tttaggatat aggatatcct      360
aaaaggaaca taatactttg acacaggacc tggcacaaag gttttctttg gctggtttca       420
ggccagtgtt tagatgctgg tagtgtccag ttacacataa gggcagagca gccacaaaaa       480
ttccaagaca atgtcacttc tttaaaaaaa aaaggaaaaa agatttattt tattttata        540 tgcataaata tttgcctgaa tatatatata tatatatata tatatatata tatatatata       600
tatatagtgt tcctggttcc catggaagcc aaaagagggc attggagctc ctagaactgg       660
acttaaaact aattttggcc aggtgttggt ggtgcatgcc tttaatccca gcactcggga       720
ggcaaaggca ggcagatctc tgtgagttcg aggccagcct ggtctccaga gcgagtgcca       780
ggataggctc caaagctaca cagagaaacc ctgtcttgaa aaaaaaccta aaaaacaaaa       840
aactagtttt gatgagggag agggagaagg gattgacatg taaagcaagc ttcttcctaa       900
tttgaactaa taataataat aaaaaaacta gttttgagtc attttatggg cttttaagac       960
tatttactaa gtctcatcag aaatagcaag ctggggtata agctaccttg tagctttggt      1020
ggtttgaatg aaaatggccc cataggctca gagtgagtgg aggtgtggcc ttgttggaag      1080
aagtgtgtca atctgatata gaactctcat ctacttctcc agcaccatgt ctgcctgtgg      1140
gccaccatac ttcctgcaat catgacaatg gattaaacct ctgaactgta agctggaccc      1200
aataattgct ttcctttata agagtttctg tggtcatggt gtctcttcac agcaatagaa      1260
accccagcta agacagtagt tatcagaagt tatgctaata ctaggtgaca ccttgctttt      1320
gtataatttc ttgggaagcc agttcagagt ctacctaact gatgtcacac agcaaccagg      1380
gtggcttgtg tcctggtagg gacttcagaa aacatcttg aatgattcc agttgaaaaa       1440 gttgcagtct tgtcttttaat gattatggat tagaggccat ctgtggagct gctgtgtttt      1500
```

-continued

| | |
|---|---|
| ctgaaaaacc tgccttcatg ctgacatttg tcttataata cggcagtaga aaaactagga | 1560 |
| aacatttaca gaacaaaggt taaggctgaa ctttatcagt gcagtgttta tagagcataa | 1620 |
| tctgtactgt aagagaagat atttattatt actgttaagt tcagcatcta gtgcgtcttt | 1680 |
| aagacctgat tttaaagcaa gtggactcac tgagaaggaa ggaaagaaag ggcccagtga | 1740 |
| atcttatttg gagcttgttt ttgtcttgct tttgtgtttt gaggcaggga ctcaccatgt | 1800 |
| ggctctagct gccctcaaac acaaaatcct cctgcttcag cctcttgtgt gggattatgc | 1860 |
| tataacccac acctaccta cgaaagttct ctgactatct gacaccagct ggtttcagaa | 1920 |
| catttccaaa gttttcattt taaatattca cagacaggcc gagcgttggt ggtacacgcc | 1980 |
| tttaatccca gcactcggga ggcagaggca ggcggatctc tgagagttca aggtcagcct | 2040 |
| ggtctccaga gcaagtgcca ggataggctc caaagctaca cagagaaaaa caaaaaaaa | 2100 |
| aaaaaaaaaa aaaaaaaaa aaaacaagaa aaaaagaaa atattcaca gacaggaaga | 2160 |
| aaataacgat gtgatggcat tttatgtcct cggtattagt tctccaaagt gacagaatca | 2220 |
| aaagaatgac ccgagtgatg gtcagatttg aattggttca tatgatcatt aagtctgtca | 2280 |
| ggtgttaagt gtgaagactg ccatggacat tcatcaagct ggaaagctca gagaacctgt | 2340 |
| gagttctgtc tagtctgagc tcaaaggcct g | 2371 |

<210> SEQ ID NO 109
<211> LENGTH: 2495
<212> TYPE: DNA
<213> ORGANISM: Cricetulus griseus

<400> SEQUENCE: 109

| | |
|---|---|
| tttctttggc tggtttcagg ccagtgttta gatgctggta gtgtccagtt acacataagg | 60 |
| gcagagcagc cacaaaaatt ccaagacaat gtcacttctt taaaaaaaaa aggaaaaaag | 120 |
| atttatttta ttttatatg cataaatatt tgcctgaata tatatatata tatatatata | 180 |
| tatatatata tatatatata tatagtgttc ctggttccca tggaagccaa aagagggcat | 240 |
| tggagctcct agaactggac ttaaaactaa ttttggccag gtgttggtgg tgcatgcctt | 300 |
| taatcccagc actcgggagg caaggcagg cagatctctg tgagttcgag gccagcctgg | 360 |
| tctccagagc gagtgccagg ataggctcca aagctacaca gagaaaccct gtcttgaaaa | 420 |
| aaaacctaaa aaacaaaaaa ctagttttga tgagggagag ggagaaggga ttgacatgta | 480 |
| aagcaagctt cttcctaatt tgaactaata ataataataa aaaaactagt tttgagtcat | 540 |
| tttatgggct tttaagacta tttactaagt ctcatcagaa atagcaagct ggggtataag | 600 |
| ctaccttgta gctttggtgg tttgaatgaa aatggcccca taggctcaga gtgagtggag | 660 |
| gtgtggcctt gttggaagaa gtgtgtcaat ctgatataga actctcatct acttctccag | 720 |
| caccatgtct gcctgtgggc caccatactt cctgcaatca tgacaatgga ttaaacctct | 780 |
| gaactgtaag ctggacccaa taattgcttt cctttataag agtttctgtg gtcatggtgt | 840 |
| ctcttcacag caatagaaac cccagctaag acagtagtta tcagaagtta tgctaatact | 900 |
| aggtgacacc ttgcttttgt ataatttctt gggaagccag ttcagagtct acctaactga | 960 |
| tgtcacacag caaccagggt ggcttgtgtc ctggtaggga cttcagaaaa acatcttgaa | 1020 |
| tgatttccag ttgaaaaagt tgcagtcttg tctttaatga ttatggatta gaggccatct | 1080 |

-continued

| | |
|---|---|
| gtggagctgc tgtgttttct gaaaaacctg ccttcatgct gacatttgtc ttataatacg | 1140 |
| gcagtagaaa aactaggaaa catttacaga acaaaggtta aggctgaact ttatcagtgc | 1200 |
| agtgtttata gagcataatc tgtactgtaa gagaagatat ttattattac tgttaagttc | 1260 |
| agcatctagt gcgtctttaa gacctgattt taaagcaagt ggactcactg agaaggaagg | 1320 |
| aaagaaaggg cccagtgaat cttatttgga gcttgttttt gtcttgcttt tgtgttttga | 1380 |
| ggcagggact caccatgtgg ctctagctgc cctcaaacac aaaatcctcc tgcttcagcc | 1440 |
| tcttgtgtgg gattatgcta taacccacac ctaccttacg aaagttctct gactatctga | 1500 |
| caccagctgg tttcagaaca tttccaaagt tttcatttta aatattcaca gacaggccga | 1560 |
| gcgttggtgg tacacgcctt taatcccagc actcgggagg cagaggcagg cggatctctg | 1620 |
| agagttcaag gtcagcctgg tctccagagc aagtgccagg ataggctcca aagctacaca | 1680 |
| gagaaaaaca aaaaaaaaaa aaaaaaaaa aaaaaaaaa aacaagaaaa aaaagaaaaa | 1740 |
| tattcacaga caggaagaaa ataacgatgt gatggcattt tatgtcctcg gtattagttc | 1800 |
| tccaaagtga cagaatcaaa agaatgaccc gagtgatggt cagatttgaa ttggttcata | 1860 |
| tgatcattaa gtctgtcagg tgttaagtgt gaagactgcc atggacattc atcaagctgg | 1920 |
| aaagctcaga gaacctgtga gttctgtcta gtctgagctc aaaggcctga gaactatgag | 1980 |
| agaggcagac ttttctattc cagctgtcat ctagttggac aaagcccatg cccattggga | 2040 |
| tggacaatgt attttaccca gcatactaat ctaaatgttt atgtcatcca aaactatcct | 2100 |
| tacgtgcacc cagaatggtt taccaagtgt ctgtacctct gtgccccact caagttgtca | 2160 |
| cataatatta accatcacat ctgtattagt tgtgtattac tgcacagtag cataaccaga | 2220 |
| aatgcagcag cctagacaca atacatattt actatatcac taaggctttg tgtgttggga | 2280 |
| ttctggcatg gcttatctgc atcctattct tgggacctca aaagactgca taaggtgcca | 2340 |
| tgcaggtctg tgactcatct gagacttggc tgggaaggag ccacacaatg gattcctttg | 2400 |
| tgtctataaa attaagggct tcagttcctt gctgactccg agctaggagg atccgcggcc | 2460 |
| gctatcgtcc attccgacag catcgccagt cacta | 2495 |

<210> SEQ ID NO 110
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 110
gaattcgtcg acggggacgc gtctagag          28

<210> SEQ ID NO 111
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 111
cttaagcagc tgcccctgcg cagagctc          28

<210> SEQ ID NO 112
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 112
ggccgtcgac tcgaccaatt ctcatgtttg a    31

<210> SEQ ID NO 113
<211> LENGTH: 28
<212> TYPE: DNA
<213> ORGANISM: Artificial Sequence
<220> FEATURE:
<223> OTHER INFORMATION: Artificially Synthesized Primer Sequence

<400> SEQUENCE: 113
ggccacgcgt agggctctgg gcttgaat    28

<210> SEQ ID NO 114
<211> LENGTH: 466
<212> TYPE: DNA
<213> ORGANISM: Simian virus 40

<400> SEQUENCE: 114

```
aattcgtcga catcgataag ctagcttctg tggaatgtgt gtcagttagg gtgtggaaag    60
tccccaggct ccccagcagg cagaagtatg caaagcatgc atctcaatta gtcagcaacc   120
aggtgtggaa agtccccagg ctccccagca ggcagaagta tgcaaagcat gcatctcaat   180
tagtcagcaa ccatagtccc gcccctaact ccgcccatcc cgcccctaac tccgcccagt   240
tccgcccatt ctccgcccca tggctgacta ttttttttta tttatgcaga ggccgaggcc   300
gcctcggcct ctgagctatt ccagaagtag tgaggaggct tttttggagg cctaggcttt   360
tgcaaaaagc tcccctcgagg aactggaaaa ccagaaagtt aactggtaag tttagtcttt   420
ttgtctttta tttcaggtcc cggatcgaat tgcggccgca cgcgtc              466
```

<210> SEQ ID NO 115
<211> LENGTH: 663
<212> TYPE: DNA
<213> ORGANISM: Simian virus 40

<400> SEQUENCE: 115

```
aattcgagaa tgggcggaac tgggcggagt taggggcggg atgggcggag ttaggggcgg    60
gactatggtt gctgactaat tgagatgcat gctttgcata cttctgcctg ctggggagcc   120
tggttgctga ctaattgaga tgcatgcttt gcatacttct gcctgctggg gagcctgggg   180
actttccaca ccctaactga cacacattcc acagctgcct cgcgcgtttc ggtgatgacg   240
gtgaaaacct ctgacacatg cagctcccgg agacggtcac agcttgtctg taagcggatg   300
ccgggagcag acaagcccgt cagggcgcgt cagcgggtgt tggcgggtgt cggggcgcag   360
ccatgaccca gtcacgtagc gatagcggag tgtatcaggc tcgcatctct ccttcacgcg   420
cccgccgcct tacctgaggc cgccatccac gccggttgag tcgcgttctg ccgcctcccg   480
cctgtggtgc ctcctgaact acgtccgccg tctaggtaag tttagagcta ggtcgagacc   540
gggcctttgt ccggcgctcc cttggagcct acctagactc agccggctct ccacgctttg   600
cctgaccctg cttgctcaac tctacgtctt tgtttcgttt tctgttctgc gccgttacag   660
atc                                                                  663
```